United States Patent
McCall et al.

(10) Patent No.: US 10,392,381 B2
(45) Date of Patent: *Aug. 27, 2019

(54) PREVENTION AND TREATMENT OF NON-ALCOHOLIC FATTY LIVER DISEASE

(71) Applicant: Ohio University, Athens, OH (US)

(72) Inventors: Kelly D. McCall, Athens, OH (US); Frank L. Schwartz, Vienna, WV (US); Douglas J. Goetz, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/326,771

(22) PCT Filed: May 6, 2015

(86) PCT No.: PCT/US2015/029460
§ 371 (c)(1),
(2) Date: Jan. 17, 2017

(87) PCT Pub. No.: WO2016/010609
PCT Pub. Date: Jan. 21, 2016

(65) Prior Publication Data
US 2017/0196845 A1    Jul. 13, 2017

Related U.S. Application Data

(60) Provisional application No. 62/026,164, filed on Jul. 18, 2014, provisional application No. 62/026,197, (Continued)

(51) Int. Cl.
| | |
|---|---|
| A61K 31/4439 | (2006.01) |
| C07D 417/14 | (2006.01) |
| A61K 31/4166 | (2006.01) |
| A61K 31/427 | (2006.01) |
| A61K 31/428 | (2006.01) |
| A61K 31/155 | (2006.01) |

(Continued)

(52) U.S. Cl.
CPC .......... *C07D 417/14* (2013.01); *A61K 31/155* (2013.01); *A61K 31/4166* (2013.01); *A61K 31/427* (2013.01); *A61K 31/428* (2013.01); *A61K 31/4439* (2013.01); *A61K 45/06* (2013.01); *C07D 233/84* (2013.01); *C07D 277/16* (2013.01); *C07D 277/36* (2013.01); *C07D 277/84* (2013.01); *C07D 405/04* (2013.01); *C07D 413/04* (2013.01); *C07D 417/04* (2013.01); *C07D 417/06* (2013.01); *Y02A 50/411* (2018.01)

(58) Field of Classification Search
CPC .................................................. A61K 31/4439
See application file for complete search history.

(56) References Cited

U.S. PATENT DOCUMENTS

| | | |
|---|---|---|
| 4,129,656 A | 12/1978 | Lang et al. |
| 4,182,769 A | 1/1980 | Cherkofsky et al. |

(Continued)

FOREIGN PATENT DOCUMENTS

| | | |
|---|---|---|
| AU | 2005275023 B2 | 3/2012 |
| DE | 2459120 A1 | 6/1975 |

(Continued)

OTHER PUBLICATIONS

Mayo Clinic. "Nonalcoholic fatty liver disease." © 2017. Available from: <https://www.mayoclinic.org/diseases-conditions/nonalcoholic-fatty-liver-disease/diagnosis-treatment/drc-20354573 >.*

(Continued)

*Primary Examiner* — Noble E Jarrell
*Assistant Examiner* — John S Kenyon
(74) *Attorney, Agent, or Firm* — Dinsmore & Shohl, LLP

(57) ABSTRACT

Methods for preventing, treating, and/or reducing the risk of developing non-alcoholic fatty liver disease in a subject in need thereof and pharmaceutical compositions for the prevention or treatment of non-alcoholic fatty liver disease. Methods for inhibiting excessive accumulation of fat in liver tissue. The methods include administering to the subject or contacting the liver tissue with a therapeutically effective amount of at least one compound of General Formula (I) or General Formula (II): or pharmaceutically-acceptable salts or solvates thereof. The pharmaceutical composition includes at least one compound of the General Formula (I) or the General Formula (II) for administration to a subject for the prevention or treatment of non-alcoholic fatty liver disease.

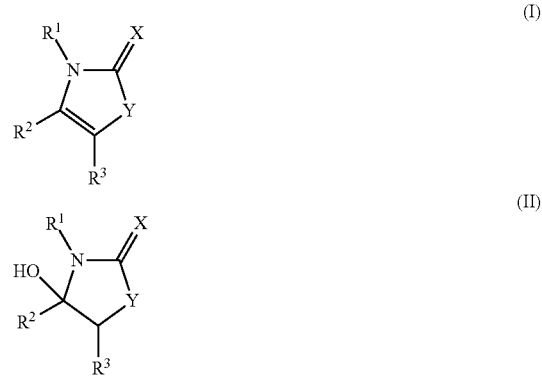

17 Claims, 4 Drawing Sheets

Related U.S. Application Data filed on Jul. 18, 2014, provisional application No. 62/026,234, filed on Jul. 18, 2014.

(51) Int. Cl.

| | | |
|---|---|---|
| A61K 45/06 | (2006.01) | |
| C07D 233/84 | (2006.01) | |
| C07D 277/16 | (2006.01) | |
| C07D 277/36 | (2006.01) | |
| C07D 277/84 | (2006.01) | |
| C07D 405/04 | (2006.01) | |
| C07D 413/04 | (2006.01) | |
| C07D 417/04 | (2006.01) | |
| C07D 417/06 | (2006.01) | |

(56) References Cited

U.S. PATENT DOCUMENTS

| | | | |
|---|---|---|---|
| 4,636,516 | A | 1/1987 | Kubo et al. |
| 4,734,421 | A | 3/1988 | Hammond et al. |
| 5,162,360 | A | 11/1992 | Creswell et al. |
| 5,556,754 | A | 9/1996 | Singer et al. |
| 6,365,616 | B1 | 4/2002 | Kohn et al. |
| 6,465,472 | B1 | 10/2002 | Upasani et al. |
| 6,924,274 | B2 | 8/2005 | Lardy et al. |
| 7,928,132 | B2 | 4/2011 | Kohn et al. |
| 10,023,567 | B2 * | 7/2018 | Goetz ............... A61K 31/4166 |
| 2005/0209295 | A1 | 9/2005 | Kohn et al. |
| 2005/0277678 | A1 | 12/2005 | Lohray et al. |
| 2006/0211752 | A1 | 9/2006 | Kohn et al. |
| 2007/0244138 | A1 | 10/2007 | Boeckx et al. |
| 2008/0171700 | A1 | 7/2008 | Nilsson et al. |
| 2010/0004304 | A1 | 1/2010 | Kohn et al. |
| 2012/0136035 | A1 | 5/2012 | Gil |
| 2012/0283303 | A1 | 11/2012 | Pannecouque et al. |

FOREIGN PATENT DOCUMENTS

| | | | | |
|---|---|---|---|---|
| EP | 692483 | A1 | 1/1996 | |
| FR | 6751 | M | 3/1969 | |
| WO | 9723200 | A1 | 7/1997 | |
| WO | 9852558 | A1 | 11/1998 | |
| WO | 9932106 | A1 | 7/1999 | |
| WO | 9932110 | A1 | 7/1999 | |
| WO | 9932111 | A1 | 7/1999 | |
| WO | 9932455 | A1 | 7/1999 | |
| WO | 0012175 | A2 | 3/2000 | |
| WO | 0025756 | A2 | 5/2000 | |
| WO | 2004017962 | A2 | 3/2004 | |
| WO | 2005094819 | A1 | 10/2005 | |
| WO | 2005118574 | A1 | 12/2005 | |
| WO | 2006019962 | A1 | 2/2006 | |
| WO | 2009049018 | A1 | 4/2009 | |
| WO | WO-2016010610 | A2 * | 1/2016 | ......... A61K 31/4166 |

OTHER PUBLICATIONS

Uhl, E.W., et al. "Mouse Models as Predictors of Human Responses: Evolutionary Medicine." Curr. Pathobiol Rep. (2015), vol. 3, pp. 219-223.*

Ibrahim, S.H., et al. "Glycogen Synthase Kinase-3 (GSK-3) Inhibition Attenuates Hepatocyte Lipoapoptosis." J. Hepatol. Accessed Aug. 30, 2018. (Apr. 2011), vol. 54, Issue 4, pp. 765-772. (Year: 2011).*

Department of Surgery. University of California San Francisco. "Fatty Liver Disease (Nonalcoholic Steatohepatitis." (Apr. 4, 2004). Accessed Aug. 30, 2018. Available from: < https://surgery.ucsf.edu/conditions--procedures/fatty-liver-disease-(nonalcoholic-steatohepatitis). aspx >. (Year: 2004).*

Safaei-Ghomi et al. The reaction of carbon disulfide with bromoacetophenone in the presence of primary amines: synthesis of 3-alkyl-4-phenyl-1,3-thiazole=2(3H)-thione derivatives. J. Sulfur Chem. 33(1): 87-92, 2012. [retrieved on Sep. 21, 2015]. Internet: http://vvvvw.researchgate.net/publication/254291697.

Belfort et al. A Placebo-Controlled Trial of Pioglitazone in Subjects with Nonalcoholic Steatohepatitis. N. Engl. J. Med. 355(22): 2297-2307, 2006. [retrieved on Sep. 22, 2015]. Internet: http://www.nejm.org/doi/pdf/10.1056/NEJMoa060326.

PubChem, Compound Summary for CID 19897000, Create Date: Dec. 5, 2007 [retrieved on Jun. 17, 2015]. Internet: https://pubchem.ncbi.nlrn.nih.gov/substance/32721570.

Emami et al. Synthesis and Evaluation of 2(3H)-Thiazole Thiones as Tyrosinase Inhibitors. Arch. Pharm. Chem: Life Sci. 345(8); 629-637, 2012. entire document.

Hassanabadi, A., "Three-Component and One-Pot Reaction Between Phenacyl Bromide and Primary Amines in the Present of Carbon Disulfied" Journal of Chemical Research 37.2 (2013); pp. 71-72.

Gan, S.F., "Water-Mediated Multicomponent Reaction: a Facile and Efficient Synthesis of Multisubstituted Thiazolidine-2-thiones" Synlett Jun. 2010 (2010): pp. 973-975; with attached Supporting Information pp. 1-40.

CAS Registry Number Compounds excerpted from JMM1 STN SRNTS Aug. 9, 2017; pp. 1-4.

Ito, N., "A Medium-Term Rat Liver Bioassay for Rapid Vivo Detection of Carcinogenic Potential of Chemicals" Cancer Science 94.1 (2003); pp. 3-8.

Hozien, Zeinab A.: "Intramolecular Mannich reaction for synthesis of imidazo-[2,1-b]-1,3,5-thiadiazines and 1,2,4-trlazino[3,2,-b]-1,3,5-thiadiazines", Journal of Chemical Research, Synopses , (3), 99, 401-416 CODEN: URPSDC; ISSN: 0308-2342, 2000, XP002743094, DOI: 10.3184/030823400103166607 10.3184/030823400103166607.

Kinugawa, Jiro et al: "Fungicides VIII. Synthesis and antifungal activity of some thiocyanatolmidazoles, thlocyanatotriazoles, and 1-(4-thlocyanatophenyl)pyrazoles", Chemical & Pharmaceutical Bulletin , 12(4), 433-40 CODEN: CPBTAL; ISSN: 0009-2363, 1964, XP002743095, DOI: 10.1248/CP B.12.433 10.1248/CP8.12.433.

Harii N et al: "Thyrocytes express a functional toll-like receptor 3: Over expressin can be induced by viral Infection and reversed by phenylmethimazole and is associated with Hashimoto's autoimmune thyroiditis", Molecular Endocrinology, The Endocrine Society, US, vol. 19, No. 5, Jan. 20, 2005 (Jan. 20, 2005), pp. 1231-1250, XP002397372, ISSN: 0888-8809, DOI: 10.1210/ME.2004-0100.

Safaei-Ghomi Javad et al: "The reaction of carbon disulphide with[alpha]-haloketones and primary amines in the presence of potassium lodide as cata", Journal of Chemical Sciences, Springer India, in Co-Publication With Indian Academy of Sciences, India, vol. 125, No. 5, Oct. 19, 2013 (Oct. 19, 2013), pp. 1087.1092, XP035310005, ISSN: 0974-3626, DOI: 10.1007/S12039-013-0482-Y [retrieved on Oct. 19, 2013].

Zsolnai, Tibor: "Antimicrobial activity of potential isothiocyanate formers. V.", Arzneimittel-Forschung , 19 (4), 558-72 CODEN: ARZNAD; ISSN: 0004-4172, 1969.

Database CA [Online] Chemical Abstracts Service, Columbus, Ohio, US; Usui, Yoshiro: "Fungicides . XIX. Syntheses of 3-aminothiazoline-2-thlone and 4H-1,3,4-thiadiazine derivatives", retrieved from STN Database accession No. 1969:461352.

International Search Report and Written Opinion dated Jan. 21, 2015 in reference to International Patent Application No. PCT/US2014/063458 filed Oct. 31, 2014.

International Search Report and Written Opinion dated Oct. 26, 2015 in reference to International Patent Application No. PCT/US2015/029460 filed May 6, 2015.

USPTO Non-Final Office Action dated Aug. 16, 2017 in reference to co-pending U.S. Appl. No. 15/326,821, filed Jan. 17, 2017.

USPTO Restriction Requirement dated Jun. 2, 2017 in reference to co-pending U.S. Appl. No. 15/326,821, filed Jan. 17, 2017.

International Search Report and Written Opinion dated Jul. 22, 2015 in reference to International Patent Application No. PCT/US2015/029505 filed May 6, 2015.

International Search Report and Written Opinion dated Feb. 23, 2016 in reference to International Patent Application No. PCT/US2015/029487 filed May 6, 2015.

Theoclitou, et al.; "Rapid Parallel Synthesis of Combinatorial Libraries of Substituted 3-Thio-1,2,4-triazoles and 2-Thioimidazoles"; J. Comb. Chem. 2002, 4, pp. 315-319.

(56) References Cited

OTHER PUBLICATIONS

Luscinskas, F.W., et al., 1996. Endothelial-dependent mechanisms in chronic inflammatory leukocyte recruitment. Annu. Rev. Med. Vo. 47, pp. 413-421.

Panes et al. 1999. Leukocyte-Endothelial Cell Adhesion: Avenues for Therapeutic Intervention. British Journal of Pharmacology, vol. 126, pp. 537-550.

Bevilacqua, M. P. 1991 Endothelial-Leukocyte Adhesion Molecules. Annu. Rev. Immunol. 11 :767-804.

Schindler, U., et al. 1994. Three NF-kappa B Binding Sites in the Human E-Selectin Gene Required for Maximal Tumor Necrosis Factor Alpha-Induced Expression. Molecular and Cellular Bioilogy, vol. 14, No. 9, pp. 5820-5831. American Society of Microbilogy.

Neish et al. 1992. Functional Analysis of the Human Vascular Cell Adhesion Molecule 1 Promoter. J Exp. Med., vol. 176, pp. 1583-1593, The Rockefeller University Press.

Neish et al. 1995. Sp1 is a Component of the Cytokine-Inducible Enhancer in the Promoter of Vascular Cell Adhesion Molecule-1. The Journal of Biological Chemistry, vol. 270, pp. 28903-28909.

Neish et al. 1995. Endothelial Interferon Regulatory Factor 1 Cooperates With NF-Kappa B as a Transcriptional Activator of Vascular Cell Adhesion Molecule, Molecular and Cellular Biology, May 1995, pp. 2258-2569, vol. 15, No. 5, American Society of Microbilogy.

Ledebur et al. 1995. Transcriptional Regulation of the Intercellular Adhesion Molecule-1 Gene by Inflammatory Cytokines in Human Endothelial Cells. Essential Roles of a Variant NF-Kappa B Site and P65 Homodimers. Journal of Biological Chemistry, vol. 270, pp. 933-943, vol. 270. The American Society of Biochemistry and Molecular Biology, Inc., USA.

Munoz et al. 1996. Transcriptional Up-Regulation of Intracellular Adhesion Molecule-1 in Human Endothelial Cells by the Antioxidant Pyrrolidine Dithiocarbamate Involves the Activation of Activating Protein-1. The Journal of Immunology, vol. 157, pp. 3587-3597, The American Association of Immunologists.

May et al. 1998. Signal Transduction Through NF-Kappa B. Immunology Today vol. 19, pp. 80-88, Elsevier Science Ltd.

Pierce et al. 1996. Salicylates Inhibit I Kappa B-Alpha Phosphorylation, Endothelial-Leukocyte Adhesion Molecule Expression, and Neutrophil Transmigration. Journal of Immunology, vol. 156, pp. 3961-3969.

Pierce et al. 1997. Novel Inhibitors of Cytokine-Induced Ikba Phosphorylation and Endothelial Cell Adhesion Molecule Expression Show Anti-Inflammatory Effects In Vivo. Journal of Biological Chemistry, vol. 272, pp. 21096-21103.

Umetani et al. 2000. A Novel Cell Adhesion Inhibitor, K-7174, Reduces the Endothelial VCAM-1 Induction by Inflammatory Cytokines, Acting Through the Regulation of GAT A. Biochemical and Biophysical Research Communications, vol. 272, pp. 370-374, Academic Press.

Dagia et al. 2003. A Proteasome Inhibitor Reduces Concurrent, Sequential and Long Term IL-1.Beta. and TNF-.Alpha. Induced Endothelial Cell Adhesion Molecule Expression and Adhesion. Am. J. Phys. Cell Physiol., pp. C813-C822, The American Physiological Society.

Carlos et al. 1991. Human Monocytes Bind to Two Cytokine-Induced Adhesive Ligands on Cultured Human Endothelial Cells: Endothelial-Leukocyte Adhesion Molecule-1 and Vascular Cell Adhesion Molecule-1. Blood, vol. 77, pp. 2266-2271, The American Society of Hematology.

Alon et al. 1994. Distinct Cell Surface Ligands Mediate T Lymphocyte Attachment and Rolling on P and E-Selectin Under Physiological Flow. The Journal of Cell Biology, vol. 127, pp. 1485-1495.

Alon et al. 1995. The Integrin VLA-4 Supports Tethering and Rolling in Flow on VCAM-1. The Journal of Cell Biology. vol. 128, pp. 1243-1253, The Rockefeller University Press.

Ochi et al. 2002. Hyperosmotic Stimuli Inhibit VCAM-1 Expression in Cultured Endothelial Cells Via Effects on Interferon Regulatory Factor-1 Expression and Activity, Eur. J. Immunol., vol. 32, pp. 1821-1831, Wiley-VCH Verlag GmbH, Weinheim, Germany.

Ahmad et al. 1998. Role of Activating Protein-1 In the Regulation of the Vascular Cell Adhesion Molecule-1 Gene Expression by Tumor Necrosis Factor-Alpha. Journal of Biological Chemistry, vol. 273, pp. 4616-4621.

Umetani et al. 2001. Function of GAT A Transcription Factors in Induction of Endothelial Vascular Cell Adhesion Molecule-1 by Tumor Necrosis Factor-Alpha. Arterioscler Thromb. Basc. Biol., pp. 917-922.

Kjellin et al. 1969. Tautomeric Cyclic Thiones. Part III. Preparation of N- and S-Methyl Derivatives of Some Azoline-2-Thiones. Acta Chemica Scandanavica 23: 2879-2887.

Calvey et al., J. Invest. Surg. (Mar.-Apr. 2007), 20(2), pp. 71-85.

Carlos, T. M., and J. M. Harlan. 1994. Leukocyte-Endothelial Adhesion Molecules. Blood 84:2068-2101.

Springer, T. A. 1994. Traffic Signals for Lymphocyte Recirculation and Leukocyte Emigration: The Multistep Paradigm Cell 76:301-314.

Dagia, N. M., N. Harii, A. E. Meli, X. Sun, C. J. Lewis, L. D. Kohn, and D. J. Goetz. 2004. Phenyl Methimazole Inhibits Tnfa-Induced VCAM-I Expression in an IFN Regulatory Factor-I-Dependent Manner and Reduces Monocytic Cell Adhesion to Endothelial Cells—J Immunol 173:2041-2049.

Yamamoto, M., S. Sato, K. Mori, K. Hoshino, O. Takeuchi, K. Takeda, and S. Akira. 2002. Cutting Edge: A Novel Tolvil-1 Receptor Domain-Containing Adapter That Preferentially Activates the IFN-Beta Promoter in the Toll-Like Receptor Signaling. J Immunol 169: 6668-6672.

Moutaery, Ahmed Al, Methimazole Prevents Stress and Chemical Induced Gastropathy in Rats, Exp Toxic Pathol. 2003, 55: pp. 277-285; http://www.elsevier-deutschland.de.

Gantner, et al., Collaborative Induction of Inflammatory Responses by Dectin-1 and Toll-Like Receptor 2, The Journal of Experimental Medicine, 2003, vol. 197, No. 9, pp. 1107-1117, USA.

Jones, et al., Differential Roles of Toll-Like Receptors in the Elicitation of Proinflammatory Responses by Macrophages, Ann Rheum Dis 2001, vol. 60, pp. iii6-iii12, Boston, MA, USA.

Devendra, et al., Interferon Alpha-A Potential Link in the Pathogenesis of Viral-Induced Type 1 Diabetes and Autoimmunity, Clinical Immunology, 2004, pp. 225-233, vol. 111, Elsevier, USA.

Mozes, et al., Spontaneous Autoimmune Disease in (NZB X NZW)F1 Mice is Ameliorated by Treatment with Methimazole, Journal of Clinical Immunology, 1998, pp. 106-113, vol. 18, No. 2, Plenum Publishing Company, New York, USA.

Luscinskas, et al., Monocyte Rolling, Arrest and Spreading on IL-4-Activated Vascular Endothelium Under Flow is Mediated via Sequential Action of L-Selectin, B1-Integrins, and B2-Integrins, The Journal of Cell Biology, 1994, pp. 1417-1427, vol. 125, No. 6, The Rockefeller University Press, New York, USA.

Napolitano, et al., High Glucose Levels Increase Major Histocompatibility Complex Class I Gene Expression in Thyroid Cells and Amplify Interferon-y Action, Endocrinology, 2002, pp. 1008-1017, vol. 143, No. 3, USA.

Hemmi, et al., Small Anti-Viral Compounds Activate Immune Cells via the TLR7 MyD88-Dependent Signaling Pathway, Department of Host Defense Research Institute for Microbial, Osaka University, 2002, pp. 196-200, vol. 3, No. 2, Nature Publishing Group, California, USA.

Oshiumi, et al., TIR-Containing Adapter Molecule (TICAM)-2, A Bridging Adapter Recruiting to Toll-Like Receptor 4 TICAM-1 That Induces Interferon-B, The Journal of Biological Chemistry by the American Society for Biochemistry and Molecular Biology, Inc., 2003, pp. 49751-49762, vol. 278, No. 50, http://www.jbc.org, USA.

Ishii, et al., Genomic DNA Released by Dying Cells Induces the Maturation of APCs1,2, Nature Immunology, 2001, pp. 2602-2607, vol. 167, The American Association of Immunologists, USA.

Suzuki, et al., Transfection of Single-Stranded Hepatitis A Virus RNA Activates MHC Class I Pathway, Clinical Exp. Immunology, 2002, pp. 234-242, vol. 127, Blackwell Science, Oxford, United Kindgom.

Eader, et al., Induction of Multiple Cytokine Gene Expression and IRF-1 mRNA by Flavone Acetic Acid in a Murine Macrophage Cell Line1, Cellular Immunology, 1994, pp. 211-222, vol. 157, Academic Press, Inc., Waltham, Massachusetts, USA.

(56) References Cited

OTHER PUBLICATIONS

Delgado, et al., Vasoactive Intestinal Peptide and Pituitary Adenylate Cyclase-Activating Polypeptide Prevent Inducible Nitric Oxide Synthase Transcription in Macrophages by Inhibiting NF-kB and IFN Regulatory Factor 1 Activation, The Journal of Immunology, 1999, pp. 4685-4696, vol. 162, The American Association of Immunologists, USA.

Fujimoto, et al., A Role for iNOS in Fasting Hyperglycemia and Impaired Insulin Signaling in the Liver of Obese Diabetic Mice, Diabetes, 2005, pp. 1340-1348, vol. 54, The American Diabetes Association, USA.

Servant, et al., Overlapping and Distinct Mechanisms Regulating IRF-3 and IRF-7 Function, Journal of Interferon and Cytokine Research, 2002, pp. 49-58, vol. 22, Mary Ann Liebert, Inc., New York, USA.

Horwitz, et al., Diabetes Induced by Coxsackie Virus: Initiation by Bystander Damage and Not Molecular Mimicry, Nature Medicine, 1998, pp. 781-785, vol. 4, No. 7, Nature Publishing Group, California, USA.

Yamamoto, et al., Essential Role for TIRAP in Activation of the Signalling Cascade Shared by TLR2 and TLR4, Nature, 2002, www.nature.com/nature, pp. 324-329, vol. 420, Nature Publishing Group, California, USA.

McCartney-Francis, et al., Dysregulation of IFN-y Signaling Pathways in the Absence of TGF-b1, The Journal of Immunology, 2002, pp. 5941-5947, vol. 169, http://jimmunol.org, The American Association of Immunologists, Inc., USA.

Kamijo, et al., Requirement for Transcription Factor IRF-1 in NO Synthase Induction in Macrophages, Science, 1994, pp. 1612-1615, vol. 263, Journal Storage, USA.

Pine, et al., Tyrosine Phosphorylated p91 Binds to a Single Element in the ISGF2/IRF-1 Promoter to Mediate Induction by IFNx and IFNy, and is Likely to Autoregulate the p91, The EMBO Journal, 1994, pp. 158-167, vol. 13, No. 1, Oxford University Press, New York, USA.

Nakazawa, et al., Complete Suppression of Insulitis and Diabetes in NOD Mice Lacking Interferon Regulatory Factor-1, Journal of Autoimmunity, 2001, pp. 119-125, vol. 17, Academic Press, Inc., Waltham, Massachusetts, USA.

Li, et al., Role of p38x Map Kinase in Type I Interferon Signaling, The Journal of Biological Chemistry, 2004, pp. 970-979, vol. 279, No. 2, The American Society of Biochemistry and Molecular Biology, Inc., Rockville, Maryland, USA.

Ohmori, et al., Synergy Between Interferon-y and Tumor Necrosis Factor-x in Transcriptional Activation is Mediated by cooperation Between Signal Transducer and Activator of Transcription 1 and Nuclear Factor kB, The Journal of Biological Chemistry, 1997, pp. 14899-14907, vol. 23, The American Society of Biochemistry and Molecular Biology, Inc., Rockville, Maryland, USA.

Jiang, et al., Toll-Like Receptor 3-Mediated Activation of Nf-kB and IRF3 Diverges at Toll-IL-1 Receptor Domain-Containing Adapter Inducing IFN-b, Proceedings of the National Academy of Sciences, 2004, pp. 3533-3538, vol. 101, No. 10, The National Academy of Sciences of the USA.

Kohn, et al., Toll-Like Receptors in Nonimmune Cells and Environmental Induction of the Pathologic Expression of Innate Immunity and Autoimmune Inflammatory Diseases: A New Therapeutic Opportunity, Research Ohio, 2005, pp. 1-23, vol. 15, A joint publication of Ohio University College of Osteopathic Medicine and the Ohio Osteopathic Foundation, Ohio, USA.

Mundschau, et al., Platelet-Derived Growth Factor Signal Transduction Through the Interferon-Inducible Kinase PKR, The Journal of Biological Chemistry, 1995, pp. 3100-3106, vol. 270, No. 7, The American Society for Biochemistry and Molecular Biology, Inc., Rockville, Maryland, USA.

Ivanovic, et al., Acute-Phase Protein Expression in DMSO-Intoxicated Rats, Toxicology Letters, 2004, pp. 153-159, Elsevier Ireland Ltd., Ireland.

Kirchhoff, et al., NFkB Activation is Required for Interferon Regulatory Factor-1-Mediated Interferon B Induction, European Biochemical Societies, 1999, pp. 546-554, vol. 26, Blackwell Publishing Ltd., Oxford, United Kingdom.

Jones, Reuben G., Studies on Imidazole Compounds. I. A Synthesis of Imidazoles with Functional Groups in the 2-Position, J. Am. Chem. So., Feb. 1949, vol. 71, pp. 383-386.

Office Action dated Jul. 16, 2018 pertaining to U.S. Appl. No. 15/326,782.

USPTO Non-Final Office Action dated Feb. 9, 2018 in reference to co-pending U.S. Appl. No. 15/326,782, filed Jan. 17, 2017.

USPTO Restriction Requirement dated Dec. 4, 2017 in reference to co-pending U.S. Appl. No. 15/326,782, filed Jan. 17, 2017.

USPTO Notice of Allowance dated Feb. 5, 2018 in reference to co-pending U.S. Appl. No. 15/326,821, filed Jan. 17, 2017.

\* cited by examiner

PREVENTION AND TREATMENT OF NON-ALCOHOLIC FATTY LIVER DISEASE

CROSS REFERENCE TO RELATED APPLICATIONS

This application claims the benefit under 35 U.S.C. § 119 of U.S. Provisional Patent Application No. 62/026,164, filed Jul. 18, 2014, entitled, "Prevention and Treatment of Non-Alcoholic Fatty Liver Disease", and of U.S. Provisional Patent Application No. 62/026,197, filed on Jul. 18, 2014, entitled, "Methods and Compositions to Modify GSK-3 Activity", and of U.S. Provisional Patent Application No. 62/026,234, filed Jul. 18, 2014, entitled, "Imidazole and Thiazole Compositions for Modifying Biological Signaling", the contents of which are hereby incorporated by reference in their entirety.

TECHNICAL FIELD

The present disclosure relates generally to the prevention and treatment of non-alcoholic fatty liver disease (hereinafter, "NAFLD"). More particularly, the present disclosure relates to one or more of methods for preventing NAFLD, methods of treating NAFLD, and pharmaceutical compositions for the prevention and/or treatment of NAFLD.

BACKGROUND

NAFLD is a form of fat-induced inflammation of the liver which is present throughout the industrialized world. The prevalence of NAFLD ranges from 10% to 24% in the general population and NAFLD is the leading cause of cirrhosis, chronic liver failure, liver transplantation, and primary hepatic cancers in the United States. NAFLD is associated with metabolic syndrome (e.g., obesity, diabetes mellitus, hyperlipidemia, and/or hypertension), certain medications (e.g., estrogens, coumadin, tamoxifen, valproic acid, methotrexate, isoniazid, corticosteroids, Vitamin A, troglitazone, I-Asparaginase, amiodarone, perhexiline, calcium channel blockers, and/or nucleoside analogues), Hepatitis C, nutritional risk factors (e.g., rapid weight loss, total parenteral nutrition, starvation, and/or protein-calorie malnutrition), certain surgical procedures (e.g., gastrointestinal surgery for obesity and/or extensive small-bowel resection), metabolic disorders (e.g., cystic fibrosis and/or abetalipoproteinemia), syndromes associated with obesity and insulin resistance (e.g., lipodystrophies, hypopituitarism, and/or Prader-Willi syndrome), and various other conditions. With particular regard to obesity (a feature of metabolic syndrome), NAFLD is observed in up 75% of obese persons.

While there are medications approved for treating diseases and conditions associated with NAFLD, there are currently no medications specifically approved for the treatment of NAFLD itself. As a result, treatment protocols are focused upon the associated conditions, such as metabolic syndrome. For example, conventional treatment of NAFLD may include weight loss, restricting dietary fat, administration of medications employed in the treatment of an associated condition (e.g., metformin and thiazolidinediones), and administration of medications employed in the treatment of hyperlipidemia (e.g., HMG-Co-A inhibitors). However, in addition to there being no standard treatment specific to NAFLD, many medications employed to treat conditions associated with NAFLD are hepatotoxic.

SUMMARY

Provided herein is an entirely new paradigm for disease intervention. In some embodiments, provided are methods for treating NAFLD in a subject in need thereof. Such methods include administering to the subject a therapeutically effective amount of at least one compound of General Formula (I) or (II):

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In some embodiments, also provided are methods for preventing or otherwise reducing the risk of developing NAFLD in a subject in need thereof. Such methods include administering to the subject a therapeutically effective amount of at least one compound of General Formula (I) or (II):

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In some embodiments, also provided are methods for inhibiting excessive accumulation of fat in liver tissue. Such methods include contacting the liver tissue with a therapeutically effective amount of at least one compound of General Formula (I) or (II):

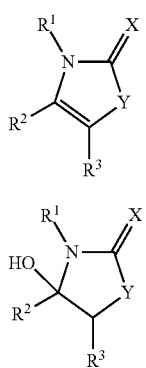

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In yet other embodiments, provided are pharmaceutical compositions for the prevention and/or treatment of NAFLD. Such anti-NAFLD agents include (1) a therapeutically effective amount of one or more of metformin, thiazolidinediones, or HMG-Co-A inhibitors; and (2) a therapeutically effective amount of at least one compound of General Formula (I) or (II):

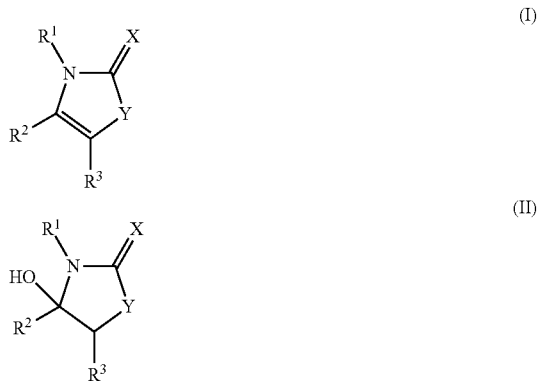

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
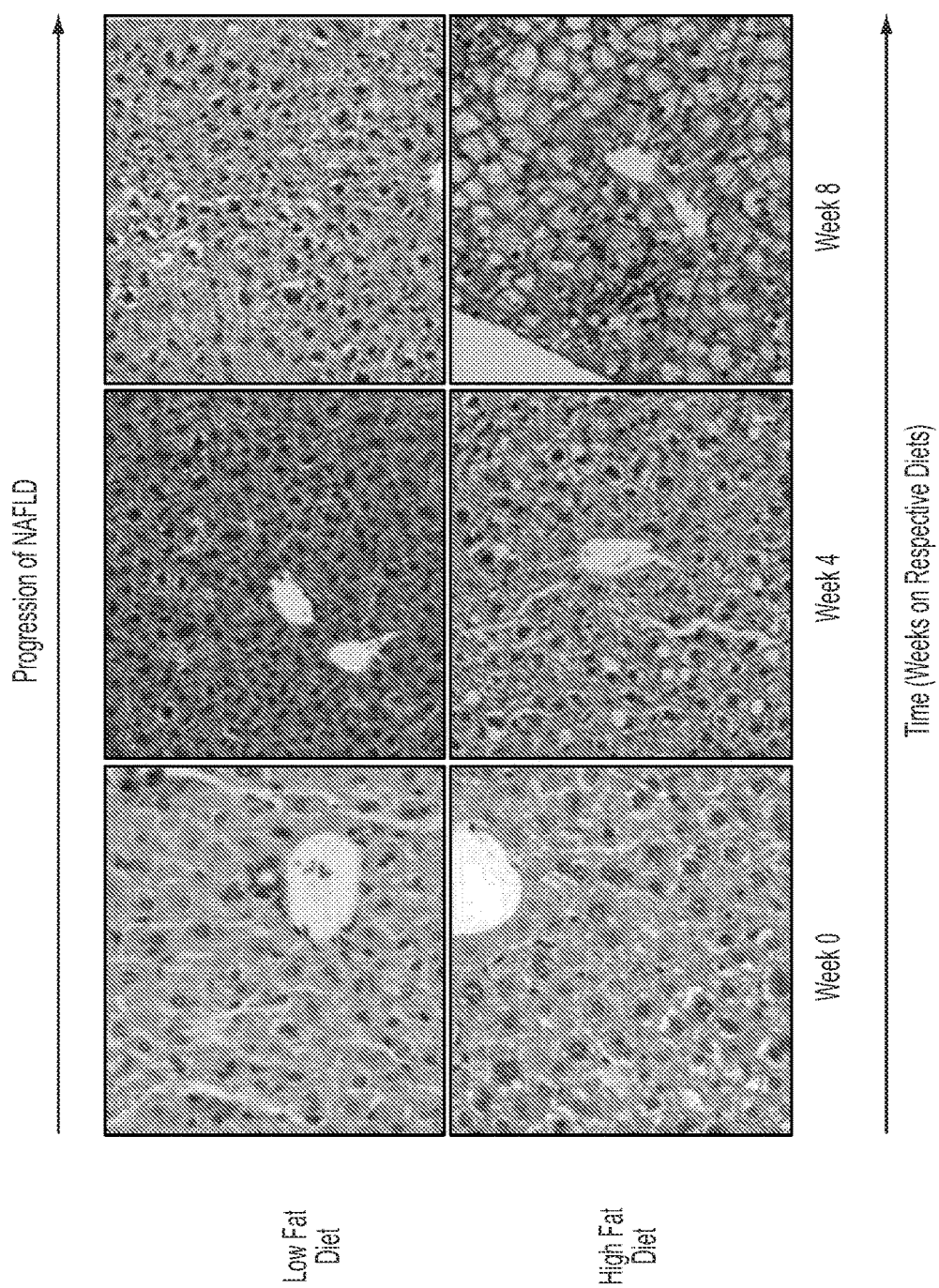
FIG. 1 is a micrograph of liver tissue harvested from representative C57BL/6J mice on a low fat diet (i.e., LFD) and C57BL/6J mice on a high fat diet (i.e., HFD) at 0 weeks, 4 weeks, and 8 weeks.

While the following terms are believed to be well understood by one of ordinary skill in the art, definitions are set forth to facilitate explanation of the presently-disclosed subject matter.

The terms "prevent," "prevention," and "preventing," as used herein, refer to prophylactically avoiding and/or prolonging the development or acquisition of a disease, disorder, or symptom thereof. The terms "prevent," "prevention," and "preventing", as used herein, may also refer to reducing the risk of developing and/or acquiring a disease, disorder, or symptom thereof.

The terms "treat," "treatment," and "treating," as used herein, refer to delaying acquisition, inhibiting development or progression of, stabilizing, and/or causing regression of a disease, disorder, and/or symptom thereof.

The terms "non-alcoholic fatty liver disease" and "NAFLD" as used herein, refer to a chronic disease or disorder wherein excessive fat (e.g., triglycerides and/or free fatty acids) accumulates in a liver cell, liver tissue (e.g., a lobe of the liver), and/or the liver of subjects who drink little or no alcohol. Excessive fat may accumulate in a liver cell, liver tissue, and/or the liver of subjects via steatosis, which may trigger inflammatory processes therein. NAFLD includes a spectrum of stages, generally including: steatosis, non-alcoholic steatohepatitis (hereinafter, "NASH"), fibrosis, and cirrhosis. The spectrum of stages increase in severity from steatosis to NASH to fibrosis to cirrhosis.

The term "steatosis" as used herein, refers to a stage of NAFLD involving the process of abnormal retention or accumulation of fat within a liver cell, liver tissue (e.g., a lobe of the liver), and/or the liver. During steatosis, a liver cell accumulates fat vacuoles (e.g., liposomes) around the nucleus. In an early stage of steatosis, a liver cell may accumulate multiple fat vacuoles which do not displace the nucleus (i.e., microvesicular fatty change). However, in a later stage of steatosis, the accumulated fat vacuoles may increase in size, causing displacement of the nucleus toward the periphery of the liver cell (i.e., macrovesicular fatty change). Steatosis is the first stage of NAFLD.

The terms "non-alcoholic steatohepatitis" and "NASH" as used herein, refer to a stage of NAFLD involving abnormal retention or accumulation of fat within a liver cell, liver tissue (e.g., a lobe of the liver), and/or the liver accompanied by lymphocytic migration into the liver, resulting in inflammation thereof. NASH is the second stage of NAFLD.

The term "fibrosis" as used herein, refers to a later stage of NAFLD wherein liver cell death and inflammation trigger stellate cell formation and excess fibrous connective tissue formation within liver tissue (e.g., a lobe of the liver), the liver, hepatic sinusoids and/or veins. Fibrosis may lead to cirrhosis of the liver. Fibrosis is the third stage of NAFLD.

The term "cirrhosis" as used herein, refers to a stage of NAFLD involving replacement of liver tissue by fibrosis, scar tissue, and/or regenerative hepatic nodules, leading to the loss of function of liver tissue and/or the liver. Cirrhosis may lead to liver failure, coma, and/or death of the subject. Cirrhosis is the fourth stage of NAFLD.

Depending upon the context of use, the term "subject in need thereof" as used herein, refers to a subject at risk for developing NAFLD, a subject exhibiting symptoms associated with NAFLD, and/or a subject having NAFLD. One example of a subject at risk for developing NAFLD includes, but should not be limited to, a subject having a disease or disorder associated with NAFLD. Examples of diseases or disorders associated with NAFLD include, but should not be limited to, a subject having features of metabolic syndrome (e.g., obesity, diabetes mellitus, hyperlipidemia, and/or hypertension); a subject taking certain medications (e.g., estrogens, coumadin, tamoxifen, valproic acid, methotrexate, isoniazid, corticosteroids, Vitamin A, troglitazone, I-Asparaginase, amiodarone, perhexiline, calcium channel blockers, and/or nucleoside analogues); a subject having Hepatitis C; a subject having elevated liver enzymes and/or abnormal liver function tests; a subject having certain nutritional risk factors (e.g., rapid weight loss, total parenteral nutrition, starvation, and/or protein-calorie malnutrition); a subject having undergone certain surgical procedures (e.g., gastrointestinal surgery for obesity and/or extensive small-bowel resection); a subject having a metabolic disorder (e.g., cystic fibrosis and/or abetalipoproteinemia); a subject having a syndrome associated with obesity and/or insulin resistance (e.g., lipodystrophies, hypopituitarism, and/or Prader-Willi syndrome); and a subject having various other disorders (e.g., inflammatory bowel disease, small-bowel diverticulosis, viral infection, and/or exposure to petrochemicals and/or toxic mushrooms). Examples of symptoms associated with NAFLD include, but should not be limited to, fatigue, pain in the upper right abdomen, and weight loss. With regard to a subject having NAFLD, diagnosis of NAFLD may be performed using standard diagnostic testing techniques for NAFLD, such as are known to those of ordinary skill in the art. Examples of standard diagnostic testing techniques for NAFLD include, but should not be limited to, molecular determinations including blood tests (e.g., liver function tests including tests of liver enzymes and/or triglyceride quantification); microscopic determinations including imaging procedures (e.g., ultrasound, computerized tomography scan and/or magnetic resonance imaging); and microscopic determinations including liver tissue testing (e.g., liver biopsy), such as are known to those of ordinary skill in the art. In some embodiments, NAFLD may be visualized macroscopically via the naked eye.

The term "therapeutically effective amount" as used herein, refers to an amount necessary or sufficient to realize a desired biologic effect. The therapeutically effective amount may vary depending on a variety of factors known to those of ordinary skill in the art, including but not limited to, the particular composition being administered, the activity of the composition being administered, the size of the subject, the sex of the subject, the age of the subject, the general health of the subject, the timing and route of administration, the rate of excretion, the administration of additional medications, and/or the severity of the disease or disorder being prevented and/or treated. In some embodiments, the term therapeutically effective amount refers to the amount of imidazole and/or thiazole compounds and, more specifically, imidazole 2-thiones, imidazole 2-ones, thiazole 2-thiones, and/or thiazole 2-ones, necessary or sufficient to prevent NAFLD or treat NAFLD. More specifically, in embodiments, the term therapeutically effective amount refers to the amount of imidazole and/or thiazole compounds and, more specifically, imidazole 2-thiones, imidazole 2-ones, thiazole 2-thiones, and/or thiazole 2-ones, necessary or sufficient, to prevent excessive accumulation of fat in a liver cell, liver tissue, and/or the liver, and/or to reduce fat content in liver tissue of the subject relative to a baseline level.

The term "excessive accumulation of fat" as used herein, refers to an amount of fat accumulation in a liver cell, liver tissue, and/or the liver which is greater than an amount of fat accumulation in a normal liver cell, liver tissue, and/or the liver in a subject who is not in need of treatment for NAFLD (i.e., a normal level). The determination of an excessive accumulation of fat may be accomplished via standard diagnostic testing techniques for NAFLD, as previously described. More specifically, in some embodiments, the determination of an excessive accumulation of fat may be accomplished via molecular determinations and/or microscopic determinations wherein an amount of fat in a liver cell, liver tissue (e.g., a lobe of the liver), and/or the liver of a subject is assessed (such as, e.g., visually and/or quantifiably) as being greater than an amount of fat in a normal liver cell, liver tissue, and/or the liver of a subject who is not in need of treatment for NAFLD (i.e., a control or reference subject). In some embodiments, a sample of the liver cell, liver tissue, and/or the liver of the subject to be assessed (i.e., a biological sample) and a sample of the liver cell, liver tissue, and/or the liver of the control subject (i.e., a control sample) are provided for the determination of an excessive accumulation of fat.

The terms "fat" and "fat content" as used herein, respectively refer to triglycerides, free fatty acids, vacuoles of triglycerides and/or vacuoles of free fatty acids which accumulate in a liver cell, liver tissue, and/or the liver.

The term "baseline level" as used herein, refers to a level of fat content in a liver cell, liver tissue, and/or the liver in a subject prior to administration of imidazole and/or thiazole compounds and/or other medications for preventing and/or treating NAFLD. The baseline level may be determined via molecular determinations and/or microscopic determinations (such as, e.g., visual and/or quantifiable determinations).

The term "normal level" as used herein, refers to a level of fat content in a normal liver cell, liver tissue (e.g., a lobe of the liver), and/or the liver from a subject (i.e., a control subject) who is not in need of treatment for NAFLD. The normal level allows distinguishability between subjects suffering from a disease or disorder and subjects not suffering from a disease or disorder, e.g., NAFLD.

The terms "inhibit", "inhibition", and "inhibiting" refer to preventing excessive accumulation of fat in a liver cell, liver tissue, and/or the liver and/or to reducing fat content in a liver cell, liver tissue (e.g., a lobe of the liver), and/or the liver to at or below a normal level. For example, excessive accumulation of fat in liver tissue is inhibited when accumulation of fat is prevented above a normal level therein.

Additionally, as a further example, excessive accumulation of fat in liver tissue is also inhibited when accumulation of fat is reduced to at or below a normal level.

The term "pharmaceutically acceptable" as used herein, refers to a pharmaceutically active agent and/or other agents/ingredients for use in a pharmaceutical composition which are not deleterious to a subject receiving the pharmaceutical composition and/or which are suitable for use in contact with the tissues of humans and lower animals without undue toxicity, irritation, allergic response, and the like commensurate with a reasonable benefit/risk ratio.

The term "pharmaceutical carrier" as used herein, refers to a solid or liquid filler, diluent or encapsulating substance. These materials are well known to those skilled in the pharmaceutical arts. Some examples of the substances that can serve as pharmaceutical carriers include sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants, such as sodium lauryl sulfate, as well as coloring agents, flavoring agents, tableting agents, and preservatives, can also be present. Formulation of the components into pharmaceutical compositions is done using conventional techniques The term "administration" as used herein, refers to systemic use, such as by injection (e.g., parenterally), intravenous infusion, suppositories and oral administration thereof, and/or to topical use of the imidazole and/or thiazole compounds and, more specifically, imidazole 2-thiones, imidazole 2-ones, thiazole 2-thiones, and/or thiazole 2-ones, and pharmaceutical compositions including the same.

The term "compatible" as used herein, refers to components for use in a pharmaceutical composition which are capable of being comingled without interacting in a manner which would substantially decrease the efficacy of the pharmaceutically active agent under ordinary use conditions.

The terms "imidazole compounds" and/or "thiazole compounds", as used herein, refer to and/or are limited to the compositions having the following general structural formulae:

(I)

(II)

or pharmaceutically-acceptable salts or solvates thereof.

In the imidazole compounds and thiazole compounds having general structural formulae (I) and (II): $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH, with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; or (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In the compounds of General Formula (I) and General Formula (II), group $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof. In illustrative non-limiting embodiments, group $R^1$ is chosen from methyl, ethyl, propyl, butyl, pentyl, hexyl, 2-propenyl,

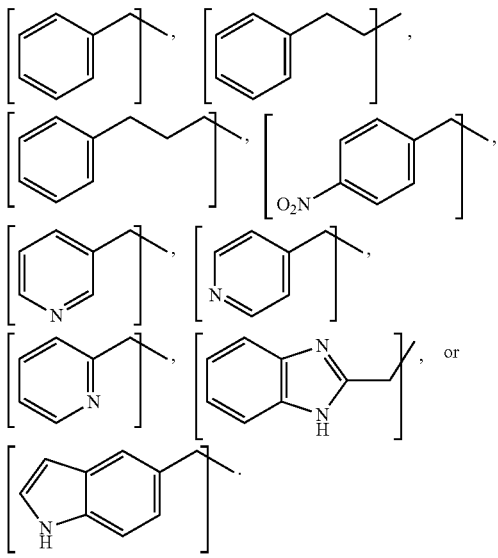

In other illustrative embodiments, group $R^1$ may have be a group $Q^1$:

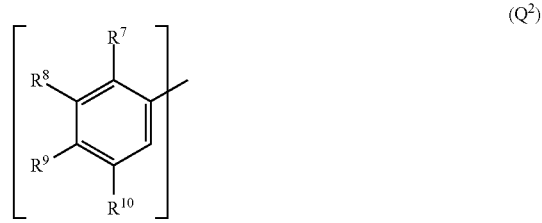

in which groups $R^4$, $R^5$, and $R^6$ are independently chosen from —H, halo (such as —F, —Cl, or —Br), —NO$_2$, —CN, or alkylesters such as —OCH$_3$. In other illustrative embodiments, group $R^1$ may be a group $Q^1$, in which groups $R^4$ and $R^5$ all are H and group $R^6$ is chosen from alkylesters, Cl, —NO$_2$, or —CN.

In the compounds of General Formula (I) and General Formula (II), group $R^2$ is chosen from unsubstituted aryl groups, substituted aryl groups, heteroaryl groups, substituted heteroaryl groups, and coumarin. In some embodiments, group $R^2$ may be an unsubstituted phenyl group, a 2-monosubstituted phenyl group, a 3-monosubstituted phenyl group, a 4-monosubstituted phenyl group, a 2,3-disubstituted phenyl group, a 2,4-disubstituted phenyl group, a 2,5-disubstituted phenyl group, a 3,4-disubstituted phenyl group, or a 3,5-disubstituted phenyl group. In such embodiments, group $R^2$ may be a group $Q^2$:

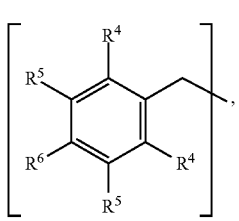

In embodiments in which group $R^2$ is a monosubstituted phenyl group $Q^2$, in group $Q^2$ exactly three of any of $R^7$, $R^8$, $R^9$, and $R^{10}$ are hydrogen, and the one of $R^7$, $R^8$, $R^9$, and $R^{10}$ that is not hydrogen may be chosen from methoxy, ethoxy, hydroxy, trifluoromethoxy, methyl, trifluoromethyl, N-methylamino, (N,N)-dimethylamino, cyano, halo (for example, chloro, fluoro, or bromo), or nitro, for example.

In embodiments in which group $R^2$ is a disubstituted phenyl group $Q^2$, in group $Q^2$ exactly two of any of $R^7$, $R^8$, $R^9$, and $R^{10}$ are hydrogen, and the two groups of $R^7$, $R^8$, $R^9$, and $R^{10}$ that are not hydrogen may be independently chosen from methoxy, ethoxy, hydroxy, trifluoromethoxy, dimethylamino, cyano, chloro, fluoro, or nitro, for example.

In some embodiments in which group $R^2$ is a disubstituted phenyl group $Q^2$, group $Q^2$ may be any isomer of hydroxyphenyl, dihydroxyphenyl, methoxyphenyl, dimethoxyphenyl, halophenyl, dihalophenyl, chlorophenyl, dichlorophenyl, fluorophenyl, halohydroxyphenyl, halomethoxyphenyl, chlorohydroxylphenyl, chloromethoxyphenyl, fluorohydroxyphenyl, fluoromethoxyphenyl.

Illustrative, non-limiting examples of group $R^2$ as a monosubstituted phenyl group $Q^2$ or a disubstituted phenyl group $Q^2$ may include 2-methoxyphenyl; 3-methoxyphenyl; 3-chlorophenyl; 2,5-dimethoxyphenyl; 2,4-dimethoxyphenyl; 3,4-dimethoxyphenyl; 4-(dimethylamino)phenyl; 4-(trifluoromethoxy)phenyl; 4-cyanophenyl; 3-hydroxyphenyl; 2,4-hydroxyphenyl; 3,4-dichlorophenyl; 3-nitrophenyl; 2-hydroxy-5-chlorophenyl; 2-methylphenyl; 2,5-dimethylphenyl; 2-methoxy-5-fluorophenyl; and 2-chloro-5-(trifluoromethyl)phenyl.

In other embodiments, group $R^2$ may be an aryl group such as, for example,

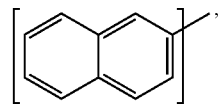

or a substituted derivative thereof. In other embodiments, group R² may be an aryl group other than phenyl. In other embodiments, group R² may be a heteroaryl group such as, for example,

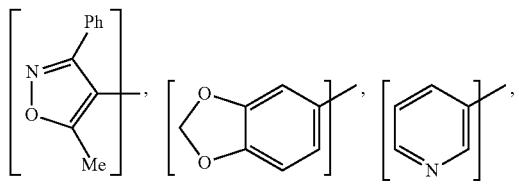

or substituted derivatives of any of these. In other embodiments, group R² may be coumarin, such as, for example,

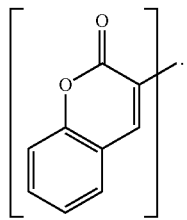

In some embodiments, preferred compounds of General Formula (I) and General Formula (II) may include compounds of formulas

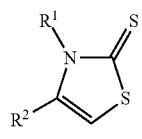 (III)

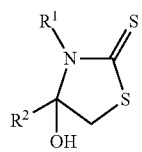 (IV)

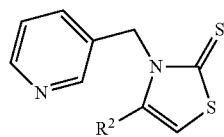 (V)

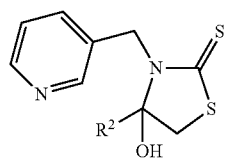 (VI)

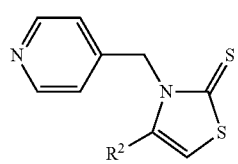 (VII)

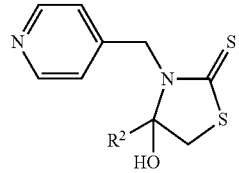 (VIII)

in which groups R¹ and R² are as described above and groups R³ of General Formula (I) and General Formula (II) are hydrogen.

In some embodiments, preferred compounds of General Formula (I) and General Formula (II) may include compounds of formulas (V) or (VI):

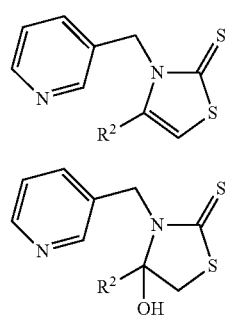

In the compounds of General Formula (I) and General Formula (II), group R³ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof. In non-limiting exemplary embodiments, R³ may be methyl, ethyl, n-propyl, isopropyl, butyl, 3-butenyl, phenyl, or 2-phenylethyl. In some embodiments, R³ is hydrogen. The aliphatic or heteroaliphatic groups of R³ optionally may be bonded to group R² to form a ring. One illustrative example of an aliphatic group R³ bonded to group R² to form a ring is the structure

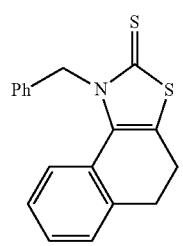

having General Formula (I), in which group R¹ attached to the nitrogen atom is phenylmethyl (benzyl), group R² is phenyl and group R³ is an ethyl group bonded to the 2-position of the phenyl ring of R² to form a six-membered ring including all of group R³ and part of group R².

In the compounds of General Formula (I) and General Formula (II), group X is S or O; and group Y is S or NH. Thus, in some embodiments, group X is S and group Y is S. In other embodiments, group X is S and group Y is NH. In other embodiments, group X is O and group Y is S. In other embodiments, group X is O and group Y is NH.

The compounds of General Formula (I) and General Formula (II) may be prepared using any suitable synthetic scheme. In one exemplary synthetic scheme, the compounds having General Formula (I) or General Formula (II) in which X=O or S and Y=NH may be synthesized by adding an isothiocyanate or isocyanate of formula (1a):

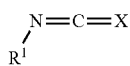
(1a)

(100 mol %, X=O or S) and Et₃N (50 mol %) to an EtOH (0.01 M) solution of a hydrochloride of a methylamino ketone of formula (1b) (100 mol %):

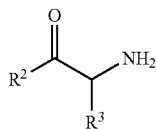
(1b)

to form a reaction mixture. The reaction mixture may be heated at a suitable reaction temperature for a suitable time. If the heating is accomplished using microwave irradiation, the rate of elimination of a hydroxyl group from the product is increased, so as to substantially favor formation of compounds of General Formula (I) over those of General Formula (II). Conversely, application of heat without microwave irradiation favors compounds of General Formula (II) as products. The solvent may be removed, and the product may be isolated by flash chromatography, for example.

Compounds having General Formula (II) in which X=S and Y=S may be synthesized by adding carbon disulfide (CS₂; 150 mol. %) and K₂CO₃ (50 mol. %) to a solution of an amine (150 mol. %) of the formula (2a):

$$R^1-NH_2 \quad (2a)$$

(150 mol. %) in H₂O:EtOH (0.2 M, 1:1) and then adding a 2-bromoketone derivative (100 mol %) of formula (2b):

(2b)

to form a reaction mixture. After stirring, a crude reaction mixture may be extracted with a solvent such as ethyl acetate, and the combined organic layers may be dried and filtered. The solvent may be evaporated by rotary evaporation. The product may be isolated using a solvent such as 10%-20% EtOAc in hexanes. In some cases, some products may precipitate during the reaction. In such cases the product may be isolated by filtration, washed thoroughly with solvent, then dried.

Compounds having General Formula (II), where X=O and Y=S, may be synthesized by adding a solution of carbonyl sulfide (COS; 150 mol. %) and K₂CO₃ (50 mol. %) to a solution of an amine (150 mol. %) of the formula (2a):

$$R^1-NH_2 \quad (2a)$$

in H₂O:EtOH (0.2 M, 1:1) and then adding a 2-bromoketone derivative (100 mol %) of formula (2b):

(2b)

Compounds having General Formula (I), in which X=O or S and Y=S, may be synthesized by dehydrating a compound having General Formula (II) prepared according by any suitable synthetic route, such as the route described above, for example, in which groups $R^1$, $R^2$, $R^3$, X, and Y of the compound having General Formula (II) are the same as those in the desired compound having General Formula (I).

In TABLE 1 below, compounds having General Formula (I) or (II) according to various embodiments are provided, along with exemplary reactants for forming the compound having General Formula (I) or (II) according to the synthetic schemes described above and further described in the Examples section below:

TABLE 1

| Reference | Reactant (1a) or (2a) | Reactant (1b) or (2b) | Compound of General Formula (I) or (II) |
|---|---|---|---|
| COB-117 |  |  | |

TABLE 1-continued

| Reference | Reactant (1a) or (2a) | Reactant (1b) or (2b) | Compound of General Formula (I) or (II) |
|---|---|---|---|
| COB-118 | 2-methoxyphenacylamine | methyl isothiocyanate | 1-methyl-5-(2-methoxyphenyl)-imidazole-2-thione |
| COB-119 | 3-chlorophenacylamine | methyl isothiocyanate | 1-methyl-5-(3-chlorophenyl)-imidazole-2-thione |
| COB-123 | 3,4-dimethoxyphenacylamine | methyl isothiocyanate | 1-methyl-5-(3,4-dimethoxyphenyl)-imidazole-2-thione |
| COB-124 | 3-methoxyphenacylamine | ethyl isocyanate | 1-ethyl-5-(3-methoxyphenyl)-imidazol-2-one |
| COB-125 | 3-chlorophenacylamine | ethyl isocyanate | 1-ethyl-5-(3-chlorophenyl)-imidazole-2-thione |

TABLE 1-continued
| Reference | Reactant (1a) or (2a) | Reactant (1b) or (2b) | Compound of General Formula (I) or (II) |
| --- | --- | --- | --- |
| COB-126 | 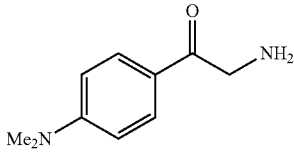 [SMILES: CN(C)c1ccc(C(=O)CN)cc1] | 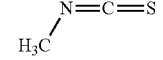 | 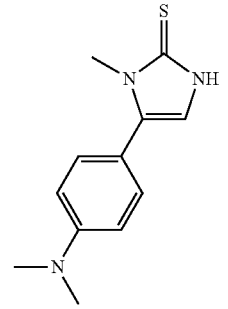 [SMILES: CN(C)c1ccc(-c2c[nH]c(=S)n2C)cc1] |
| COB-128 | 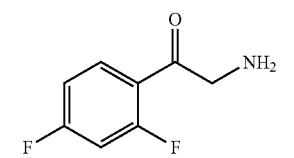 [SMILES: NCC(=O)c1ccc(F)cc1F] | 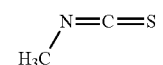 | 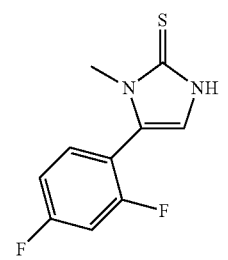 |
| COB-129 | 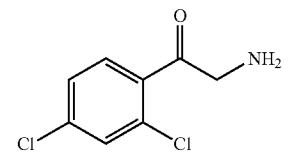 [SMILES: NCC(=O)c1ccc(Cl)cc1Cl] | 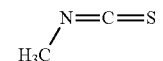 | 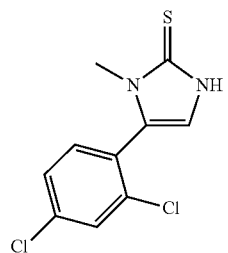 |
| COB-130 | 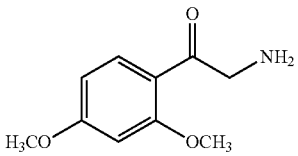 [SMILES: COc1ccc(C(=O)CN)c(OC)c1] | 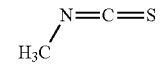 | 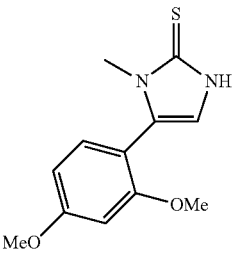 [SMILES: COc1ccc(-c2c[nH]c(=S)n2C)c(OC)c1] |
| COB-132 | 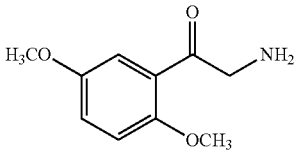 | 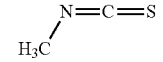 | 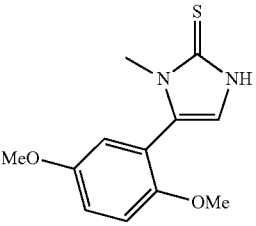 [SMILES: COc1ccc(OC)c(-c2c[nH]c(=S)n2C)c1] |
| COB-133 | 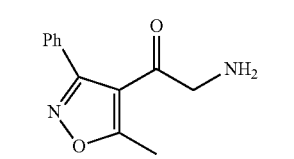 [SMILES: Cc1onc(-c2ccccc2)c1C(=O)CN] | 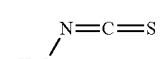 | 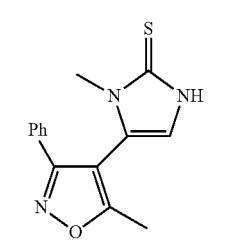 [SMILES: Cc1onc(-c2ccccc2)c1-c1c[nH]c(=S)n1C] |

TABLE 1-continued
| Reference | Reactant (1a) or (2a) | Reactant (1b) or (2b) | Compound of General Formula (I) or (II) |
|---|---|---|---|
| COB-134 | 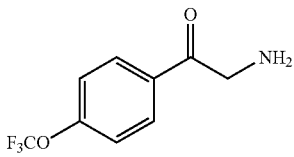 [SMILES: NCC(=O)c1ccc(OC(F)(F)F)cc1] | 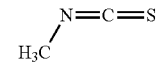 | 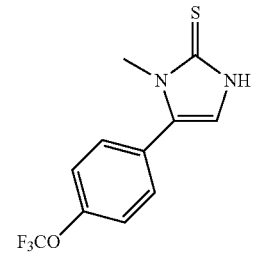 [SMILES: Cn1c(-c2ccc(OC(F)(F)F)cc2)c[nH]c1=S] |
| COB-138 | 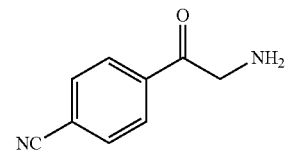 [SMILES: N#Cc1ccc(C(=O)CN)cc1] | 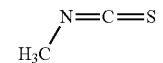 | 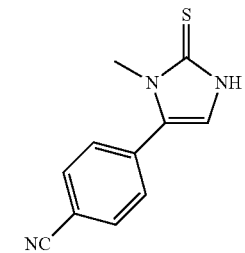 |
| COB-139 | 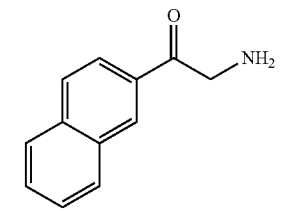 [SMILES: NCC(=O)c1ccc2ccccc2c1] | 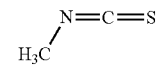 | 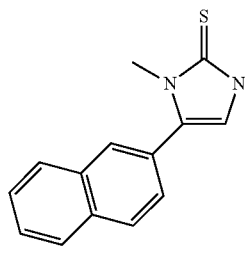 |
| COB-143 | 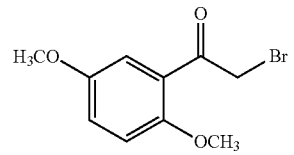 [SMILES: COc1ccc(OC)c(C(=O)CBr)c1] | 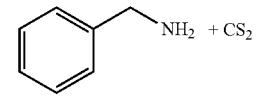 | 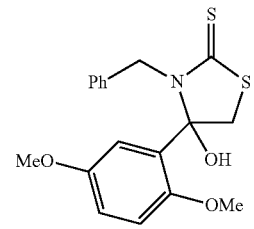 [SMILES: COc1ccc(OC)c(C2(O)CSC(=S)N2Cc2ccccc2)c1] |
| COB-144 | | Dehydration of COB-143 | 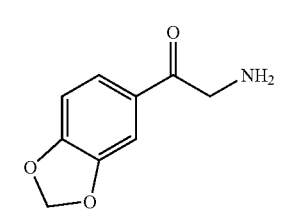 [SMILES: NCC(=O)c1ccc2c(c1)OCO2] |
| COB-146 | 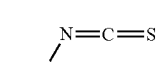 | 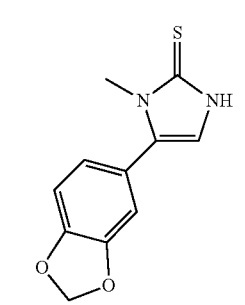 [SMILES: Cn1c(-c2ccc3c(c2)OCO3)c[nH]c1=S] | |

TABLE 1-continued

| Reference | Reactant (1a) or (2a) | Reactant (1b) or (2b) | Compound of General Formula (I) or (II) |
|---|---|---|---|
| COB-152 | phenacyl bromide | pyridin-3-ylmethylamine + CS$_2$ | 3-(pyridin-3-ylmethyl)-4-hydroxy-4-phenylthiazolidine-2-thione |
| COB-153 | Dehydration of COB-152 | | 3-(pyridin-3-ylmethyl)-4-phenyl-2,3-dihydrothiazole-2-thione |
| COB-161 | 2-bromo-1-tetralone | benzylamine | N-benzyl fused naphthothiazolethione |
| COB-168 | phenacyl bromide | 3-phenylpropylamine + CS$_2$ | 3-(3-phenylpropyl)-4-hydroxy-4-phenylthiazolidine-2-thione |
| COB-178 | Dehydration of COB-168 | | 3-(3-phenylpropyl)-4-phenyl-2,3-dihydrothiazole-2-thione |
| COB-176 | 2-bromo-1-(pyridin-3-yl)ethanone | pyridin-3-ylmethylamine + CS$_2$ | 3-(pyridin-2-ylmethyl)-4-hydroxy-4-(pyridin-3-yl)thiazolidine-2-thione |
| COB-177 | Dehydration of reaction product of phenacyl bromide and phenethylamine + CS$_2$ | | 3-phenethyl-4-phenyl-2,3-dihydrothiazole-2-thione |

TABLE 1-continued

| Reference | Reactant (1a) or (2a) | Reactant (1b) or (2b) | Compound of General Formula (I) or (II) |
|---|---|---|---|
| COB-180 | PhC(O)CH2Br | 2-(2-aminoethyl)pyridine + CS2 | 3-(pyridin-2-ylmethyl)-4-hydroxy-4-phenyl-thiazolidine-2-thione |
| COB-189 | Dehydration of COB-180 | | 3-(pyridin-2-ylmethyl)-4-phenyl-2,3-dihydrothiazole-2-thione |
| COB-183 | PhC(O)CH2Br | (1H-benzimidazol-2-yl)methanamine + CS2 | 3-((1H-benzimidazol-2-yl)methyl)-4-hydroxy-4-phenyl-thiazolidine-2-thione |
| COB-192 | Dehydration of COB-183 | | 3-((1H-benzimidazol-2-yl)methyl)-4-phenyl-2,3-dihydrothiazole-2-thione |
| COB-186 | 2× PhC(O)CH2Br | 1,3-bis(aminomethyl)benzene + CS2 | bis-thiazolidine-2-thione (4-OH, 4-Ph) linked by 1,3-xylylene |
| COB-193 | Dehydration of COB-186 | | bis-(4-phenyl-2,3-dihydrothiazole-2-thione) linked by 1,3-xylylene |
| COB-187 | PhC(O)CH2Br | (pyridin-4-yl)methanamine + CS2 | 3-(pyridin-4-ylmethyl)-4-hydroxy-4-phenyl-thiazolidine-2-thione |

TABLE 1-continued

| Reference | Reactant (1a) or (2a) | Reactant (1b) or (2b) | Compound of General Formula (I) or (II) |
|---|---|---|---|
| COB-188 | phenacyl bromide | 1H-indol-5-ylmethanamine + CS₂ | 3-((1H-indol-5-yl)methyl)-4-hydroxy-4-phenylthiazolidine-2-thione |
| COB-190 | Dehydration of reaction product of phenacyl bromide and 4-chlorobenzylamine + CS₂ | | 3-(4-chlorobenzyl)-4-phenyl-2,3-dihydrothiazole-2-thione |
| COB-191 | Dehydration of reaction product of phenacyl bromide and 4-nitrobenzylamine + CS₂ | | 3-(4-nitrobenzyl)-4-phenyl-2,3-dihydrothiazole-2-thione |
| COB-196 | 2-bromo-1-(3-hydroxyphenyl)ethanone | benzylamine + CS₂ | 3-benzyl-4-(3-hydroxyphenyl)-4-hydroxythiazolidine-2-thione |
| COB-197 | 2-bromo-1-(2,5-dimethoxyphenyl)ethanone | pyridin-3-ylmethanamine + CS₂ | 4-(2,5-dimethoxyphenyl)-4-hydroxy-3-(pyridin-3-ylmethyl)thiazolidine-2-thione |
| COB-203 | Dehydration of COB-197 | | 4-(2,5-dimethoxyphenyl)-3-(pyridin-3-ylmethyl)-2,3-dihydrothiazole-2-thione |

TABLE 1-continued

| Reference | Reactant (1a) or (2a) | Reactant (1b) or (2b) | Compound of General Formula (I) or (II) |
|---|---|---|---|
| COB-198 | 2-bromo-1-(3-hydroxyphenyl)ethanone | pyridin-3-ylmethanamine + CS₂ | 3-(3-hydroxyphenyl)-3-hydroxy-N-(pyridin-3-ylmethyl)thiazolidine-2-thione |
| COB-199 | 2-bromo-1-(2,4-dimethoxyphenyl)ethanone | pyridin-3-ylmethanamine + CS₂ | 4-(2,4-dimethoxyphenyl)-4-hydroxy-3-(pyridin-3-ylmethyl)thiazolidine-2-thione |
| COB-204 | Dehydration of COB-199 | | 4-(2,4-dimethoxyphenyl)-3-(pyridin-3-ylmethyl)thiazole-2(3H)-thione |
| COB-200 | 2-bromo-1-(2,4-dihydroxyphenyl)ethanone | pyridin-3-ylmethanamine + CS₂ | 4-(2,4-dihydroxyphenyl)-4-hydroxy-3-(pyridin-3-ylmethyl)thiazolidine-2-thione |
| COB-201 | 2-bromo-1-(4-methoxyphenyl)ethanone | pyridin-3-ylmethanamine + CS₂ | 4-hydroxy-4-(4-methoxyphenyl)-3-(pyridin-3-ylmethyl)thiazolidine-2-thione |

TABLE 1-continued

| Reference | Reactant (1a) or (2a) | Reactant (1b) or (2b) | Compound of General Formula (I) or (II) |
|---|---|---|---|
| COB-206 | Dehydration of COB-201 | | |
| COB-202 | | | |
| COB-205 | Dehydration of COB-202 | | |
| COB-207 | | | |
| COB-214 | Dehydration of COB-207 | | |

TABLE 1-continued
| Reference | Reactant (1a) or (2a) | Reactant (1b) or (2b) | Compound of General Formula (I) or (II) |
|---|---|---|---|
| COB-208 | 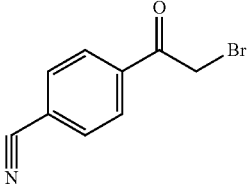 [SMILES: N#Cc1ccc(C(=O)CBr)cc1] |  | 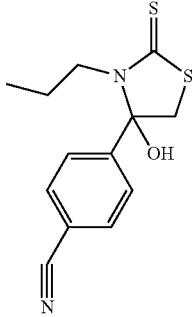 [SMILES: CCCN1C(=S)SCC1(O)c1ccc(C#N)cc1] |
| COB-216 | | Dehydration of COB-208 | 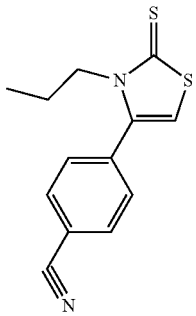 [SMILES: CCCn1c(-c2ccc(C#N)cc2)csc1=S] |
| COB-209 | 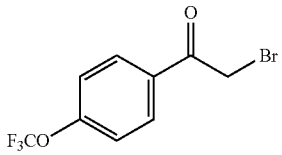 [SMILES: O=C(CBr)c1ccc(OC(F)(F)F)cc1] | 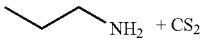 | 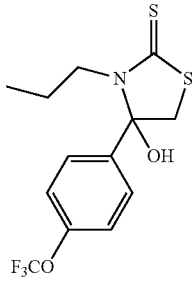 [SMILES: CCCN1C(=S)SCC1(O)c1ccc(OC(F)(F)F)cc1] |
| COB-210 | 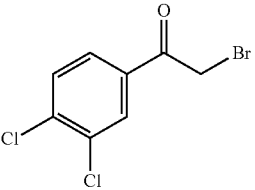 [SMILES: O=C(CBr)c1ccc(Cl)c(Cl)c1] | 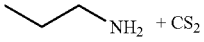 | 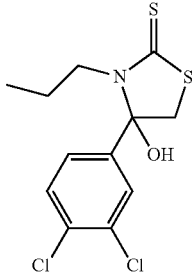 [SMILES: CCCN1C(=S)SCC1(O)c1ccc(Cl)c(Cl)c1] |
| COB-219 | | Dehydration of COB-210 | 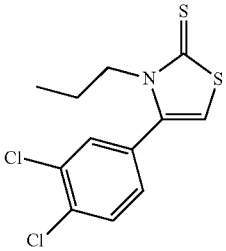 [SMILES: CCCn1c(-c2ccc(Cl)c(Cl)c2)csc1=S] |

TABLE 1-continued

| Reference | Reactant (1a) or (2a) | Reactant (1b) or (2b) | Compound of General Formula (I) or (II) |
| --- | --- | --- | --- |
| COB-212 | 2-bromo-1-phenylethan-1-one | hexylamine + CS$_2$ | 3-hexyl-4-hydroxy-4-phenylthiazolidine-2-thione |
| COB-213 | 2-bromo-1-(2,5-dimethoxyphenyl)ethan-1-one | propylamine + CS$_2$ | 4-(2,5-dimethoxyphenyl)-4-hydroxy-3-propylthiazolidine-2-thione |
| COB-220 | Dehydration of COB-213 | | 4-(2,5-dimethoxyphenyl)-3-propyl-2,3-dihydrothiazole-2-thione |
| COB-215 | Dehydration of reaction product of 2-bromo-1-(3-nitrophenyl)ethan-1-one and propylamine + CS$_2$ | | 4-(3-nitrophenyl)-3-propyl-2,3-dihydrothiazole-2-thione |
| COB-217 | Dehydration of reaction product of 2-bromo-1-phenylethan-1-one and allylamine + CS$_2$ | | 3-allyl-4-phenyl-2,3-dihydrothiazole-2-thione |
| COB-218 | Dehydration of reaction product of 2-bromo-1-phenylethan-1-one and hexylamine + CS$_2$ | | 3-hexyl-4-phenyl-2,3-dihydrothiazole-2-thione |

TABLE 1-continued

| Reference | Reactant (1a) or (2a) | Reactant (1b) or (2b) | Compound of General Formula (I) or (II) |
|---|---|---|---|
| COB-221 | 5-chloro-2-hydroxyphenacyl bromide | 3-(aminomethyl)pyridine + CS$_2$ | 3-benzyl-4-(5-chloro-2-hydroxyphenyl)-4-hydroxy-thiazolidine-2-thione |
| COB-222 | 5-chloro-2-hydroxyphenacyl bromide | 3-(aminomethyl)pyridine + CS$_2$ | 4-(5-chloro-2-hydroxyphenyl)-4-hydroxy-3-(pyridin-3-ylmethyl)-thiazolidine-2-thione |
| COB-223 | 2,5-dimethylphenacyl bromide | 3-(aminomethyl)pyridine + CS$_2$ | 4-(2,5-dimethylphenyl)-4-hydroxy-3-(pyridin-3-ylmethyl)-thiazolidine-2-thione |
| COB-224 | 2-methylphenacyl bromide | 3-(aminomethyl)pyridine + CS$_2$ | 4-hydroxy-4-(2-methylphenyl)-3-(pyridin-3-ylmethyl)-thiazolidine-2-thione |
| COB-225 | 5-fluoro-2-methoxyphenacyl bromide | 3-(aminomethyl)pyridine + CS$_2$ | 4-(5-fluoro-2-methoxyphenyl)-4-hydroxy-3-(pyridin-3-ylmethyl)-thiazolidine-2-thione |
| COB-226 | 2-chloro-5-(trifluoromethyl)phenacyl bromide | 3-(aminomethyl)pyridine + CS$_2$ | 4-(2-chloro-5-(trifluoromethyl)phenyl)-4-hydroxy-3-(pyridin-3-ylmethyl)-thiazolidine-2-thione |

TABLE 1-continued

| Reference | Reactant (1a) or (2a) | Reactant (1b) or (2b) | Compound of General Formula (I) or (II) |
|---|---|---|---|
| DRB-3 | Dehydration of reaction product of: 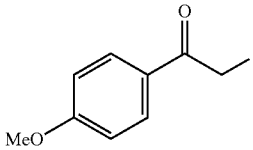 | and  $+ CS_2$ | 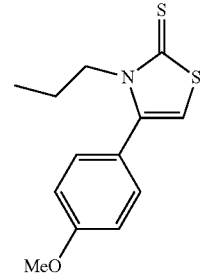 |
| GWB-93 | Dehydration of reaction product of: 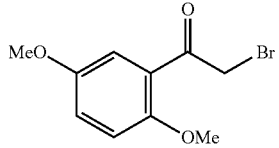 [SMILES: COc1ccc(OC)c(C(=O)CBr)c1] | and $CH_3NH_2 + CS_2$ | 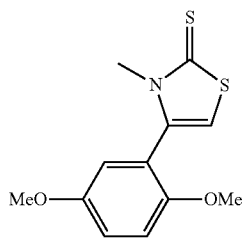 [SMILES: COc1ccc(OC)c(-c2csc(=S)n2C)c1] |
| Z-01 | Dehydration of reaction product of: 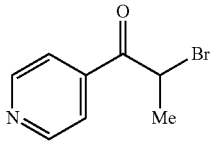 | and $CH_3NH_2 + CS_2$ | 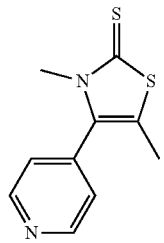 |
| Z-02 | Dehydration of reaction product of: 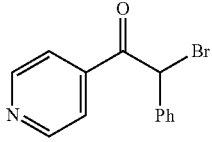 | and $CH_3NH_2 + CS_2$ | 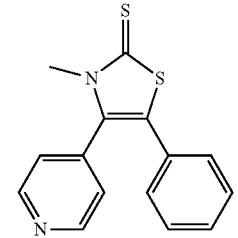 [SMILES: Cn1c(-c2ccncc2)c(-c2ccccc2)sc1=S] |
| Z-03 | Dehydration of reaction product of: 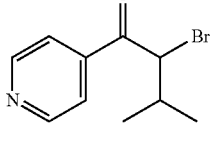 | and $CH_3NH_2 + CS_2$ | 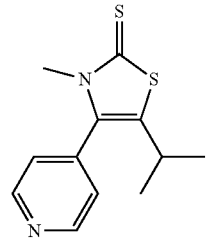 [SMILES: CC(C)c1sc(=S)n(C)c1-c1ccncc1] |
| Z-04 | Dehydration of reaction product of: 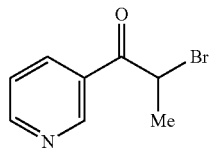 | and $CH_3NH_2 + CS_2$ | 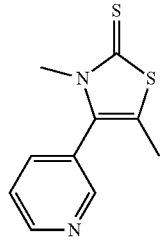 |

TABLE 1-continued

| Reference | Reactant (1a) or (2a) | Reactant (1b) or (2b) | Compound of General Formula (I) or (II) |
|---|---|---|---|
| Z-05 | Dehydration of reaction product of: 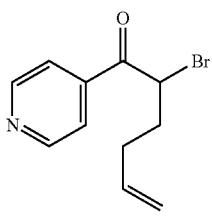 and CH$_3$NH$_2$ + CS$_2$ | | 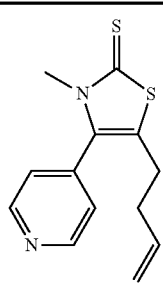 |
| Z-06 | Dehydration of reaction product of: 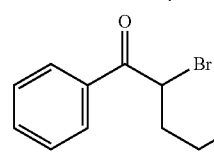 and 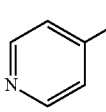 + CS$_2$ | | 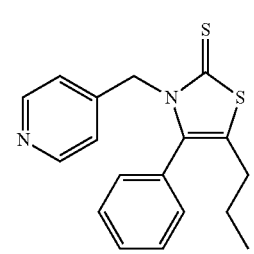 [SMILES: CCCc1sc(=S)n(Cc2ccncc2)c1-c1ccccc1] |
| Z-07 | Dehydration of reaction product of: 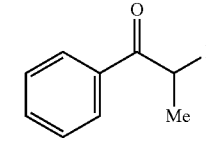 and  + CS$_2$ | | 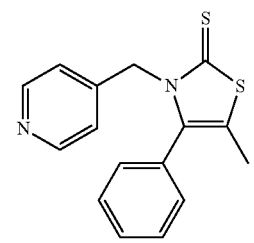 [SMILES: Cc1sc(=S)n(Cc2ccncc2)c1-c1ccccc1] |
| Z-08 | Dehydration of reaction product of: 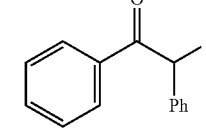 and  + CS$_2$ | | 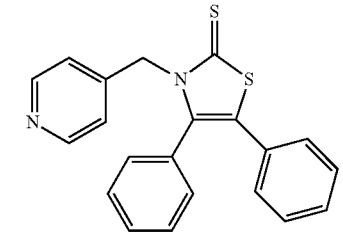 [SMILES: S=c1sc(-c2ccccc2)c(-c2ccccc2)n1Cc1ccncc1] |
| Z-09 | Dehydration of reaction product of: 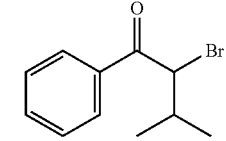 and  + CS$_2$ | | 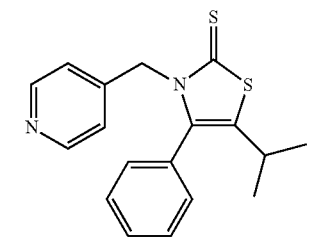 [SMILES: CC(C)c1sc(=S)n(Cc2ccncc2)c1-c1ccccc1] |
| Z-10 | Dehydration of reaction product of: 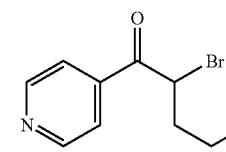 and CH$_3$NH$_2$ + CS$_2$ | | 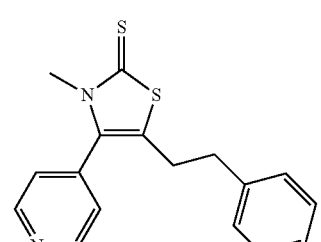 |

The compounds of General Formula (I) and General Formula (II) may be generally described as a class of compounds composed of four genera: (1) imidazole 2-thiones (in which group X is S and group Y is NH); (2) imidazole 2-ones (in which group X is O and group Y is NH); (3) thiazole 2-thiones (in which group X is S and group Y is S); and (4) thiazole 2-ones (in which group X is O and group Y is S).

According to some embodiments, in the compounds of General Formula (I) and General Formula (II), when $R^2$ is phenyl and $R^3$ is hydrogen, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; or (c) $R^1$ is $Ph(CH_2)_n$—, where n is 2 or 3 (i.e., group $R^1$ is 2-phenylethyl or 3-phenylpropyl); or (d) $R^1$ is a $C_1$ to $C_{10}$ heteroaliphatic group, optionally substituted with one or more aryl groups, substituted aryl groups, heteroaryl groups, substituted heteroaryl groups, or combination thereof. According to such embodiments, compounds of General Formula (I) and General Formula (II) do not include compounds in which group $R^2$ is phenyl and group $R^1$ is an unsubstituted aliphatic group other than hexyl.

In general, the provisos (a)-(d) define the scope of General Formula (I) and General Formula (II) when $R^2$ is phenyl and $R^3$ is hydrogen, based on the identity of $R^1$. For example, considering all provisos together, when $R^2$ is phenyl and $R^3$ is hydrogen, $C_1$ to $C_{10}$ aliphatic groups $R^1$ as defined under proviso (a) must be substituted with at least one substituted aryl group, at least one heteroaryl group, or at least one substituted heteroaryl group. Proviso (b) adds $R^1$=hexyl to the definition of $C_1$ to $C_{10}$ aliphatic groups from proviso (a), and proviso (c) adds 2-phenylethyl and 3-phenylpropyl to the definition of $C_1$ to $C_{10}$ aliphatic groups from proviso (a). That is, when $R^2$ is phenyl and $R^3$ is hydrogen, $C_1$ to $C_{10}$ aliphatic groups $R^1$ do not include unsubstituted aliphatic groups such as methyl, ethyl, isopropyl, or cyclohexyl but do include hexyl groups. Likewise, when $R^2$ is phenyl and $R^3$ is hydrogen, $C_1$ to $C_{10}$ aliphatic groups $R^1$ do not include aliphatic groups substituted with aryl groups that themselves are not substituted (such as phenyl), with the exception from proviso (c) that $R^1$ may be 2-phenylethyl or 3-phenylpropyl. In view of proviso (d), however, even when $R^2$ is phenyl and $R^3$ is hydrogen, $C_1$ to $C_{10}$ heteroaliphatic groups $R^1$ may be unsubstituted or substituted. When the $C_1$ to $C_{10}$ heteroaliphatic groups $R^1$ are substituted, they may be substituted with one or more aryl groups (even unsubstituted aryl groups), substituted aryl groups, heteroaryl groups, substituted heteroaryl groups, or combinations thereof.

According to some embodiments, in the compounds of General Formula (I) and General Formula (II), when $R^2$ is phenyl and $R^3$ is hydrogen, the compound having General Formula (I) or General Formula (II) is selected from the group consisting of

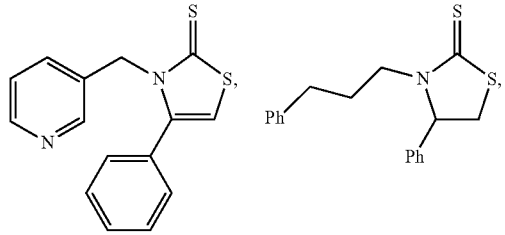

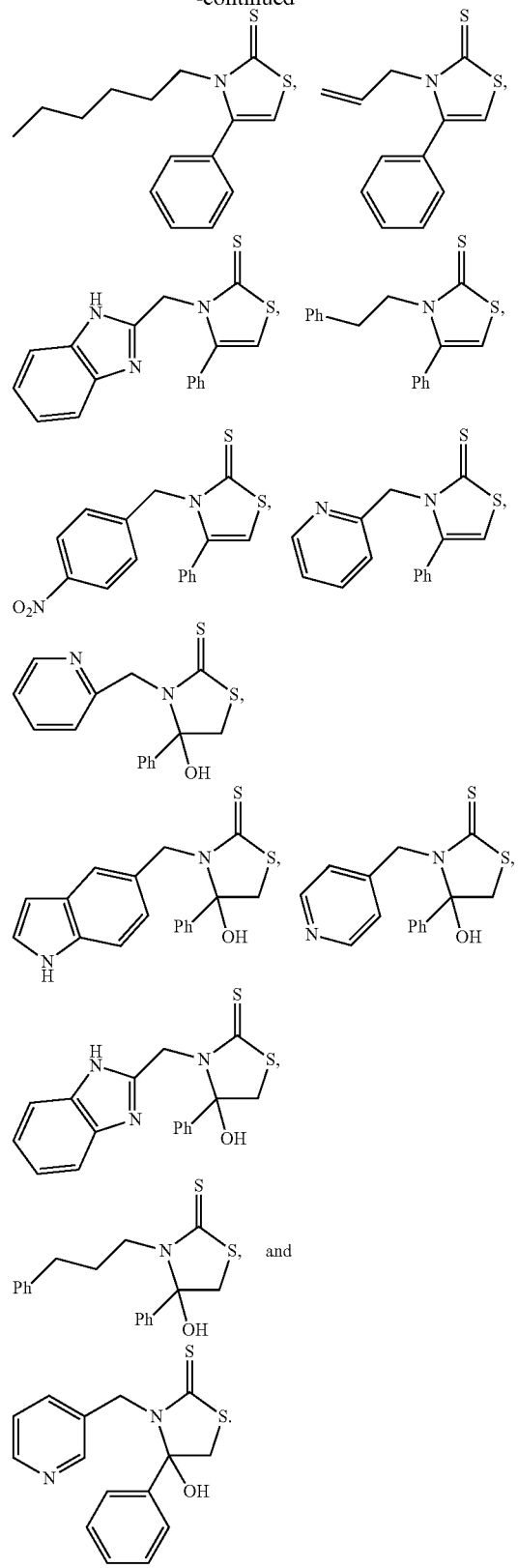

In some embodiments, the compounds of General Formula (I) or General Formula (II) do not include one or more of the compounds listed in TABLE 2, or may not include any of the compounds listed in TABLE 2:

TABLE 2

| Reference | Compound |
|---|---|
| X-010 | 1-methyl-5-phenyl-1H-imidazole-2(3H)-thione |
| X-105 | 1-allyl-5-phenyl-1H-imidazole-2(3H)-thione |
| X-106 | 1-benzyl-5-phenyl-1H-imidazole-2(3H)-thione |
| X-107 | 1-phenethyl-5-phenyl-1H-imidazole-2(3H)-thione |
| X-108 | 1-isopropyl-5-phenyl-1H-imidazole-2(3H)-thione |
| X-109 | 1-cyclohexyl-5-phenyl-1H-imidazole-2(3H)-thione |
| X-110 | 1,5-diphenyl-1H-imidazole-2(3H)-thione |
| X-111 | 5-(4-methoxyphenyl)-1-methyl-1H-imidazole-2(3H)-thione |
| X-112 | 5-(4-chlorophenyl)-1-methyl-1H-imidazole-2(3H)-thione |
| X-113 | 1-ethyl-5-phenyl-1H-imidazol-2(3H)-one |
| X-114 | 1-butyl-5-phenyl-1H-imidazol-2(3H)-one |
| X-115 | 1-(2-morpholinoethyl)-5-phenyl-1H-imidazole-2(3H)-thione |
| X-116 | 1-methyl-5-(p-tolyl)-1H-imidazole-2(3H)-thione |
| X-120 | 1-hexyl-5-phenyl-1H-imidazole-2(3H)-thione |
| X-127 | 5-(3,4-dichlorophenyl)-1-methyl-1H-imidazole-2(3H)-thione |

TABLE 2-continued

| Reference | Compound |
|---|---|
| X-131 | (1-methyl-5-(thiophen-2-yl)-1H-imidazole-2(3H)-thione) |
| X-135 | (5-(4-phenylphenyl)-1-methyl-1H-imidazole-2(3H)-thione) |
| X-136 | (3-benzyl-4-hydroxy-4-phenylthiazolidine-2-thione) |
| X-137 | (3-benzyl-4-phenyl-2,3-dihydrothiazole-2-thione) |
| X-142 | (4-hydroxy-4-phenyl-3-propylthiazolidine-2-thione) |
| X-145 | (1-methyl-5-(3-nitrophenyl)-1H-imidazole-2(3H)-thione) |
| X-149 | (1-benzyl-5-phenyl-1H-imidazol-2(3H)-one) |
| X-150 | (5-phenyl-1-propyl-1H-imidazol-2(3H)-one) |
| X-151 | (5-phenyl-1-propyl-1H-imidazole-2(3H)-thione) |
| X-154 | (4-phenyl-3-propyloxazol-2(3H)-one) |
| X-156 | (3-benzyl-4-hydroxy-4-phenyloxazolidin-2-one) |
| X-157 | (3-benzyl-4-phenyloxazol-2(3H)-one) |
| X-167 | (4-hydroxy-3-phenethyl-4-phenylthiazolidine-2-thione) |
| X-169 | (4-hydroxy-3-(4-methoxybenzyl)-4-phenylthiazolidine-2-thione) |
| X-179 | (3-(4-methoxybenzyl)-4-phenyl-2,3-dihydrothiazole-2-thione) |

TABLE 2-continued

| Reference | Compound |
|---|---|
| X-181 | (4-chlorobenzyl)-4-phenyl-4-hydroxy-thiazolidine-2-thione |
| X-182 | (4-nitrobenzyl)-4-phenyl-4-hydroxy-thiazolidine-2-thione |
| X-184 | 3-(phenylamino)-4-phenyl-4-hydroxy-thiazolidine-2-thione |
| X-185 | 3-(benzoylamino)-4-phenyl-4-hydroxy-thiazolidine-2-thione |
| X-194 | 3-(benzoylamino)-4-phenyl-thiazole-2-thione |
| X-195 | 3-phenyl-4-phenyl-4-hydroxy-thiazolidine-2-thione |
| X-211 | 3-allyl-4-phenyl-4-hydroxy-thiazolidine-2-thione |
| X-B2 | 3-methyl-4-(4-methoxyphenyl)-thiazole-2-thione |
| X-B4 | 3-propyl-4-(4-methoxyphenyl)-4-hydroxy-thiazolidine-2-thione |

The term "imidazole 2-thiones", as used herein, refers to compositions having the general structural formula (I) and/or general structural formula (II) as described above, in which group X is S and group Y is NH.

The term "imidazole 2-ones", as used herein, refers to compositions having the general structural formula (I) and/or general structural formula (II) as described above, in which group X is O and group Y is NH.

The term "thiazole 2-thiones", as used herein, refers to compositions having the general structural formula (I) and/or general structural formula (II) as described above, in which group X is S and group Y is S.

The term "thiazole 2-ones", as used herein, refers to compositions having the general structural formula (I) and/or general structural formula (II) as described above, in which group X is O and group Y is S.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" may be used to indicate alkyl groups (substituted, unsubstituted, branched or unbranched) having from 1 to 6 carbon atoms.

In certain embodiments, the alkyl, alkenyl, and alkynyl groups described herein contain from 1 to 10 aliphatic carbon atoms. In other embodiments, the alkyl, alkenyl, and alkynyl groups described herein contain from 1 to 8 aliphatic carbon atoms. In still other embodiments, the alkyl, alkenyl, and alkynyl groups described herein contain from 1 to 6 aliphatic carbon atoms. In yet other embodiments, the alkyl, alkenyl, and alkynyl groups described herein contain from 1 to 4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which optionally may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norbornyl moieties and the like, which optionally may bear one or more substituents.

The term "alkoxy" or "alkyloxy", as used herein, refers to a saturated (i.e., O-alkyl) or unsaturated (i.e., O-alkenyl and O-alkynyl) group attached to the parent molecular moiety through an oxygen atom. In certain embodiments, the alkyl group contains from 1 to 10 aliphatic carbon atoms. In yet other embodiments, the alkyl group contains from 1 to 8 aliphatic carbon atoms. In still other embodiments, the alkyl group contains from 1 to 6 aliphatic carbon atoms. In yet other embodiments, the alkyl group contains from 1 to 4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl", as used herein, refers to a saturated (i.e., S-alkyl) or unsaturated (i.e., S-alkenyl and S-alkynyl) group attached to the parent molecular moiety through a sulfur atom. In certain embodiments, the alkyl group contains from 1 to 10 aliphatic carbon atoms. In yet other embodiments, the alkyl group contains from 1 to 8 aliphatic carbon atoms. In still other embodiments, the alkyl group contains from 1 to 6 aliphatic carbon atoms. In yet other embodiments, the alkyl group contains from 1 to 4 aliphatic carbon atoms. Examples of thioalkyl include, but are not limited to, methylthio, ethylthio, propylthio, isopropylthio, n-butylthio, and the like.

The term "alkylamino", as used herein, refers to a group having the structure NHR' wherein R' is alkyl, as defined herein. The term "aminoalkyl" refers to a group having the structure NH$_2$R'—, wherein R' is alkyl, as defined herein. In certain embodiments, the alkyl group contains from 1 to 10 aliphatic carbon atoms. In yet other embodiments, the alkyl groups contain from 1 to 8 aliphatic carbon atoms. In still other embodiments, the alkyl group contains from 1 to 6 aliphatic carbon atoms. In yet other embodiments, the alkyl group contains from 1 to 4 aliphatic carbon atoms. Examples of alkylamino include, but are not limited to, methylamino, ethylamino, isopropylamino and the like.

Some examples of substituents of the above-described aliphatic (and other) moieties of compounds described herein include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; hetero alkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)$_2$R$^X$; —NR$^X$(CO)R$^X$, wherein each occurrence of R$^X$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above herein and may be substituted or unsubstituted, branched or unbranched, saturated or unsaturated, and wherein any of the aryl or heteroaryl substituents described above herein may be substituted or unsubstituted. Additional examples of generally applicable substituents are illustrated by the specific embodiments shown in the Examples that are described below.

In general, the terms "aromatic moiety" as used herein refer to a stable monocyclic or polycyclic, unsaturated moiety having preferably from 3 to 14 carbon atoms, each of which may be substituted or unsubstituted. In certain embodiments, the terms "aromatic moiety" refer to a planar ring having p-orbitals perpendicular to the plane of the ring at each ring atom and satisfying the Hückel rule where the number of pi electrons in the ring is (4n+2), where n is an integer. A monocyclic or polycyclic, unsaturated moiety that does not satisfy one or all of these criteria for aromaticity is defined herein as "non-aromatic" and is encompassed by the term "alicyclic."

In general, the term "heteroaromatic moiety" as used herein refers to a stable monocyclic or polycyclic, unsaturated moiety having preferably from 3 to 14 carbon atoms, each of which may be substituted or unsubstituted; and comprising at least one heteroatom selected from O, S, and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Hückel rule where the number of pi electrons in the ring is (4n+2), where n is an integer.

It should be appreciated that aromatic and heteroaromatic moieties, as defined herein may be attached via an alkyl or heteroalkyl moiety and thus also include, as non-limiting examples: -(alkyl)-aromatic, -(heteroalkyl)-aromatic, -(heteroalkyl)-heteroaromatic, and -(heteroalkyl)-heteroaromatic moieties. Thus, as used herein, the phrases "aromatic or heteroaromatic moieties" and "aromatic, heteroaromatic, -(alkyl)-aromatic, -(heteroalkyl)-aromatic, -(heteroalkyl)-heteroaromatic, and -(heteroalkyl)-heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a monocyclic or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from 5 to 10 ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It should be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4-membered, 5-membered, 6-membered, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$(CO)R$^X$ wherein, each occurrence of R$^X$ independently includes, but is not limited to, aliphatic, alicyclic, heteroaliphatic, heterocyclic, aromatic, hetero aromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The terms "heterocycloalkyl," "heterocycle," and/or "heterocyclic", as used herein, refer to compounds that combine the properties of heteroaliphatic and cyclic compounds and include, but are not limited to, saturated and unsaturated mono- or polycyclic cyclic ring systems having from 5 to 16 atoms, wherein at least one ring atom is a heteroatom selected from O, S, and N (wherein the nitrogen and sulfur heteroatoms may optionally be oxidized), wherein the ring systems are optionally substituted with one or more functional groups, as defined herein. In certain embodiments, the term "heterocycloalkyl", "heterocycle" or "heterocyclic" refers to a non-aromatic 5-membered, 6-membered, or 7-membered ring or a polycyclic group wherein at least one ring atom is a heteroatom selected from O, S, and N (wherein the nitrogen and sulfur heteroatoms may be optionally be oxidized), including, but not limited to, a bicyclic or tricyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds; (ii) the nitrogen and sulfur heteroatoms may optionally be oxidized; (iii) the nitrogen heteroatom may optionally be quaternized; and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof.

In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with groups including but not limited to aliphatic; alicyclic; heteroaliphatic; heterocyclic; aromatic; hetero aromatic; aryl; heteroaryl; alkylaryl; heteroalkylaryl; alkylheteroaryl; hetero alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$^X$; —CO$_2$(R$^X$); —CON(R$^X$)$_2$; —OC(O)R$^X$; —OCO$_2$R$^X$; —OCON(R$^X$)$_2$; —N(R$^X$)$_2$; —S(O)R$^X$; —S(O)$_2$R$^X$; —NR$^X$ (CO)R$^X$ wherein each occurrence of R$^X$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it should be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and/or "halogen", as used herein, refer to an atom selected from fluorine, chlorine, bromine and iodine.

The term "haloalkyl", as used herein, denotes an alkyl group, as defined above, having one, two, or three halogen atoms attached thereto and is exemplified by such groups as chloromethyl, bromoethyl, trifluoromethyl, and the like.

The term "amino", as used herein, refers to a primary amine (—NH$_2$), a secondary amine (—NHR$^X$), a tertiary amine (—NR$^X$R$^Y$), or a quaternary amine (—N$^+$R$^X$R$^Y$R$^Z$), where R$^X$, R$^Y$, and R$^Z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, isopropylamino, piperidino, trimethylamino, and propylamino.

The term "C$_1$-C$_6$ alkylidene", as used herein, refers to a substituted or unsubstituted, linear or branched, saturated divalent radical consisting solely of carbon and hydrogen atoms, having from one to six carbon atoms, having a free valence "—" at both ends of the radical.

The term "C$_2$-C$_6$ alkenylidene", as used herein, refers to a substituted or unsubstituted, linear or branched, unsaturated divalent radical consisting solely of carbon and hydrogen atoms, having from two to six carbon atoms, having a free valence "—" at both ends of the radical, and wherein the unsaturation is present only as double bonds and wherein a double bond can exist between the first carbon of the chain and the rest of the molecule.

The terms "aliphatic," "hetero aliphatic," "alkyl," "alkenyl," "alkynyl," "heteroalkyl," "heteroalkenyl," and/or "heteroalkynyl," and the like, as used herein, encompass substituted and unsubstituted, saturated and unsaturated, and linear and branched groups. Similarly, the terms "alicyclic," "heterocyclic," "heterocycloalkyl," "heterocycle" and the like encompass substituted and unsubstituted, and saturated and unsaturated groups. Additionally, the tetras "cycloalkyl," "cycloalkenyl," "cycloalkynyl," "heterocyclo alkyl," "heterocycloalkenyl," "heterocyclo alkynyl," "aromatic," "hetero aromatic," "aryl," "hetero aryl" and the like encompass both substituted and unsubstituted groups.

The term "pharmaceutically acceptable salts" refers to salts prepared from pharmaceutically acceptable non-toxic bases or acids including inorganic or organic bases and inorganic or organic acids. Salts derived from inorganic bases include: aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include: salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When a compound is basic, salts may be prepared from pharmaceutically acceptable nontoxic acids, including inorganic and organic acids. Such acids include: acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. Thus, representative pharmaceutically acceptable salts include but are not limited to acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexyl-resorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. It will be understood that, as used herein, the compounds referred to herein are meant to also include the pharmaceutically acceptable salts.

It is understood that certain embodiments herein encompass the use of pharmaceutically acceptable salts, pharmaceutically acceptable solvates, or pharmaceutically acceptable salts solvated with pharmaceutically acceptable solvents. As used herein, the term "solvate" or "salt solvated" refers to a complex of variable stoichiometry formed by a solute (such as compounds of Formula (I) or (II) described below (or a salt thereof)) and a solvent. In some embodiments, such solvents do not interfere with the biological activity of the solute. Examples of suitable solvents include, but are not limited to, water, methanol, ethanol and acetic acid. In illustrative embodiments, the solvent is a pharmaceutically acceptable solvent. Examples of suitable pharmaceutically acceptable solvents include, without limitation, water, ethanol, and acetic acid. In one particular embodiment, the solvent is water, providing a "hydrate."

Embodiments of the present disclosure relate to methods for preventing and/or treating NAFLD, to methods for inhibiting excessive accumulation of fat, and to pharmaceutical compositions for preventing and/or treating NAFLD. Embodiments of the methods for preventing and/or treating NAFLD will now be described in detail. Thereafter, embodiments of methods for inhibiting excessive accumulation of fat and pharmaceutical compositions for preventing and/or treating NAFLD will be described in detail.

I. Methods for Preventing and/or Treating NAFLD

Methods for preventing and/or treating NAFLD in a subject in need thereof are disclosed. In embodiments, a method for preventing NAFLD in a subject in need thereof is disclosed. Such method may include administering a therapeutically effective amount of at least one imidazole and/or thiazole compound and, more specifically, at least one imidazole 2-thione, imidazole 2-one, thiazole 2-thione, and/or thiazole 2-one, to the subject, or pharmaceutically-acceptable salts or solvates thereof, wherein administration of the imidazole and/or thiazole compound is effective to prevent NAFLD. The imidazole and/or thiazole compounds referenced herein are as previously described. In embodiments, the method includes administering imidazole and/or thiazole compounds to the subject. In particular embodiments, the method includes administering a therapeutically effective amount of COB-204, COB-214, COB-152, and/or COB-187 to the subject. In further embodiments, administration of the therapeutically effective amount of imidazole and/or thiazole compounds and, more specifically, at least one imidazole 2-thione, imidazole 2-one, thiazole 2-thione, and/or thiazole 2-one, to the subject is effective to prevent NAFLD by preventing excessive accumulation of fat in a liver cell, in liver tissue, and/or in the liver of the subject.

Excessive accumulation of fat may be determined via standard diagnostic testing techniques for NAFLD, such as those previously described. For example, fat content in the liver cell, liver tissue and/or the liver may be assessed via blood tests (e.g., liver function tests including tests of liver enzymes and/or triglyceride quantification); imaging procedures (e.g., ultrasound, computerized tomography scan and/or magnetic resonance imaging); and liver tissue testing (e.g., liver biopsy). More specifically, excessive accumulation of fat in the liver cell, liver tissue, and/or the liver may be determined via comparison to the fat content of a normal liver cell, liver tissue, and/or the liver of a subject who is not in need of treatment for NAFLD (or to the normal level). Additionally, by way of example, the subject in need thereof may be a subject at risk for developing NAFLD and/or a subject exhibiting symptoms associated with NAFLD.

In one or more particular embodiments, a method for reducing the risk of developing NAFLD in a subject in need thereof is disclosed. In such embodiments, the method includes administering a therapeutically effective amount of at least one imidazole and/or thiazole compound and, more specifically, at least one imidazole 2-thione, imidazole 2-one, thiazole 2-thione, and/or thiazole 2-one, or pharmaceutically-acceptable salts or solvates thereof, to the subject, wherein administration of the imidazole and/or thiazole compounds is effective to reduce the risk of developing NAFLD in the subject. The imidazole and/or thiazole compounds referenced herein are as previously described. In one embodiment, the method includes administering a therapeutically effective amount of imidazole and/or thiazole compounds to the subject. In particular embodiments, the method includes administering a therapeutically effective amount of COB-204, COB-214, COB-152, and/or COB-187 to the subject. In further embodiments, administration of the therapeutically effective amount of the imidazole and/or thiazole compound to the subject is effective to reduce the risk of developing NAFLD in the subject by preventing excessive accumulation of fat in a liver cell, in liver tissue, and/or in the liver of the subject. Excessive accumulation of fat in the liver cell, liver tissue and/or the liver may be determined via blood tests; imaging procedures, and liver tissue testing, as previously described. Additionally, by way of example, the subject in need thereof may be a subject at risk for developing NAFLD and/or a subject exhibiting symptoms associated with NAFLD.

In other embodiments, a method for treating NAFLD in a subject in need thereof is disclosed. In such embodiments, the method includes administering a therapeutically effective amount of at least one imidazole and/or thiazole compound to the subject, or pharmaceutically-acceptable salts or solvates thereof, wherein administration of the imidazole and/or thiazole compound is effective to treat NAFLD. The imidazole and/or thiazole compounds referenced herein are as previously described. In embodiments, the method includes administering a therapeutically effective amount of imidazole and/or thiazole compounds to the subject. In one or more particular embodiments, the method includes administering a therapeutically effective amount of the COB-204, COB-214, COB-152, and/or COB-187 compounds to the subject. In further embodiments, administration of the therapeutically effective amount of the imidazole and/or thiazole compound to the subject is effective to treat NAFLD by reducing fat content in a liver cell, in liver tissue, and/or in the liver of the subject relative to a baseline level. In still further embodiments, administration of the therapeutically effective amount of the imidazole and/or thiazole compounds to the subject is effective to treat NAFLD by reducing fat content in a liver cell, in liver tissue, and/or in the liver of the subject compared to a normal level. A reduction of fat content in a liver cell, liver tissue, and/or the liver may be determined via standard diagnostic testing techniques for NAFLD, as previously described. More specifically, a reduction of fat content may be determined via comparison, such as, e.g., visual and/or quantifiable, to the baseline and/or the normal level.

In other embodiments, the method includes administering a therapeutically effective amount of at least one imidazole and/or thiazole compound to the subject, wherein administration of the imidazole and/or thiazole compound is effective to inhibit progression of NAFLD. For example, administration of the imidazole and/or thiazole compound to the subject may be effective to inhibit the progression of NAFLD: (1) from steatosis to NASH, fibrosis, and/or cirrhosis; (2) from NASH to fibrosis and/or cirrhosis; and/or (3) from fibrosis to cirrhosis. Fat content in the liver cell, liver tissue, and/or the liver and/or progression of NAFLD may be determined via blood tests; imaging procedures, and liver tissue testing. Additionally, by way of example, the subject in need thereof may be a subject exhibiting symptoms associated with NAFLD and/or a subject having NAFLD.

In one or more embodiments, the methods for preventing and/or treating NAFLD include administration of at least one imidazole and/or thiazole compound, or pharmaceutically-acceptable salts or solvates thereof, to a subject in need thereof, wherein the subject is a mammal. In one or more particular embodiments, the subject is a mammal selected from the group consisting of humans, non-human primates, canines, felines, murines, bovines, equines, porcines, and lagomorphs. In further embodiments, the subject is a mouse.

In other embodiments, the methods for preventing and/or treating NAFLD include systemic administration of the imidazole and/or thiazole compounds, or pharmaceutically-acceptable salts or solvates thereof. The systemic administration of the imidazole and/or thiazole compounds may be selected from the group consisting of oral, sublingual, subcutaneous, intravenous, intramuscular, intranasal, intrathecal, intraperitoneal, percutaneous, intranasal, and enteral administration, and combinations thereof. In one or more particular embodiments, the systemic administration of the imidazole and/or thiazole compounds is oral.

In other embodiments, the methods for preventing and/or treating NAFLD include administration of at least one imidazole and/or thiazole compound, or pharmaceutically-acceptable salts or solvates thereof, to a subject in need thereof in a dose of from about 0.1 mg/kg to about 20 mg/kg, or from about 0.3 mg/kg to about 15 mg/kg, or from about 1 mg/kg to about 10 mg/kg, or from about 3 mg/kg to about 10 mg/kg, or from about 5 mg/kg to about 10 mg/kg. It is contemplated that such doses serve as non-limiting examples of suitable doses of imidazole and/or thiazole compounds for a subject in need thereof. In one or more particular embodiments, at least one imidazole and/or thiazole compound is administered to a subject in need thereof in a dose of about 1 mg/kg. In further embodiments, the dose of imidazole and/or thiazole compounds is administered daily. In still further embodiments, the dose of imidazole and/or thiazole compounds is administered at least once a day. In yet still a further embodiment, the dose of imidazole and/or thiazole compounds is administered more often than one time a day; for example, the dose of imidazole and/or thiazole compounds is administered at least two times a day, at least three times a day, at least four times a day, at least five times a day, and/or at least six times a day.

In yet other embodiments, the methods for preventing and/or treating NAFLD include co-administering with the effective amount of imidazole and/or thiazole compounds, or pharmaceutically-acceptable salts or solvates thereof, a therapeutically effective amount of one or more compounds for the treatment of metabolic syndrome, Hepatitis C, metabolic disorder, obesity, insulin resistance, inflammatory bowel disease, small-bowel diverticulosis, and/or viral infection. In some embodiments, co-administration may include administering a composition including at least one imidazole and/or thiazole compound prior to or subsequent to administering a separate composition including the one or more other compounds. In some embodiments, co-administration may include administering a composition including the imidazole and/or thiazole compounds and the one or more other compounds. In one or more particular embodiments, the methods for preventing and/or treating NAFLD include co-administering with the imidazole and/or thiazole compound a therapeutically effective amount of metformin, thiazolidinediones, and/or HMG-Co-A inhibitors (i.e., 3-hydroxy-3-methyl-glutaryl-CoA reductase inhibitors). In other particular embodiments, administration of the additional medication is systemic, as previously described.

In other embodiments, the methods for preventing and/or treating NAFLD in a subject in need thereof further include monitoring disease development and/or progression and repeating administration of imidazole and/or thiazole compounds (or pharmaceutically-acceptable salts or solvates thereof) one or more times, thereby preventing and/or treating NAFLD. Development and/or progression of NAFLD can be monitored in a variety of ways known to the skilled clinician, such as described with regard to diagnosis of NAFLD. For example, development and/or progression of NAFLD may be monitored via assessment of fat content in a liver cell, liiver tissue, and/or the liver one or more times. In embodiments, if the appropriate assessment indicates that NAFLD is developing, progressing, and/or has not yet responded to treatment (such as, e.g., wherein an increase in fat content in a liver cell, liver tissue, and/or the liver is determined), a clinician may administer an additional dose of at least one imidazole and/or thiazole compound. The clinician may then reassess disease development and/or progression. Successive rounds of administering imidazole and/or thiazole compounds coupled with monitoring development and/or progression of NAFLD, may be necessary in order to achieve the desired prevention and/or treatment of NAFLD.

Embodiments of the methods for preventing and/or treating NAFLD have been described in detail. Further embodiments of methods for inhibiting excessive accumulation of fat will now be described.

II. Methods for Inhibiting Excessive Accumulation of Fat

Methods for inhibiting excessive accumulation of fat in a liver cell, liver tissue, and/or the liver are disclosed. Such methods may include contacting the liver cell, liver tissue (e.g., a lobe of the liver), and/or the liver with a therapeutically effective amount of at least one imidazole and/or thiazole compound and, more specifically, at least one imidazole 2-thione, imidazole 2-one, thiazole 2-thione, and/or thiazole 2-one, to the subject, or pharmaceutically-acceptable salts or solvates thereof. The imidazole and/or thiazole compounds referenced herein are as previously described. In embodiments, the method includes contacting the liver cell, liver tissue, and/or the liver with a therapeutically effective amount of the imidazole and/or thiazole compounds. In particular embodiments, the method includes contacting the liver cell, liver tissue, and/or the liver with a therapeutically effective amount of COB-204, COB-214, COB-152, and/or COB-187.

In embodiments, contacting the liver cell, liver tissue, and/or the liver with a therapeutically effective amount of the imidazole and/or thiazole compounds is effective to prevent accumulation of fat in the liver tissue above a normal level. In other embodiments, contacting the liver cell, liver tissue, and/or the liver with a therapeutically effective amount of the imidazole and/or thiazole compounds is effective to reduce fat content in the liver tissue to at or below a normal level.

In some embodiments, the methods for inhibiting excessive accumulation of fat are performed by contacting a sample of a liver cell, liver tissue, and/or the liver with a therapeutically effective amount of the imidazole and/or thiazole compounds. In further embodiments, the methods for inhibiting excessive accumulation of fat are performed by contacting the liver cell, liver tissue, and/or the liver in a sample with a therapeutically effective amount of the imidazole and/or thiazole compounds in vitro and/or ex vivo. In embodiments, the liver cells, liver tissue, and/or liver employed in the methods disclosed herein include mammalian liver cells, liver tissue, and/or livers. More specifically, the liver cells, liver tissue, and/or livers may be human, non-human primate, canine, feline, murine, bovine, equine, porcine, and/or lagomorph.

In other embodiments, the methods for inhibiting excessive accumulation of fat are performed by contacting the liver cell, liver tissue, and/or the liver with a therapeutically effective amount of the imidazole and/or thiazole compounds in vivo. In such embodiments, the imidazole and/or the thiazole compounds may be administered to a subject in need thereof.

Embodiments of the methods for inhibiting excessive accumulation of fat have been described in detail. Further embodiments directed to pharmaceutical compositions for prevention and/or treatment of NAFLD will now be described.

III. Pharmaceutical Compositions for Prevention and/or Treatment of NAFLD

Pharmaceutical compositions for the prevention and/or treatment of NAFLD are disclosed. In one or more embodiments, a pharmaceutical composition including at least one imidazole and/or thiazole compound, or a pharmaceutically-acceptable salt or solvate thereof, as an active agent (i.e., an active ingredient) is disclosed. In other embodiments, a pharmaceutical composition including the imidazole and/or thiazole compounds as an active agent is disclosed, wherein the imidazole and/or thiazole compound is formulated for administration to a subject for the prevention and/or treatment of NAFLD. The imidazole and/or thiazole compounds referenced herein are as previously described. In embodiments, the pharmaceutical composition includes a therapeutically effective amount of one or more imidazole and/or thiazole compounds.

In some embodiments, the provided pharmaceutical compositions do not contain any of the compounds listed in TABLE 2. In some embodiments, the provided pharmaceutical compositions include one or more compounds listed in TABLE 2. In some embodiments, the provided pharmaceutical compositions include one or more compounds listed in TABLE 2 in combination with one or more compounds listed in TABLE 1.

In other embodiments, the pharmaceutical composition for the prevention and/or treatment of NAFLD further includes an additional active agent. In embodiments, the pharmaceutical composition for the prevention and/or treatment of NAFLD further includes a therapeutically effective amount of an additional active agent for the treatment of conditions associated with NAFLD. For example, the pharmaceutical composition for the prevention and/or treatment of NAFLD may further include an additional active agent for the treatment of NAFLD that may further include an additional active agent for the treatment of metabolic syndrome, Hepatitis C, metabolic disorder, obesity, insulin resistance, inflammatory bowel disease, small-bowel diverticulosis, and/or viral infection. In particular embodiments, the pharmaceutical composition for the treatment of NAFLD includes additional active agents of metformin, thiazolidinediones, and/or HMG-Co-A inhibitors.

In some embodiments, the pharmaceutical composition for the prevention and/or treatment of NAFLD further includes a pharmaceutically acceptable carrier and/or excipient. Suitable pharmaceutically acceptable carriers may include a wide range of known diluents (i.e., solvents), fillers, extending agents, adjuvants, binders, suspending agents, disintegrates, surfactants, lubricants, wetting agents, preservatives, stabilizers, antioxidants, antimicrobials, buffering agents and the like commonly used in this field. Such carriers may be used singly or in combination according to the form of the pharmaceutical preparation. In further embodiments, a preparation resulting from the inclusion of a pharmaceutically acceptable carrier may incorporate, if necessary, one or more solubilizing agents, buffers, preservatives, colorants, perfumes, flavorings and the like, as widely used in the field of pharmaceutical preparation.

Examples of suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, and vegetable oils. A full discussion of pharmaceutically acceptable excipients is provided in Remington's Pharmaceutical Sciences I (Mack Pub. Co.), the contents of which are incorporated by reference herein. Examples of suitable adjuvants include inorganic compounds (e.g., aluminum hydroxide, aluminum phosphate, calcium phosphate hydroxide, and beryllium), mineral oil (e.g., paraffin oil), bacterial products (e.g., killed bacteria *Bordetelle pertussis, Mycobacterium bovis*, and toxoids), nonbacterial organics (e.g., squalene and thimerosal), delivery systems (e.g., detergents (Quil A)), cytokines (e.g., IL-1, IL-2, and IL-12), and combinations (e.g., Freund's complete adjuvant, Freund's incomplete adjuvant). Examples of suitable preservatives, stabilizers, antioxidants, antimicrobials, and buffering agents include BHA, BHT, citric acid, ascorbic acid, tetracycline, and the like. Cream or ointment bases useful in formulation include lanolin, Silvadene® (Marion), Aquaphor® (Duke Laboratories).

In embodiments, the pharmaceutical composition for the prevention and/or treatment of NAFLD includes at least one imidazole and/or thiazole compound, or a pharmaceutically-acceptable salt or solvate thereof, formulated into a dosage form. In one or more particular embodiments, at least one imidazole and/or thiazole compound is formulated into a dosage form selected from the group consisting of creams, emulsions, ointments, gels, tablets, capsules, granules, pills, injections, solutions, suspensions, and syrups. The form and administration route for such pharmaceutical composition are not limited and can be suitably selected. For example, tablets, capsules, granules, pills, syrups, solutions, emulsions, and suspensions may be administered orally. Additionally, injections (e.g., subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

A pharmaceutical composition for the prevention and/or treatment of NAFLD may be prepared according to methods known in the pharmaceutical field using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

In some embodiments, the pharmaceutical compositions may include targeted or non-targeted carriers such as liposomes, particles made from biodegradeable particles, polymersomes, or ultrasound bubbles, for example. The compounds of General Formula (I) or (II) may be incorporated into the either non-targeted or targeted carriers. For the targeted particles, the targeting could be via a ligand attached to the particles, whereby the ligand is specific for a receptor overexpressed at the site of disease. Alternatively, when carriers are not present, the compounds of General Formula (I) or (II) may be conjugated to the targeting ligand directly to achieve the targeted delivery.

Injections, solutions, emulsions, suspensions, syrups and the like may be prepared according to known methods suitably using solvents for dissolving the active agent, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

In some embodiments, the pharmaceutical composition for the prevention and/or treatment of NAFLD includes a packaging material suitable for the pharmaceutical composition and instructions for use of the pharmaceutical composition for the prevention and/or treatment of NAFLD. In particular embodiments, the pharmaceutical composition for the prevention and/or treatment of NAFLD is provided for administration to a subject in unit dose and/or multi-dose containers, e.g., vials and/or ampoules. In specific embodiments, the pharmaceutical composition for the prevention and/or treatment of NAFLD is provided for administration to a subject in a device including a reservoir. In further specific embodiments, the pharmaceutical composition for the prevention and/or treatment of NAFLD is provided for administration to a subject in a device including a reservoir which is a vial, wherein the device is a syringe.

The pharmaceutical compositions for the prevention and/or treatment of NAFLD as described herein may be administered to a subject in need thereof in accordance with the methods for preventing and/or treating NAFLD, as described in an earlier section.

In some embodiments, at least one imidazole and/or thiazole compound, or a pharmaceutically-acceptable salt or solvate thereof, for use in the prevention and/or treatment of NAFLD is/are disclosed. In other embodiments, at least one imidazole and/or thiazole compound, or a pharmaceutically-acceptable salt or solvate thereof, for use in reducing the risk of acquiring NAFLD is/are disclosed. In still other embodiments, at least one imidazole and/or thiazole compound, or a pharmaceutically acceptable salt or solvate thereof, for use in the inhibition of excessive accumulation of fat in liver tissue is/are disclosed. In embodiments, the imidazole and/or thiazole compound, or a pharmaceutically-acceptable salt or solvate thereof, may further include an additional active agent for the treatment of conditions associated with NAFLD, as previously described. In other embodiments, the imidazole and/or thiazole compound, or a pharmaceutically-acceptable salt or solvate thereof, are incorporated into a pharmaceutical composition for the prevention and/or treatment of NAFLD and/or are formulated into a dosage form for the prevention and/or treatment of NAFLD, as previously described. The imidazole and/or thiazole compounds referenced herein are as previously described.

Embodiments of the pharmaceutical compositions for the prevention and/or treatment of NAFLD have been described in detail.

It should now be understood that various aspects of the present disclosure are described herein and that such aspects may be utilized in conjunction with various other aspects.

In a first aspect, a method for preventing and/or treating non-alcoholic fatty liver disease (NAFLD) in a subject in need thereof is disclosed. The method includes administering to the subject a therapeutically effective amount of at least one compound of General Formula (I) or (II):

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —FL at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In a second aspect, a method according to the first aspect is disclosed, wherein administration of at least one compound of General Formula (I) or (II) is effective to prevent NAFLD.

In a third aspect, a method according to any of the first or the second aspects is disclosed, wherein administration of at least one compound of General Formula (I) or (II) is effective to prevent NAFLD by preventing excessive accumulation of fat in liver tissue of the subject.

In a fourth aspect, a method according to any of the first to the third aspects is disclosed, wherein administration of at least one compound of General Formula (I) or (II) is effective to prevent NAFLD by preventing accumulation of fat in liver tissue of the subject above a normal level.

In a fifth aspect, a method according to the first aspect is disclosed, wherein administration of at least one compound of General Formula (I) or (II) is effective to treat NAFLD.

In a sixth aspect, a method according to the first or the fifth aspect is disclosed, wherein administration of at least one compound of General Formula (I) or (II) is effective to treat NAFLD by reducing fat content in liver tissue of the subject relative to a baseline level.

In a seventh aspect, a method according to any of the first to the sixth aspects is disclosed, wherein the subject is a mammal.

In an eighth aspect, a method according to any of the first to the seventh aspects is disclosed, wherein the subject is a mouse or a human.

In a ninth embodiment, a method according to any of the first to the eighth aspects is disclosed, wherein at least one compound of General Formula (I) or (II) is administered systemically.

In a tenth aspect, a method according to any of the first to the ninth aspects is disclosed, wherein at least one compound of General Formula (I) or (II) is administered in a dose of from about 1 mg/kg to about 10 mg/kg.

In an eleventh aspect, a method according to any of the first to the tenth aspects is disclosed, wherein at least one compound of General Formula (I) or (II) is administered in a dose of from about 3 mg/kg to about 10 mg/kg.

In a twelfth aspect, a method according to any of the first to the eleventh aspects is disclosed, wherein at least one compound of General Formula (I) or (II) is administered in a dose of from about 5 mg/kg to about 10 mg/kg.

In a thirteenth aspect, a method according to any of the first to the twelfth aspects is disclosed, wherein at least one compound of General Formula (I) or (II) is administered in a once daily dose.

In a fourteenth aspect, a method according to any of the first to the tenth or the thirteenth aspects is disclosed, wherein at least one compound of General Formula (I) or (II) is administered in a once daily dose of about 1 mg/kg.

In a fifteenth aspect, a method according to any of the first to the fourteenth aspects is disclosed, further including co-administering at least one of metformin, a thiazolidinedione, or an HMG-Co-A inhibitor.

In a sixteenth aspect, a method according to the first to the fifteenth aspects is disclosed, wherein at least one compound of General Formula (I) or (II) is a thiazole 2-thione.

In a seventeenth aspect, a method according to the first to the sixteenth aspects is disclosed, wherein $R^3$ is —H; X is S; and Y is S in at least one compound of General Formula (I) or (II).

In an eighteenth aspect, a method according to the first to the sixteenth aspects is disclosed, wherein $R^1$ is chosen from $C_1$ to $C_4$ aliphatic or heteroaliphatic groups optionally substituted with one or more aryl groups, substituted aryl groups, heteroaryl groups, substituted heteroaryl groups, or combination thereof; $R^3$ is —H; X is S; and Y is S in at least one compound of General Formula (I) or (II).

In a nineteenth aspect, a method according to the first to the eighteenth aspects is disclosed, wherien $R^2$ is chosen from unsubstituted phenyl groups, substituted phenyl groups, or heteroaryl groups in which one or more ring atoms is N; $R^3$ is —H; X is S; and Y is S in at least one compound of General Formula (I) or (II).

In a twentieth aspect, a method according to the first to the nineteenth aspects is disclosed, wherein $R^1$ is chosen from $C_1$ to $C_4$ aliphatic or heteroaliphatic groups optionally substituted with one or more aryl groups, substituted aryl groups, heteroaryl groups, substituted heteroaryl groups, or combination thereof; $R^2$ is chosen from unsubstituted phenyl groups, substituted phenyl groups, or heteroaryl groups in which one or more ring atoms is N; $R^3$ is —H; X is S; and Y is S in at least one compound of General Formula (I) or (II).

In a twenty-first aspect, a method according to the first to the twentieth aspects is disclosed, wherein $R^1$ is chosen from $C_1$ to $C_4$ aliphatic groups optionally substituted with heteroaryl groups in which one or more ring atoms is N, or combination thereof; $R^2$ is chosen from unsubstituted phenyl groups, disubstituted phenyl groups, or heteroaryl groups in which one or more ring atoms is N; $R^3$ is —H; X is S; and Y is S in at least one compound of General Formula (I) or (II).

In a twenty-second aspect, a method according to the first to the twenty-first aspects is disclosed, wherein $R^1$ is chosen from methyl, ethyl, propyl, butyl, 2-propenyl,

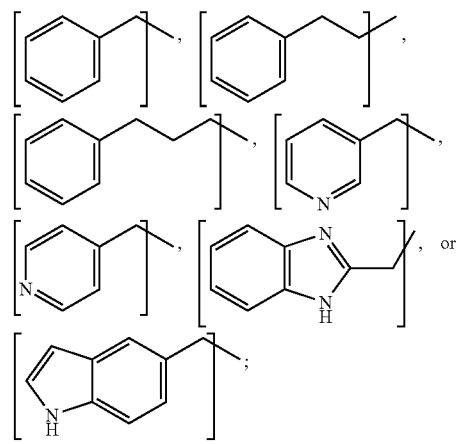

and $R^2$ is chosen from unsubstituted phenyl groups, 2,4-disubstituted phenyl groups, or heteroaryl groups in at least one compound of General Formula (I) or (II).

In a twenty-third aspect, a method according to the first to the twenty-second aspects is disclosed, wherein $R^1$ is chosen from

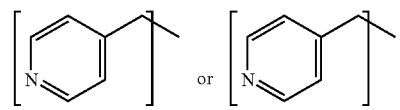

in at least one compound of General Formula (I) or (II).

In a twenty-fourth aspect, a method according to the first to the twenty-second aspects is disclosed, wherein $R^2$ is

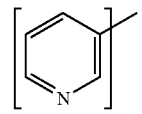

in at least one compound of General Formula (I) or (II).

In a twenty-fifth aspect, a method according to the first to the twenty-fourth aspects is disclosed, wherein at least one compound of General Formula (I) or (II) is chosen from COB-152, COB-187, COB-204, COB-214, or combination thereof, and pharmaceutically acceptable salts and solvates thereof:

(COB-152)

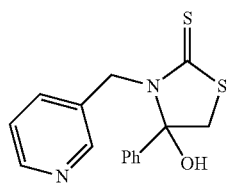

(COB-187)

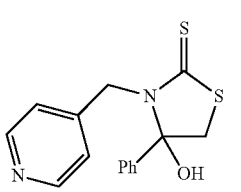

(COB-204)

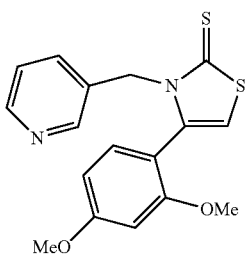

(COB-214)

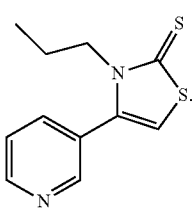

In a twenty-sixth aspect, a method for reducing the risk of developing non-alcoholic fatty liver disease (NAFLD) in a subject in need thereof is disclosed, the method including administering to the subject a therapeutically effective amount of at least one compound of General Formula (I) or (II):

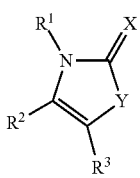 (I)

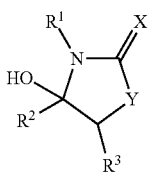 (II)

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In a twenty-seventh aspect, a method according to the twenty-sixth aspect is disclosed, wherein at least one compound of General Formula (I) or (II) is a thiazole 2-thione.

In a twenty-eighth aspect, a method according to the twenty-sixth or the twenty-seventh aspect is disclosed, wherein $R^3$ is —H; X is S; and Y is S in at least one compound of General Formula (I) or (II).

In a twenty-ninth aspect, a method for inhibiting excessive accumulation of fat in liver tissue is disclosed. The method includes contacting the liver tissue with a therapeutically effective amount of at least one compound of General Formula (I) or (II):

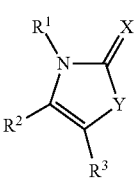 (I)

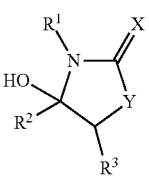 (II)

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is $Ph(CH_2)_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In a thirtieth aspect, a method according to the twenty-ninth aspect is disclosed, wherein at least one compound of General Formula (I) or (II) is effective to prevent accumulation of fat in the liver tissue above a normal level.

In a thirty-first aspect, a method according to the twenty-ninth or the thirtieth aspect is disclosed, wherein at least one compound of General Formula (I) or (II) is effective to reduce fat content in the liver tissue to at or below a normal level.

In a thirty-second aspect, a method according to the twenty-ninth to the thirty-first aspects is disclosed, wherein at least one compound of General Formula (I) or (II) is a thiazole 2-thione.

In a thirty-third aspect, a method according to the twenty-ninth to the thirty-second aspects is disclosed, wherein $R^3$ is —H; X is S; and Y is S in at least one compound of General Formula (I) or (II).

In a thirty-fourth aspect, a method according to the twenty-ninth to the thirty-third aspects is disclosed, wherein $R^1$ is chosen from $C_1$ to $C_4$ aliphatic or heteroaliphatic groups optionally substituted with one or more aryl groups, substituted aryl groups, heteroaryl groups, substituted heteroaryl groups, or combination thereof; $R^3$ is —H; X is S; and Y is S in at least one compound of General Formula (I) or (II).

In a thirty-fifth aspect, a method according to the twenty-ninth to the thirty-fourth aspects is disclosed, wherein $R^2$ is chosen from unsubstituted phenyl groups, substituted phenyl groups, or heteroaryl groups in which one or more ring atoms is N; $R^3$ is —H; X is S; and Y is S in at least one compound of General Formula (I) or (II).

In a thirty-sixth aspect, a method according to the twenty-ninth to the thirty-fifth aspects is disclosed, wherein $R^1$ is chosen from $C_1$ to $C_4$ aliphatic or heteroaliphatic groups optionally substituted with one or more aryl groups, substituted aryl groups, heteroaryl groups, substituted heteroaryl groups, or combination thereof; $R^2$ is chosen from unsubstituted phenyl groups, substituted phenyl groups, or heteroaryl groups in which one or more ring atoms is N; $R^3$ is —H; X is S; and Y is S in at least one compound of General Formula (I) or (II).

In a thirty-seventh aspect, a method according to the twenty-ninth to the thirty-sixth aspects is disclosed, wherein $R^1$ is chosen from $C_1$ to $C_4$ aliphatic groups optionally substituted with heteroaryl groups in which one or more ring atoms is N, or combination thereof; $R^2$ is chosen from unsubstituted phenyl groups, disubstituted phenyl groups, or heteroaryl groups in which one or more ring atoms is N; $R^3$ is —H; X is S; and Y is S in at least one compound of General Formula (I) or (II).

In a thirty-eighth aspect, a method according to the twenty-ninth to the thirty-seventh aspects is disclosed, wherein $R^1$ is chosen from methyl, ethyl, propyl, butyl, 2-propenyl,

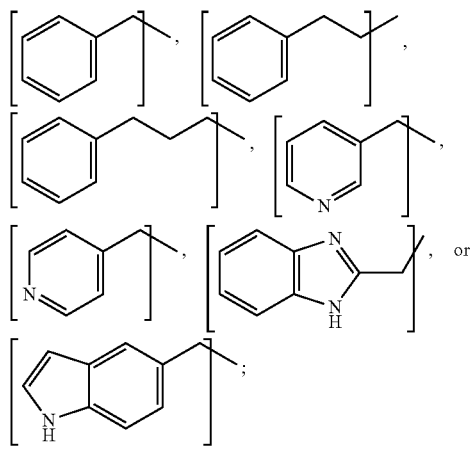

and $R^2$ is chosen from unsubstituted phenyl groups, 2,4-disubstituted phenyl groups, or heteroaryl groups in at least one compound of General Formula (I) or (II).

In a thirty-ninth aspect, a method according to the twenty-ninth to the thirty-eighth aspects is disclosed, wherein $R^1$ is chosen from

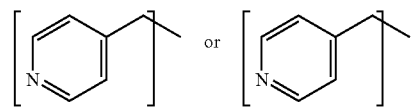

in at least one compound of General Formula (I) or (II).

In a fortieth aspect, a method according to the twenty-ninth to the thirty-eighth aspects is disclosed, wherein $R^2$ is

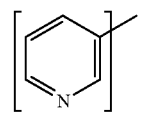

in at least one compound of General Formula (I) or (II).

In a forty-first aspect, a method according to the twenty-ninth to the fortieth aspects is disclosed, wherein at least one compound of General Formula (I) or (II) is chosen from COB-152, COB-187, COB-204, COB-214, or combination thereof, and pharmaceutically acceptable salts and solvates thereof:

(COB-152)

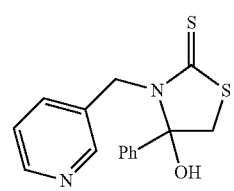

(COB-187)

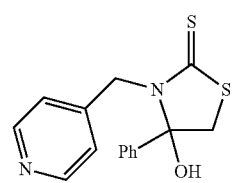

(COB-204)

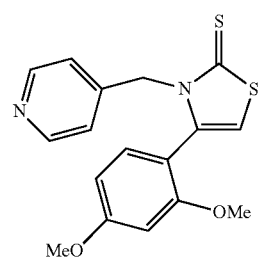

-continued

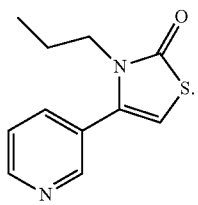

(COB-214)

In a forty-second aspect, a pharmaceutical composition for prevention or treatment of non-alcoholic fatty liver disease (NAFLD) is disclosed, the pharmaceutical composition including (1) a therapeutically effective amount of one or more of metformin, thiazolidinediones, or HMG-Co-A inhibitors; and (2) a therapeutically effective amount of at least one compound of General Formula (I) or (II):

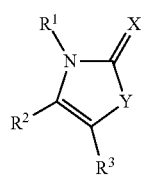

(I)

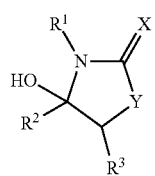

(II)

or a pharmaceutically-acceptable salt or solvate thereof, in which: $R^1$ is chosen from $C_1$ to $C_{10}$ aliphatic or heteroaliphatic groups, optionally substituted with one or more aryl groups, substituted aryl groups, heteroaryl groups, substituted heteroaryl groups, or combination thereof; $R^2$ is chosen from aryl groups, substituted aryl groups, heteroaryl groups, substituted heteroaryl groups, and coumarin; $R^3$ is chosen from —H, $C_1$ to $C_{10}$ aliphatic or heteroaliphatic groups, phenyl, or substituted phenyl, wherein the aliphatic or heteroaliphatic groups are optionally substituted with one or more phenyl groups, aryl groups, heteroaryl groups, substituted heteroaryl groups, or combination thereof; X is S or O; and Y is S or NH; with the proviso that when $R^2$ is phenyl and $R^3$ is —H, at least one of the following is true: (a) $R^1$ is a $C_1$ to $C_{10}$ aliphatic or heteroaliphatic group that is substituted with at least one substituted aryl group, at least one heteroaryl group, at least one substituted heteroaryl group, or combination thereof; (b) $R^1$ is hexyl; (c) $R^1$ is Ph(CH$_2$)$_n$—, where n is 2 or 3; or (d) $R^1$ is a $C_1$ to $C_{10}$ heteroaliphatic group, optionally substituted with one or more aryl groups, substituted aryl groups, heteroaryl groups, substituted heteroaryl groups, or combination thereof.

In a forty-third aspect, a pharmaceutical composition according to the forty-second aspect is disclosed, further including a pharmaceutically acceptable carrier.

In a forty-fourth aspect, a device including a reservoir of the pharmaceutical composition according to any of the forty-second or the forty-third aspect is disclosed.

In a forty-fifth aspect, a device according to the forty-fourth embodiment is disclosed, wherein the reservoir is a vial and the device is a syringe.

In a forty-sixth aspect, a method for prevention and/or treatment of non-alcoholic fatty liver disease (NAFLD) is disclosed; the method including administering to the subject a therapeutically effective amount of the pharmaceutical composition according to any of the forty-second to the forty-third aspects.

In a forty-seventh aspect, a method according to the forty-sixth aspect is disclosed, wherein at least one compound of General Formula (I) or (II) is formulated into a dosage form selected from the group consisting of tablets, capsules, granules, pills, injections, solutions, emulsions, suspensions, and syrups.

EXAMPLES

The following non-limiting examples illustrate the synthesis of the imidazole and/or thiazole compounds having General Formulae (I) and (II) and also illustrate methods of the present disclosure. The exemplary compounds synthesized and/or characterized in the Examples to follow should be understood to be illustrative in nature and in no regard limiting to the scope of the General Formulas provided or of the methods described herein.

Example 1: Synthesis of Imidazole and/or Thiazole Compounds Having General Formula (I)

Imidazole and/or Thiazole Compounds having General Formula (I):

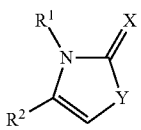

(I)

in which X=O or S; Y=NH; $R^1$ and $R^2$, as described above, may be synthesized by adding an isothiocyanate or isocyanate of formula (1a):

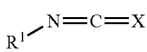

(1a)

(100 mol %, X=O or S) and Et$_3$N (50 mol. %) to an EtOH (0.01 M) solution of a hydrochloride of a methylamino ketone of formula (1b) (100 mol. %):

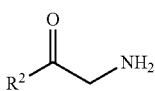

(1b)

to form a reaction mixture. The reaction mixture is heated at 140° C. for 20 min using microwave irradiation. The microwave irradiation may be carried out using an Initiator Biotage Microwave Synthesizer, for example, operating at 400 W, 2.45 GHz. The solvent is then removed by means of rotary evaporation, and the product is isolated by flash chromatography. The purification is performed by eluting the crude product with 5% to 10% ethyl acetate (EtOAc) in CH$_2$Cl$_2$ for imidazole-2-thiones (X=S) or with EtOAc for imidazole-2-ones (X=O). Yields for this general synthetic method are typically in the range of from 15% to 65%.

Additionally, compounds having General Formula (II):

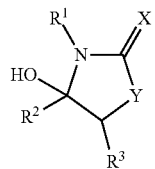

(II)

in which X=O or S; Y=NH; and $R^1$, $R^2$, and $R^3$ are as described above, may be synthesized by the above method by heating the reaction mixture at about 140° C. using means other than microwave irradiation. Without intent to be bound by theory, it is believed that microwave irradiation increases the rate of hydroxyl elimination, so as to favor formation of the compounds of General Formula (I) when the microwave irradiation is applied during heating.

Example 2: Synthesis of Imidazole and/or Thiazole Compounds Having General Formula (II)

Imidazole and/or Thiazole Compounds having General Formula (II):

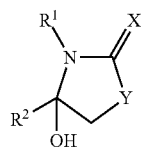

(II)

in which X=S; Y=S; and $R^1$ and $R^2$, as described above, may be synthesized by adding carbon disulfide ($CS_2$; 150 mol. %) and $K_2CO_3$ (50 mol. %) to a solution of an amine of the formula (2a):

$R^1$—$NH_2$  (2a)

(150 mol. %) in $H_2O$:EtOH (0.2 M, 1:1) and then adding a 2-bromoketone derivative of formula (2b):

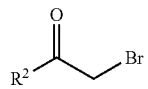

(2b)

(100 mol %) to form a reaction mixture. The reaction mixture is stirred in an open flask at room temperature (25° C.±2° C.) for 1 hour to 3 hours. Then, the crude reaction mixture is extracted with ethyl acetate (EtOAc; 3×10 mL), and the combined organic layers are dried over $MgSO_4$ and filtered. The solvent is evaporated by rotary evaporation. The product is isolated by flash chromatography using 10%-20% EtOAc in hexanes. In some cases, some products may precipitate during the reaction. In such cases the product may be isolated by filtration, washed thoroughly with solvent (EtOH:$H_2O$, 1:1), then dried.

Compounds having General Formula (II), in which X=O; Y=S; and $R^1$, $R^2$, and $R^3$ are as described above may be synthesized by the above method by replacing the carbon disulfide ($CS_2$) with carbonyl sulfide (C=O=S; 150 mol. %).

Example 3: Synthesis of Imidazole and/or Thiazole Compounds Having General Formula (I)

Imidazole and/or Thiazole Compounds having General Formula (I), in which X=O or S; Y=S; and $R^1$ and $R^2$ are as described above, may be synthesized by dehydrating a compound having General Formula (II) prepared according to Synthetic Example 2 or by any other suitable method, in which groups $R^1$, $R^2$, X, and Y of the compound having General Formula (II) are the same as those in the desired compound having General Formula (I).

To perform the dehydration, to an ethanol solution containing 1 molar equivalent of a compound of General Formula (II), 1.2 molar equivalents of hydrochloric acid (1 M solution in ethyl acetate) are added to form a reaction mixture. The reaction mixture is submitted to microwave irradiation for 20 min at 140° C. The solvent is removed by rotary evaporation. The crude product is purified by flash chromatography.

Example 4: Synthesis of Imidazole and/or Thiazole Exemplary Compounds

Except where noted otherwise, imidazole and/or thiazole compounds having General Formula (I) or General Formula (II) were prepared according to one of the Synthetic Examples 1-3 above. Proton NMR ($^1$H-NMR) spectra were obtained using a Brüker Avance (300 MHz) spectrometer. Carbon NMR ($^{13}$C-NMR) spectra were obtained at 75 MHz. Chemical shifts are reported in ppm on the δ scale relative to deuterated chloroform ($CDCl_3$) as an internal standard. Data are reported as follows: chemical shift, multiplicity (s=singlet, d=doublet, t=triplet, q=quartet, qt=quintet, st=sextet, m=multiplet), coupling constant in Hz, integration. HPLC analyses were performed with a Shimadzu LC-10AT machine equipped with a UV detector by employing a reverse-phase Discovery-C8 (15 cm×4.6 mm×5 μm; Supelco) column eluting with methanol (MeOH) in $H_2O$ at 1 mL/min flow using the following protocol: 50% MeOH/$H_2O$, 8 min; 90% MeOH/$H_2O$, 5 min; 90% MeOH/$H_2O$, 5 min; 50% MeOH/$H_2O$, 3 min.

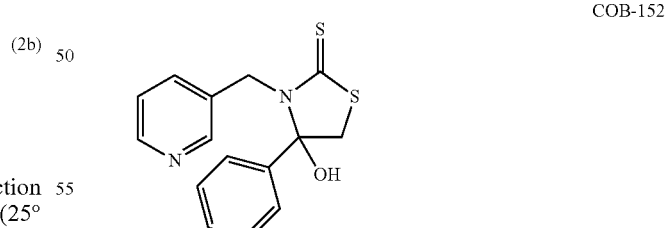

COB-152

COB-152 was prepared according to Synthetic Example 2. Based on 33.8 mg of product recovered, the yield was 89%. For the COB-152, the following data were obtained: 33.8 mg (89%); $R_f$ 0.4 (60% EtOAc in hexanes); $t_R$=11.78 min; $^1$H NMR (DMSO-$d_6$, 300 MHz) δ 8.36-8.35 (m, 2H, Py), 7.86 (s, 1H, OH), 7.59 (dt, J=7.9 Hz, 1H, Py), 7.39-7.34 (m, 5H, Ph), 4.80 (d, J=15 Hz, 1H, PyCHH), 4.52 (d, J=15 Hz, 1H, PyCHH), 3.74 (d, J=12 Hz, 1H, SCHH), 3.68 (d, J=12 Hz, 1H, SCHH); $^{13}$C NMR (DMSO-$d_6$, 75 MHz) δ

195.8, 149.0, 147.8, 140.5, 135.3, 132.3, 128.9, 128.5, 125.6, 122.9, 100.2, 46.4, 42.4.

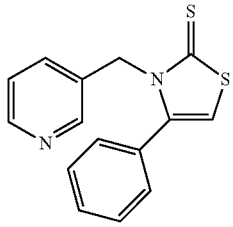

COB-153

COB-153 was prepared from COB-152 according to Synthetic Example 3. Based on 23.4 mg of product recovered, the yield was 90%. For the COB-153, the following data were obtained: Was prepared from COB-152 following the general procedure to afford 23.4 mg (90%). $R_f$ 0.46 (60% EtOAc in hexanes); $t_R$=9.25 min; $^1$H NMR (CDCl$_3$, 300 MHz) δ 8.38 (dd, J=1.5, 4.8 Hz, 1H, Py), 7.94 (d, J=1.6 Hz, 1H, Py), 7.43-7.29 (m, 4H, Ph), 7.10-7.03 (m, 3H, Ph, Py), 6.43 (s, 1H, CH), 5.36 (s, 2H, PyCH$_2$); $^{13}$C NMR (CDCl$_3$, 75 MHz) δ 189.4, 149.2, 148.9, 144.5, 135.5, 131.4, 130.5, 130.45, 129.6, 129.2, 123.6, 109.3, 48.5.

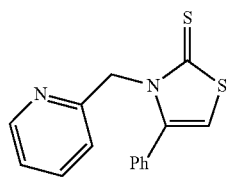

COB-176

COB-176 was prepared according to Synthetic Example 2 on a 1.5-mmol scale. Based on 104 mg of product recovered, the yield was 23%. For the COB-176, the following data were obtained: $R_f$ 0.23 (10% MeOH in EtOAc); $t_R$=2.76 min; $^1$H NMR (CDCl$_3$, 300 MHz) δ 8.75 (d, J=2 Hz, 1H, Ar), 8.53 (dd, J=1.5, 5 Hz, 1H, Ar), 8.28 (d, J=1.5 Hz, 1H, Ar), 8.00 (dd, J=1.3, 4.8 Hz, 1H, Ar), 7.77-7.20 (m, 2H, Ar), 7.28 (dd, J=4.8, 7.9 Hz, 1H, Ar), 7.19 (s, 1H), 7.03 (dd, J=4.9, 7.8 Hz, 1H, Ar), 5.7 (d, J=14.9 Hz, 1H, NCHH), 4.26 (d, J=14.9 Hz, 1H, NCHH), 3.74 (d, J=12.2 Hz, 1H, SCHH), 3.54 (d, J=12.2 Hz, 1H, SCHH); $^{13}$C NMR (CDCl$_3$, 75 MHz) δ 196.9, 150.4, 149.0, 147.6, 147.3, 138.3, 136.7, 134.0, 133.6, 123.9, 123.8, 100.0, 47.0, 43.5.

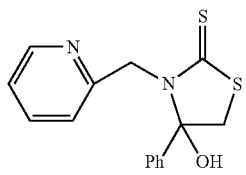

COB-180

COB-180 was prepared according to Synthetic Example 2 on a 1.88-mmol scale. Based on 300 mg of product recovered, the yield was 84%. For the COB-180, the following data were obtained: $R_f$ 0.34 (20% EtOAc in hexanes); $t_R$=10.8 min; $^1$H NMR (DMSO-d$_6$, 300 MHz) δ 8.42 (d, J=4.8 Hz, 1H, Ar), 8.27 (s, 1H, OH), 7.75-7.70 (m, 1H, Ar), 7.51-7.48 (m, 2H, Ar), 7.42-7.21 (m, 5H, Ar), 4.95 (d, J=16.2 Hz, 1H, NCHH), 4.38 (d, J=16.2 Hz, 1H, NCHH), 3.79 (d, J=12.1 Hz, 1H, SCHH), 3.71 (d, J=12.1 Hz, 1H, SCHH); $^{13}$C NMR (DMSO-d$_6$, 75 MHz) δ 196.6, 155.2, 148.1, 140.8, 136.7, 128.8, 128.6, 125.8, 122.2, 122.1, 99.8, 50.7, 43.1.

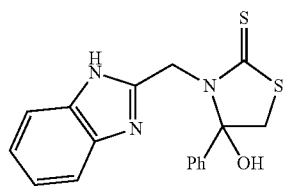

COB-189

COB-189 was prepared from COB-180 according to Synthetic Example 3 on a 0.5-mmol scale. Based on 129.4 mg of product recovered, the yield was 91%. For the COB-189, the following data were obtained: $R_f$ 0.16 (20% EtOAc in hexanes); $t_R$=6.05 min; $^1$H NMR (CDCl$_3$, 300 MHz) δ 8.460-8.39 (m, 1H, Ar), 7.56-7.50 (m, 1H, Ar), 7.35-6.98 (m, 7H, Ar), 6.47 (s, 1H, CH), 5.37 (s, 2H, NCH$_2$); $^{13}$C NMR (CDCl$_3$, 75 MHz) δ 189.2, 155.0, 149.7, 145.4, 136.7, 130.8, 130.1, 129.6, 129.0, 122.5, 121.7, 52.8.

COB-183

COB-183 was prepared according to Synthetic Example 2 on a 1.88-mmol scale. Based on 214 mg of product recovered, the yield was 50%. For the COB-183, the following data were obtained: $R_f$ 0.16 (20% EtOAc in hexanes); $t_R$=12.28 min; $^1$H NMR (DMSO-d$_6$, 300 MHz) δ 12.39 (s, 1H, NH), 8.76 (s, 1H, OH), 7.61-7.37 (m, 7H, Ar), 7.18-7.16 (m, 2H, Ar), 5.18 (d, J=16.5 Hz, 1H, NCHH), 4.40 (d, J=16.5 Hz, 1H, NCHH), 3.80 (d, J=12 Hz, 1H, SCHH), 3.70 (d, J=12 Hz, 1H, SCHH); $^{13}$C NMR (DMSO-d$_6$, 75 MHz) δ 198.2, 150.0, 140.5, 129.0, 128.6, 126.1, 121.9, 99.7, 43.9, 43.5.

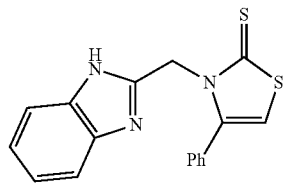

COB-192

COB-192 was prepared from COB-183 according to Synthetic Example 3 on a 0.07-mmol scale. Based on 13 mg of product recovered, the yield was 63%. For the COB-192, the following data were obtained: $R_f$ 0.4 (5% EtOAc in toluene); $t_R$=6.95 min; $^1$H NMR (DMSO-d$_6$, 300 MHz) δ 12.4 (s, 1H, NH), 7.58-7.55 (m, 3H, Ar), 7.45-7.38 (m, 4H, Ar), 7.16-7.11 (m, 3H, Ar and SCH), 5.41 (s, 2H, NCH$_2$); $^{13}$C NMR (DMSO-d$_6$, 75 MHz) δ 188.0, 148.9, 144.5, 142.9, 134.1, 130.4, 129.8, 129.2, 128.7, 122.1, 121.2, 118.6, 111.2, 109.6, 45.7.

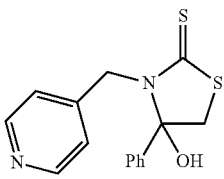

COB-187

COB-187 was prepared according to Synthetic Example 2 on a 1.88-mmol scale. Based on 70 mg of product recovered, the yield was 20%. For the COB-187, the following data were obtained: R$_f$ 0.3 (10% EtOAc in toluene); t$_R$=8.59 min; $^1$H NMR (DMSO-d$_6$, 300 MHz) δ 8.39-8.37 (d, 2H, Ar), 7.84 (s, 1H, OH), 7.39-7.35 (m, 5H, Ar), 7.16-7.15 (m, 2H, Ar), 4.80 (d, J=16.1 Hz, 1H, NCHH), 4.51 (d, J=16.1 Hz, 1H, NCHH), 3.78 (d, J=12.1 Hz, 1H, SCHH), 3.71 (d, J=12.1 Hz, 1H, SCHH); $^{13}$C NMR (DMSO-d$_6$, 75 MHz) δ 196.0, 148.9, 145.6, 140.5, 128.9, 128.5, 125.6, 122.3, 100.1, 47.8, 42.4.

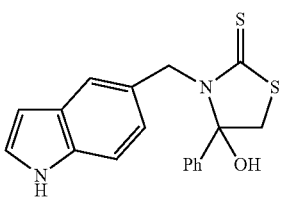

COB-188

COB-188 was prepared according to Synthetic Example 2 on a 1.88-mmol scale. Based on 107 mg of product recovered, the yield was 25%. For the COB-188, the following data were obtained: R$_f$ 0.25 (10% EtOAc in toluene); t$_R$=14.41 min; $^1$H NMR (CDCl$_3$, 300 MHz) δ 8.91 (s, 1H, NH), 7.45-7.35 (m, 5H, Ph), 7.31-7.14 (m, 5H, Ar), 6.47 (s, 1H, OH), 5.82 (d, J=14.5 Hz, 1H, NCHH), 4.21 (d, J=14.5 Hz, 1H, NCHH), 3.61 (d, J=12.1 Hz, 1H, SCHH), 3.38 (d, J=12.1 Hz, 1H, SCHH); $^{13}$C NMR (CDCl$_3$, 75 MHz) δ 198.4, 139.6, 135.4, 129.3, 128.9, 127.9, 127.8, 126.2, 124.9, 122.8, 121.2, 111.5, 102.9, 100.8, 49.6, 44.0.

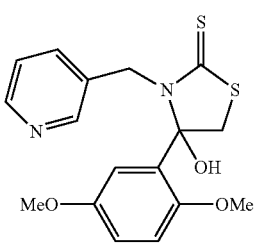

COB-197

COB-197 was prepared according to Synthetic Example 2 on a 3-mmol scale. Based on 450 mg of product recovered, the yield was 62%. For the COB-197, the following data were obtained: R$_f$ 0.4 (60% EtOAc in hexanes); t$_R$=5.33 min; $^1$H NMR (DMSO-d$_6$, 300 MHz) δ 8.27-8.25 (m, 1H, Ar), 8.09 (d, 1H, Ar), 7.87 (s, 1H, OH), 7.42 (d, 1H, Ar), 7.25 (d, 1H, Ar), 7.11-7.07 (m, 1H, Ar), 6.80-6.77 (m, 1H, Ar), 6.50 (d, 1H, Ar), 4.91 (d, J=15.3 Hz, 1H, NCHH), 4.38 (d, J=15.3 Hz, 1H, NCHH), 3.85 (d, J=12 Hz, 1H, SCHH), 3.72 (s, 3F1, OCH$_3$), the signal corresponding to the second MeO overlaps with the water peak, 3.28 (d, J=12 Hz, 1H, SCHH); $^{13}$C NMR (DMSO-d$_6$, 75 MHz) δ 194.4, 150.7, 148.1, 147.1, 145.6, 133.5, 130.3, 126.3, 120.5, 113.2, 111.3, 109.9, 95.4, 53.6, 53.4 43.8.

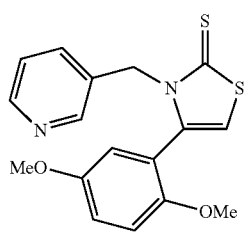

COB-203

COB-203 was prepared from COB-197 according to Synthetic Example 3 on a 0.27-mmol scale. Based on 84 mg of product recovered, the yield was 90%. For the COB-203, the following data were obtained: R$_f$ 0.32 (60% EtOAc in hexanes); t$_R$=4.13 min (LCMS); $^1$H NMR (CDCl$_3$, 300 MHz) δ 8.33 (d, 1H, Ar), 7.91 (s, 1H, Ar), 7.41 (d, 1H, Ar), 7.08-7.04 (m, 1H, Ar), 6.93-6.89 (in, 1H, Ar), 6.79 (d, 1H, Ar), 6.39-6.38 (m, 2H, Ar and CH), 5.26 (s, 2H, CH$_2$), 3.58 (s, 3H, OMe), 3.22 (s, 3H, OMe).

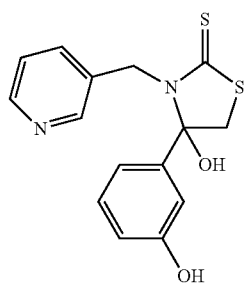

COB-198

COB-198 was prepared according to Synthetic Example 2 on a 1.5-mmol scale. Based on 69.9 mg of product recovered, the yield was 22%. For the COB-198, the following data were obtained: R$_f$ 0.3 (60% EtOAc in hexanes); t$_R$=5.49 min; $^1$H NMR (DMSO-d$_6$, 300 MHz) δ 8.37-8.35 (m, 2H, Ar and ArOH), 7.82 (s, 1H, OH), 7.63-7.60 (m, 1H, Ar), 7.27-7.13 (m, 3H, Ar), 6.826.71 (m, 3H, Ar), 4.85 (d, J=15.3 Hz, 1H, NCHH), 4.43 (d, J=15.3 Hz, 1H, NCHH), the SCH$_2$ peaks overlap with the water peak. The compound was not pure after three purifications according to HPLC (89% purity).

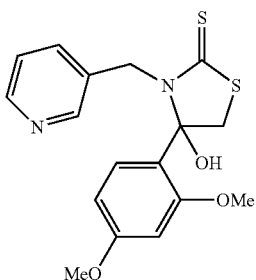

COB-199

COB-199 was prepared according to Synthetic Example 2 on a 1.5-mmol scale. Based on 203 mg of product recovered, the yield was 56%. For the COB-199, the following data were obtained: $R_f$ 0.3 (60% EtOAc in hexanes); $t_R$=3.39 min (LCMS); $^1$H NMR (DMSO-$d_6$, 300 MHz) δ 8.25 (dd, 1H, Ar), 8.07 (d, 1H, Ar), 7.73 (s, 1H, OH), 7.56 (d, 1H, Ar), 7.40 (dt, 1H, Ar), 7.12-7.07 (m, 1H, Ar), 6.53 (dd, 1H, Ar), 6.08 (d, 1H, Ar), 4.91 (d, J=15.3 Hz, 1H, NCHH), 4.31 (d, J=15.3 Hz, 1H, NCHH), 3.83 (d, J=12 Hz, 1H, SCHH), 3.71 (s, 3H, OCH$_3$), 3.43 (s, 3H, OCH$_3$), 3.25 (d, J=12 Hz, 1H, SCHH); $^{13}$C NMR (DMSO-$d_6$, 75 MHz) δ 196.0, 161.5, 157.1, 135.4, 132.4, 122.3, 119.9, 109.9, 97.6, 55.3, 40.3.

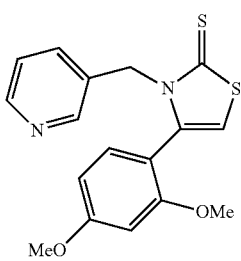

COB-204

COB-204 was prepared from COB-199 according to Synthetic Example 3 on a 0.28-mmol scale. Based on 81 mg of product recovered, the yield was 87%. For the COB-204, the following data were obtained: $R_f$ 0.32 (60% EtOAc in hexanes); $t_R$=4.03 min (LCMS); $^1$H NMR (CDCl$_3$, 300 MHz) δ 8.40 (d, 1H, Ar), 7.99 (s, 1H, Ar), 7.53 (d, 1H, Ar), 7.28-7.11 (m, 1H, Ar), 6.85 (d, 1H, Ar), 6.45 6.41 (m, 3H, Ar and CH), 5.29 (s, 2H, CH$_2$), 3.82 (s, 3H, OMe), 3.59 (s, 3H, OMe).

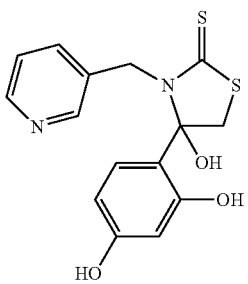

COB-200

COB-200 was prepared according to Synthetic Example 2 on a 1.5-mmol scale. Based on 131 mg of product recovered, the yield was 40%. For the COB-200, the following data were obtained: $R_f$ 0.11 (60% EtOAc in hexanes); $t_R$=2.75 min (LCMS); $^1$H and $^{13}$C NMR were not optimal, but based on the LCMS (96.9%), the compound was considered clean enough to be sent for tests.

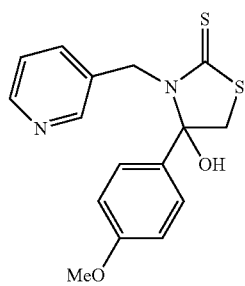

COB-201

COB-201 was prepared according to Synthetic Example 2 on a 1.6-mmol scale. Based on 153 mg of product recovered, the yield was 46%. For the COB-201, the following data were obtained: $R_f$ 0.28 (60% EtOAc in hexanes); $t_R$=3.56 min (LCMS); $^1$H NMR (DMSO-$d_6$, 300 MHz) δ 8.36-8.35 (m, 2H, Ar), 7.75 (s, 1H, OH), 7.58 (d, 1H, Ar), 7.32-7.21 (m, 3H, Ar), 6.89 (d, 2H, Ar), 4.77 (d, J=15.4 Hz, 1H, NCHH), 4.52 (d, J=15.4 Hz, 1H, NCHH), 3.37-3.68 (m, 5H, SCH$_2$ and OCH$_3$); $^{13}$C NMR (DMSO-$d_6$, 75 MHz) δ 195.6, 159.5, 148.9, 147.7, 135.3, 132.4, 132.35, 127.0, 122.8, 113.7, 100.1, 55.2, 46.9, 42.5.

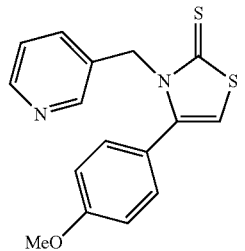

COB-206

COB-206 was prepared from COB-201 according to Synthetic Example 3 on a 0.18-mmol scale. Based on 39 mg of product recovered, the yield was 69%. For the COB-206, the following data were obtained: $R_f$ 0.26 (60% EtOAc in hexanes); $t_R$=4.15 min (LCMS); $^1$H NMR (CDCl$_3$, 300 MHz) δ 8.40 (d, 1H, Ar), 8.0 (s, 1H, Ar), 7.43 (d, 1H, Ar), 7.13-7.08 (m, 1H, Ar), 6.95 (d, 2H, Ar), 6.82 (d, 2H, Ar), 6.39 (s, 1H, CH), 5.35 (s, 2H, CH$_2$), 3.76 (s, 3H, OMe).

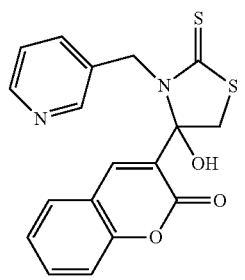

COB-202

COB-202 was prepared according to Synthetic Example 2 on a 1.5-mmol scale. Based on 114 mg of product recovered, the yield was 35%. For the COB-202, the following data were obtained: $R_f$ 0.22 (60% EtOAc in hexanes); $t_R$=3.12 min (LCMS); $^1$H NMR (DMSO-$d_6$, 300 MHz) δ 8.41 (s, 1H, OH), 8.28-8.23 (m, 3H, Ar), 7.87 (dd, 1H, Ar), 7.66-7.56 (m, 2H, Ar), 7.41-7.36 (td, 1H, Ar), 7.28 (d, 1H, Ar), 7.08 (dd, 1H, CH), 5.08 (d, J=15.5 Hz, 1H, NCHH), 4.56 (d, J=15.5 Hz, 1H, NCHH), 3.98 (d, J=12.3 Hz, 1H, SCHH), 3.28 (d, J=12.3 Hz, 1H, SCHH) this signal overlaps with the signal for water; $^{13}$C NMR was recorded, but the signal was weak such that only six carbon are observed.

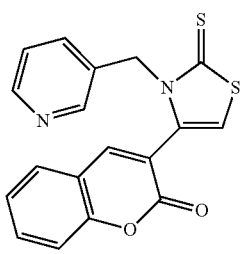

COB-205

COB-205 was prepared from COB-202 according to Synthetic Example 3 on a 0.13-mmol scale. Based on 33.4 mg of product recovered, the yield was 70%. For the COB-205, the following data were obtained: $R_f$ 0.25 (60% EtOAc in hexanes); $t_R$=3.46 min (LCMS); $^1$H NMR (CDCl$_3$, 300 MHz) δ 8.34 (s, 1H, Ar), 8.20 (s, 1H, Ar), 7.59-7.43 (m, 2H, Ar), 7.34 (s, 1H, Ar), 7.33-7.30 (m, 2H, Ar), 7.25-7.06 (m, 1H, Ar), 6.59 (s, 1H, CH), 5.51 (s, 2H, CH$_2$).

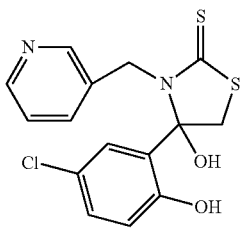

COB-222

COB-222 may be prepared according to Synthetic Example 2.

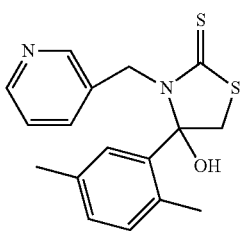

COB-223

COB-223 may be prepared according to Synthetic Example 2.

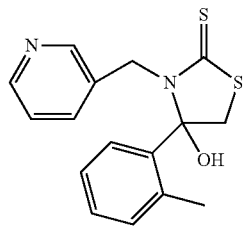

COB-224

COB-224 may be prepared according to Synthetic Example 2.

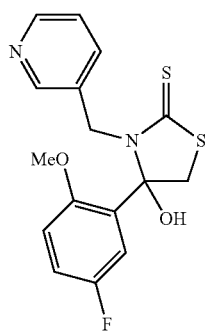

COB-225

COB-225 may be prepared according to Synthetic Example 2.

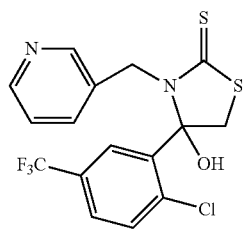

COB-226

COB-226 may be prepared according to Synthetic Example 2.

Example 5: Preparation of Pharmaceutical Compositions

Composition Administration. Means of administering active agents (i.e., active ingredients) according to embodiments herein, such as, e.g., means of administering the imiazole an/or thiazole compounds as previously described, include, but are not limited to, oral, sublingual, intravenous, intramuscular, intraperitoneal, percutaneous, intranasal, intrathecal, subcutaneous, or enteral. Local administration to the afflicted site may be accomplished through means known in the art, including, but not limited to, topical application, injection, infusion and implantation of a porous device in which the active agent(s) or compositions described herein are contained. Accordingly, the active agents described herein will generally be administered as a pharmaceutical composition including one or more active agents described herein in combination with a pharmaceutically acceptable excipient and other formulational aids.

Formulational Aids. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Alternatively, one may incorporate or encapsulate the active agents described herein in a suitable polymer matrix or membrane, thus providing a sustained-release device suitable for implantation near the site to be treated locally. Other devices include indwelling catheters and devices such as the Alzet® minipump. Opthalmic preparations may be formulated using commercially available vehicles such as Sorbi-care® (Allergan), Neodecdron® (Merck, Sharp & Dohme), Lacrilube®, and the like. Further, one may provide the active agents described herein in bulking agents, for example human serum albumin, sucrose, mannitol, and the like. A thorough discussion of pharmaceutically acceptable excipients is available in Remington's Pharmaceutical Sciences I (Mack Pub. Co.), incorporated herein by reference.

Oral/Parenteral Administration. The active agents and pharmaceutical compositions according to embodiments herein can be administered both orally and parenterally in accordance with conventional procedures. The amount of active compound required to treat any particular disease and/or disorder will, of course, vary depending upon the nature and severity of the disorder, the age and condition of the subject, and other factors readily determined by one of ordinary skill in the art. Active agents are administered in dosage units, preferably divided dosage units, containing the active agent with a suitable physiologically acceptable carrier or excipient, many of which are well known to those in the art and are described above. The dosage units can be in the form of a liquid preparation, e.g., solutions, suspensions, dispersions, or emulsions, or they may be in solid form such as pills, tablets, capsules or the like. Compositions in unit dosage form, i.e., pharmaceutical compositions which are available in a pre-measured form suitable for single dose administration without requiring that the individual dosage be measured out by the user, for example, pills, tablets, capsules, or ampules are methods of administration of the active agents described herein.

Specific Formulations. Pharmaceutical compositions in dosage unit form may include an amount of compound which provides from about 0.05 mg to about 60 mg, preferably from about 0.05 mg to about 20 mg, of active agent per day. To produce dosage units for peroral administration, the active agent according to embodiments herein or a salt thereof is combined, e.g., with solid powdered carriers such as lactose, sucrose, mannitol; starches such as potato starch, corn starch or amylopectin, as well as laminaria powder and citrus pulp powder; cellulose derivatives of gelatin, also lubricants such as magnesium or calcium sterate of polyethylene glycols (carbowaxes) of suitable molecular weights may be added, to form compressed tablets or core tablets for sugar coating. The latter are coated, for example, with concentrated sugar solutions which, e.g., can contain gum arabic, talcum and/or titinium dixoide, or they are coated with a lacquer dissolved in easily volatile organic solvents or mixture of organic solvents. Dyestuffs can be added to these coatings, for example, to distinguish between different contents of active agent. Capsules useful herein include, for example, soft gelatin capsules (pearl-shaped closed capsules), geltabs, other capsules which consist, for example, of a mixture of gelatin and glycerin and contain, e.g., mixtures of the active agents or a pharmaceutically acceptable salt and/or solvate thereof with solid, powdered carriers such as, e.g., lactose, sucrose, sorbital, mannitol; starches such as potato starch corn starch or amylopectin, cellulose derivatives or gelatin, as well as magnesium sterate or steric acid. Suppositories are employed as dosage units for rectal application. These consist of a combination of the active agent or a pharmaceutically acceptable salt and/or solvate thereof with a neutral fatty base, or also gelatin rectal capsules can be employed which consist of a combination of the active agent or a suitable salt thereof with polyethylene glycols (carbowaxes) of suitable molecular weight.

Ampoules for parenteral administration, particularly intramuscular administration, preferably contain an active agent or a water soluble salt thereof and suitable stabilizing agents, and, if necessary, buffer substances in aqueous solution. Anti-oxidizing agents such as sodium bisulfite, sodium sulfite, ascorbic acid or Rongalit (formaldehyde-sodium bisulfite compound), and the like are suitable as stabilizing agents either alone or combined, in total concentrations from about 0.01% to about 0.05% by weight of the composition. Because of its ability to form chelates, ascorbic acid has an additional stabilizing effect; in this function it can also be replaced by other chelate-formers. The best suitability of the active agent is attained, e.g., by mixtures in suitable ratio of sodium sulfite, sodium bisulfate and/or ascorbic acid, or by the addition of other buffer substances such as citric acid and/or salts thereof. In addition, the ampoules can contain a slight amount of a preservative.

Useful pharmaceutical formulations for administration of the active agents according to embodiments herein may be illustrated below. They are made using conventional techniques.

Capsules
Active Agent/Ingredient 0.05 to 20 mg
Lactose 20-100 mg
Corn Starch U.S.P. 20-100 mg
Aerosolized silica gel 2-4 mg
Magnesium stearate 1-2 mg
Tablets
Active Agent/Ingredient 0.05 to 20 mg
Microcrystalline cellulose 50 mg
Corn Starch U.S.P. 80 mg
Lactose U.S.P. 50 mg
Magnesium stearate U.S.P. 1-2 mg
The tablets can be sugar coated according to conventional art practices. Colors may be added to the coating.
Chewable Tablets
Active Agent/Ingredient 0.05 to 20 mg
Mannitol, N.F. 100 mg
Flavor 1 mg
Magnesium stearate U.S.P. 2 mg
Suppositories
Active Agent/Ingredient 0.05 to 20 mg
Suppository base 1900 mg
Liquid
Active Agent/Ingredient 2.0 percent
Polyethylene glycol 300, N.F. 10.0 percent
Glycerin 5.0 percent
Sodium bisulfite 0.02 percent
Sorbitol solution 70%, U.S.P. 50 percent
Methylparaben, U.S.P. 0.1 percent Propylparaben, U.S.P. 0.2 percent
Distilled water, U.S.P. (q.s.) 100.0 cc
Injectable
Active Agent/Ingredient 0.05 to 60 mg
Polyethylene glycol 600 1.0 cc
Sodium bisulfite, U.S.P. 0.4 mg
Water for injection, U.S.P. (q.s.) 2.0 cc

Example 6: Evaluation of Onset of NAFLD in C57BL/6J Mice Fed High Fat Diet

Experimental Protocol. C57BL/6J mice (i.e., a mouse model of obesity-induced insulin resistance and Type 2 Diabetes Mellitus) were placed on a high-fat diet (hereinafter, "HFD") containing 60% fat (by % Kcal) (Diet #D12492, Research Diets, Inc., New Brunswick, N.J.) for 8 weeks. Three of such mice were euthanized each week during this 8-week period for evaluation of NAFLD. Mice fed a low fat diet (hereinafter, "LFD") containing 10% fat (by % Kcal) (Diet #D12450B, Research Diets) served as a control. More particularly, two mice fed the LFD served as a control (and were euthanized) for each week that the mice fed the HFD were euthanized over the 8 week period. The following Table further illustrates the experimental design:

TABLE 3

Onset of NAFLD Experimental Protocol

| Time (Weeks) | Total Number of Mice | Number of Mice Euthanized for Fatty Liver Evaluation |
| --- | --- | --- |
| 0 | 85 | 5 (3 HFD + 2 LFD mice) |
| 1 | 80 | 5 (3 HFD + 2 LFD mice) |
| 2 | 75 | 5 (3 HFD + 2 LFD mice) |
| 3 | 70 | 5 (3 HFD + 2 LFD mice) |
| 4 | 65 | 5 (3 HFD + 2 LFD mice) |
| 5 | 60 | 5 (3 HFD + 2 LFD mice) |
| 6 | 55 | 5 (3 HFD + 2 LFD mice) |
| 7 | 50 | 5 (3 HFD + 2 LFD mice) |
| 8 | 45 | 5 (3 HFD + 2 LFD mice) |

As previously described, NAFLD may be detected macroscopically (i.e., via the naked eye), microscopically (i.e., via tissue sections of the liver, e.g., imaging procedures and/or liver biopsy), and/or molecularly (i.e., using molecular assays to quantify liver triglycerides, e.g., blood testing). NAFLD was evaluated in the liver of the HFD and LFD mice macroscopically, microscopically, and molecularly. More specifically, following euthanasia, the liver of each mouse was removed, weighed, and photographs taken thereof for macroscopic and/or gross observation of NAFLD. Then, the liver of each mouse was split in half, wherein one half was used for microscopic analysis (i.e., hematoxylin and eosin staining) of NAFLD and the remaining half was used for molecular analysis of NAFLD (i.e., quantification of triglycerides).

Quantification of triglycerides of the middle, right, and left lobes was performed to ensure that accumulation (or lack thereof) of triglycerides was similar in each lobe of the liver and to ensure that a representative analysis of triglyceride accumulation in the liver as a whole was assessed. The caudate lobe was excluded since the caudate lobe is very small compared to the middle, right, and left lobes. Triglycerides were quantified in accordance with the following general protocol, based upon the Salmon and Flatt Method of Liver Saponification. 50-100 mg of liver tissue was placed into an Eppendorf tube and weighed. Equal volume per weight of 3 M KOH (in 65% EtOH) was added to the tube and vortexed. The tube was placed at 70° C. for 1 hr to activate digestion. The tubes were vortexed every 15 minutes. The tube was set at room temperature overnight to allow for complete digestion, and was vortexed periodically. The sample was diluted to a final concentration of 100 mg of liver tissue per 600 µl fluid; the sample was diluted by adding 2 M Tris-HCl (un-pHed) to a final concentration of 50 mM. Where a second dilution was required, the sample was diluted using 50 mM Tris-HCl (pH 7.5). Triglycerides-GPO (0.5 mL, liquid; Pointe Scientific Cat. No. T7532-500; Fisher Scientific, Pittsburgh, Pa.) were aliquoted into Eppendorf tubes and warmed in a 37° C. water bath for 5-10 minutes. Glycerol standards (0, 1, 2.5, 5, 7.5 and 10 mmol/L) were made by diluting 10 mmol/L stock of glycerol, such as, e.g., with 50 mM Tris-HCl. 5 µL of the sample and glycerol standards (0, 1, 2.5, 5, 7.5 and 10 mmol/L) were added to 0.5 mL of the triglycerides-GPO, mixed, and incubated at room temperature for 5 minutes. The mixture was then vortexed and added (200 µL) to each well of a 96-well flat-bottom ELISA plate (in triplicate). Absorbance (i.e., optical density) was read at 500 nm. The concentrations of the samples were determined via use of a plot of glycerol standards concentration (mmol/L) with respect to optical density (i.e., O.D.) at 500 nm. The concentration of glycerol (mg glycerol/g tissue) was then calculated and triglyceride concentration was determined, in accordance with calculations known to those of ordinary skill in the art.

The experimental protocol described above was conducted in duplicate.

Figure 2:
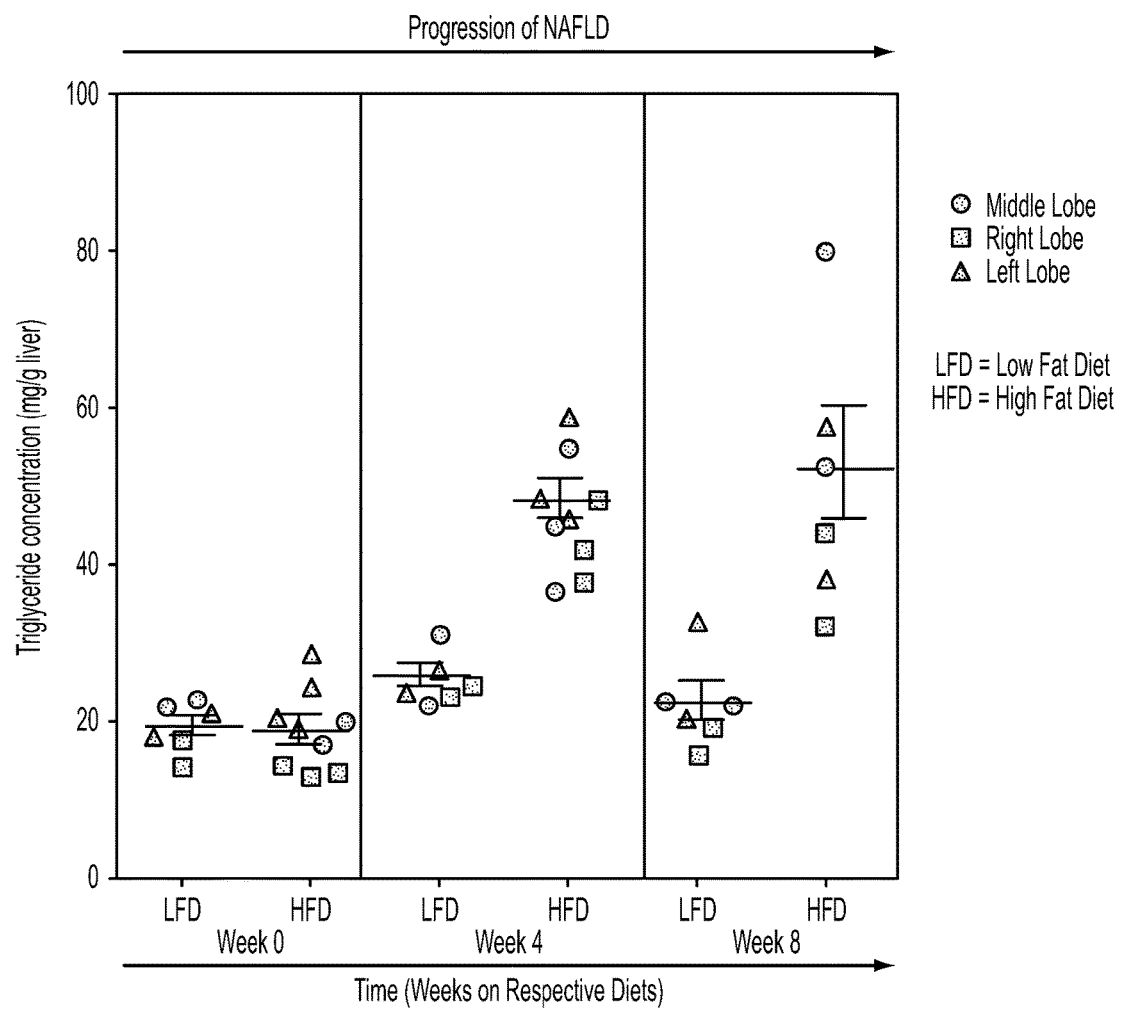
FIG. 2 is a graph of liver tissue harvested from C57BL/6J mice on a LFD and C57BL/6J mice on a HFD at 0 weeks, 4 weeks, and 8 weeks with respect to triglyceride concentration (mg/g liver)

Experimental Results. As shown in FIGS. 1-2, the onset and/or development of NAFLD in C57BL/6J mice was characterized microscopically and molecularly. More specifically, upon removal of the liver tissue from the C57BL/6J mice, it was macroscopically and microscopically observed that the liver tissue from the C57BL/6J mice fed the HFD had greater fat content at weeks 4 and 8 in comparison to the liver tissue from the C57BL/6J fed the LFD (see e.g., FIG. 1). Moreover, as shown in FIG. 1, progression of NAFLD was microscopically observed in C57BL/6J mice fed a HFD from weeks 0-8, wherein excessive accumulation of fat was evident in C57BL/6J mice fed a HFD at week 4, and was clearly observed in C57BL/6J mice fed a HFD at week 8. Additionally, it also was observed that NAFLD does not develop in C57BL/6J mice fed the LFD.

Such macroscopic and microscopic observations were confirmed molecularly. FIG. 2 includes triglyceride content of the middle, right, and left lobes of the liver from the C57BL/6J mice from the first characterization study (i.e., from the experimental protocol described above). More particularly, FIG. 2 includes triglyceride content of the middle, right, and left lobes of the liver from 3 C57BL/6J mice fed a HFD for each of weeks 0, and 4, and of the middle, right, and left lobes of the liver from 2 C57BL/6J mice fed a HFD for 8 weeks, and 2 C57BL/6J mice fed a LFD for each of weeks 0, 4, and 8. As shown in FIG. 2, the liver tissue from the C57BL/6J mice fed the HFD had greater triglyceride content (mg/g liver) at weeks 4 and 8 in comparison to the liver tissue from the CS7BL/6J mice fed the LFD. Moreover, as shown in FIG. 2, the triglyceride content of the liver tissue from the C57BL/6J mice fed the HFD increased from weeks 0-8. Thus, without being bound by the theory, it is believed that NAFLD develops in C57BL/6J mice fed the HFD by at least week 4.

Example 7: Evaluation of COB-204, COB-214, and COB-187 in Preventing and/or Reducing the Risk of NAFLD in Mice Experimental Protocol. 7 week old male C57BL/6J mice (i.e., a mouse model of obesity-induced insulin resistance and Type 2 Diabetes Mellitus) were placed on a HFD (i.e., having a fat content of 60%, a protein content of 20%, and a carbohydrate content of 70%, N=50). The C57BL/6J mice on the HFD were divided into five groups, wherein one such group was immediately given an intraperitoneal sham injection (i.e., Group 1, serving as a stress control N=10), another group was immediately given an intraperiteonal injection of dimethyl sulfoxide (hereinafter, "DMSO", i.e., Group 2, serving as a vehicle control, N=10), another group was immediately given an intraperitoneal injection of 1 mg/kg COB-204 (i.e., Group 3, N=10), another group was immediately given an intraperitoneal injection of 1 mg/kg COB-214 (i.e., Group 4, N=10), and another group was immediately given an intraperitoneal injection of 1 mg/kg COB-187 (i.e., Group 5, N=10). Such injections were initiated with the HFD and were given to the C57BL/6J mice on the HFD once daily for a period of 6 weeks. Food intake and total body weight of the C57BL/6J mice were measured weekly.

At 0 weeks, some of the C57BL/6J mice from each of Groups 1-5 were euthanized (N=5). Liver tissue of the C57BL/6J mice euthanized at 0 weeks was harvested and divided into lobes, including the middle lobe, the right lobe, and the left lobe, for morphological (i.e., hematoxylin and eosin staining) and molecular analysis (i.e., quanitification of triglycerides). The caudate lobe was excluded from such division as the caudate lobe is very small compared to the middle, right, and left lobes. Photographs were taken of the liver tissue both in situ and gross (data not shown) and liver weights were measured (i.e., weights of the total liver and individual lobes were measured, data not shown).

Morphological analysis was performed on the middle lobe of the harvested liver tissue via staining with hematoxylin and eosin. The histological analysis was performed in accordance with methods known to those of ordinary skill in the art. More particularly, liver tissues were fixed in formalin overnight, embedded in paraffin, sectioned, and placed onto slides. Tissue sections were then deparaffinized and rehydrated through a series of xylene and ethanol washes. Hematoxylin and eosin staining was then performed. The stained liver sections were dehydrated through a series of ethanol and xylene washes and mounted for visualization by light microscopy.

Quantification of triglycerides of the middle, right, and left lobes was performed in accordance with the general protocol described in Example 6. Quantification of triglycerides of the middle, right, and left lobes was performed to ensure that accumulation (or lack thereof) of triglycerides was similar in each lobe of the liver and to ensure that a representative analysis of triglyceride accumulation in the liver as a whole was assessed.

At 6 weeks, all of the remaining C57BL/6J mice from each of Groups 1-5 were euthanized (N=5). Photographs of the liver tissue of the C57Bl/6J mice euthanized at 6 weeks were taken both in situ and gross (not shown) and such liver tissue of the C57BL/6J mice was harvested as described previously with regard to the C57BL/6J mice euthanized at 0 weeks. Histological analysis of the middle lobe of the harvested liver tissue was similarly performed. Additionally, quantification of triglycerides of the middle, right, and left lobes was similarly performed.

Figure 4:
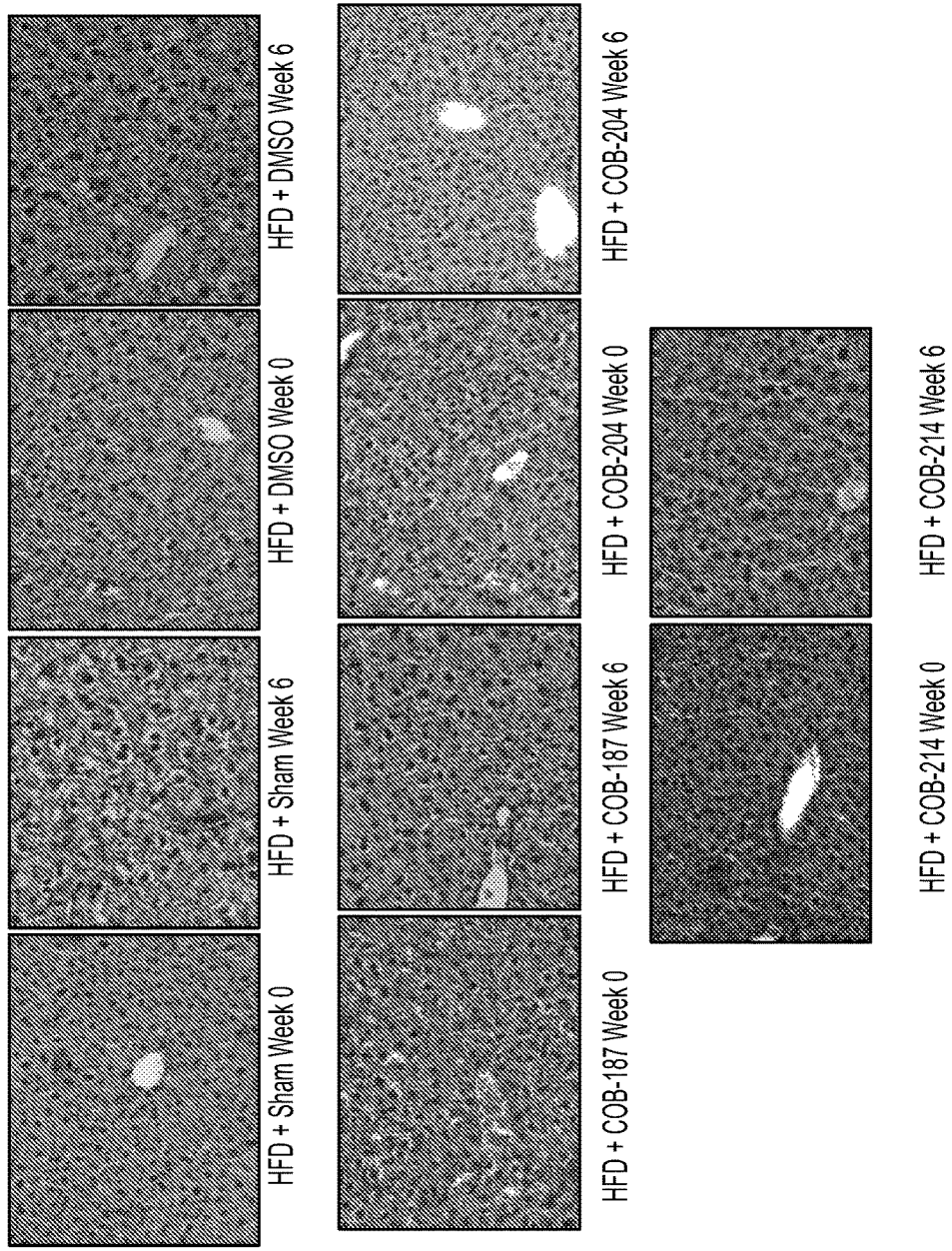
FIG. 4 is a micrograph of the middle lobe of liver tissue harvested from representative C57BL/6J mice on a HFD which were administered sham once daily at 0 weeks (i.e., HFD+Sham Week 0) and at 6 weeks (i.e., HFD+Sham Week 6), or DMSO once daily at 0 weeks (i.e., HFD+DMSO Week 0) and at 6 weeks (i.e., HFD+Week 6), or COB-187 once daily at 0 weeks (i.e., HFD+COB-187 Week 0) and at 6 weeks (i.e., HFD+COB-187 Week 6), or COB-204 once daily at 0 weeks (i.e., HFD+COB-204 Week 0) and at 6 weeks (i.e., HFD+COB-204 Week 6), or COB-214 once daily at 0 weeks (i.e., HFD+COB-214 Week 0) and at 6 weeks (i.e., HFD+COB-214 Week 6).

Experimental Results. Upon removal of the liver tissue from the C57BL/6J mice, it was macroscopically observed that the liver tissue from the mice fed a HFD injected with COB-204, COB-214, or COB-187 (1 mg/kg) had much less fatty liver disease despite obesity compared to the mice on a HFD receiving a sham injection or DMSO injection, despite being obese. More specifically, as shown in FIG. 4, histological examination of middle lobe of liver tissue from the mice fed the HFD which were injected with COB 204, COB-214, or COB-187 revealed that such mice had much less hepatic fat accumulation when compared to the mice fed the HFD which received a sham injection or which were injected with DMSO.

Figure 3:
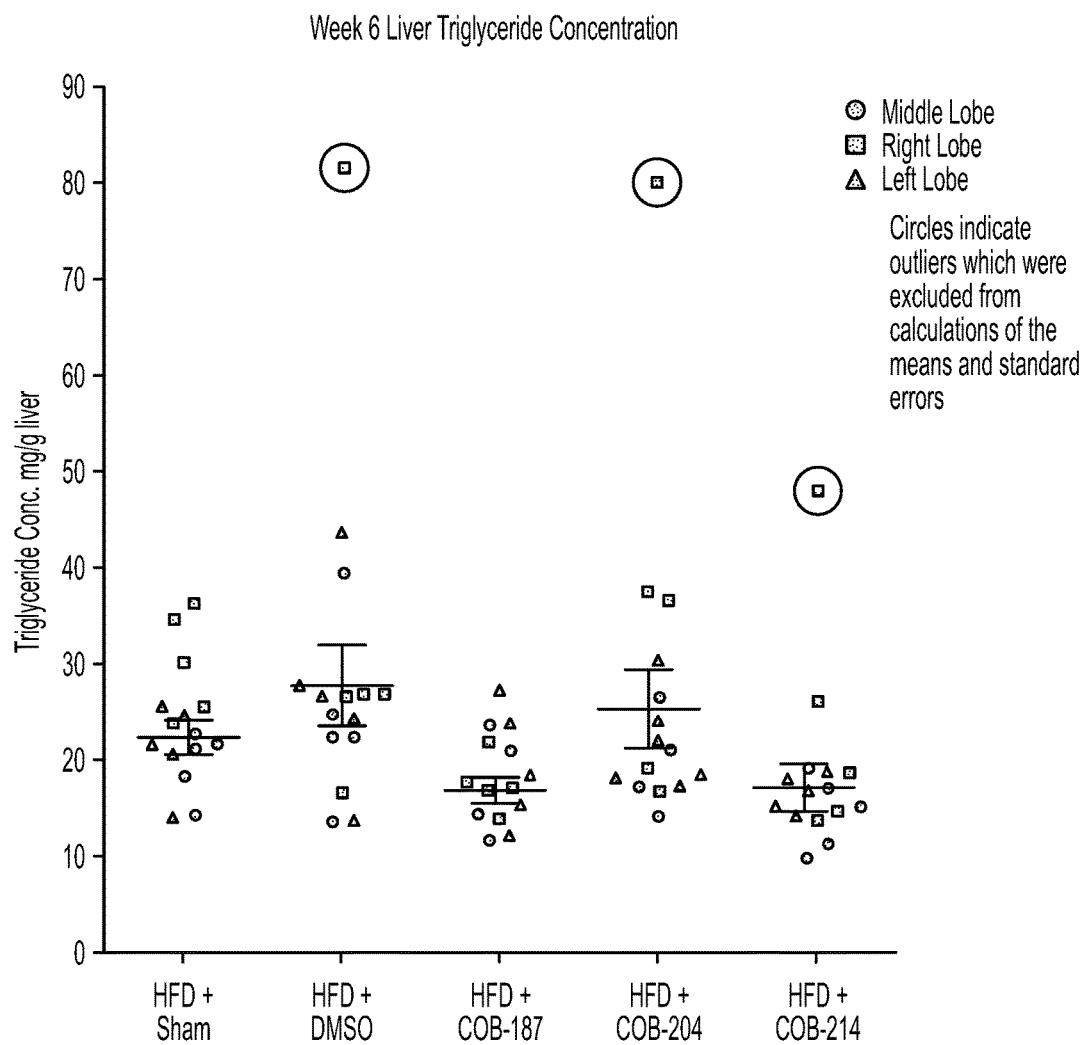
FIG. 3 is a graph of liver tissue (middle lobe, right lobe, and left lobe) harvested from C57BL/6J mice on a HFD for a period of 6 weeks which were administered once daily sham (i.e., HFD+Sham), DMSO (i.e., HFD+DMSO), COB-187 (i.e., HFD+COB-187), COB-204 (i.e., HFD+COB-204), or COB-214 (i.e., HFD+COB 214) for a period of 6 weeks, with respect to triglyceride concentration (mg/g liver)

Additionally, as shown in FIG. 3, such macroscopic observations were confirmed molecularly. More specifically, the amount of triglyceride content (mg/g liver) was measured in the middle, right, and left lobes of liver tissue from the mice fed the HFD injected with Sham, DMSO, COB-204, COB-214, or COB-187 (1 mg/kg). As shown in FIG. 3, the liver tissue of the mice fed the HFD treated with the COB-187 or the COB-214 (1 mg/kg) exhibited a lower mean triglyceride concentration (mg/g liver) than mice fed the HFD or mice fed HFD and treated with DMSO wherein no COB-187 or COB-214 was administered. Although comparison of means in FIG. 3 suggested that there was no effect in mice fed the HFD and treated with COB-204 to prevent fat accumulation in the liver thereof, the means of COB-204 are believed to be due at least in part to variability in the mice. Additionally, it was observed that many more data points in mice fed the HFD and treated with COB-204 were clustered well below the means of both the mice fed the HFD and injected with Sham and the mice fed the HFD and injected with DMSO. More specifically, as shown in Table 4 provided below, the percentage of triglyceride values shown in FIG. 3 of the mice fed the HFD injected with COB-187 (79%), COB-204 (60%), or COB-214 (87%) were well below the mean triglyceride value in FIG. 3 of the mice fed the HFD and injected with Sham. These results further indicate that COB-204 has a therapeutic effect compared to the Sham and DMSO control mice. Thus, quantification of triglycerides was supportive of the morphological findings disclosed in FIG. 4.

TABLE 4

Percentage of Triglyceride Values (mg/g liver) Below the Mean of Mice fed HFD Injected with Sham

|  | Percentage of Triglyceride Values (mg/g liver) Below the Mean of the HFD + Sham Group |
| --- | --- |
| HFD + DMSO | 33% |
| HFD + COB-187 | 79% |
| HFD + COB-204 | 60% |
| HFD + COB-214 | 87% |

Additionally, no significant differences in triglyceride concentration amongst the various lobes of the liver of each mouse (i.e., the middle, right and left lobes of the liver) were observed. Without being bound by the theory, it is believed that COB-204, COB-214 and COB-187 prevented NALFD in mice fed the HFD. Such results indicate that COB-204, COB-214, and COB-187 are useful in the prevention of NAFLD.

It is specifically contemplated that the conclusions made herein based upon the described observations in mice are also applicable to other mammals, including humans. Additionally, one of skill in the art will understand that the specific dosage for use in humans may vary.

Example 8: Evaluation of COB-204, COB-214, COB-152, and COB-187 in Treating NAFLD in C57BL/6J Mice Fed High Fat Diet Contemplated Experimental Protocol. C57BL/6J mice are placed on an HFD containing 60% fat (by % Kcal) (Diet

D12492, Research Diets, Inc.) for a period of weeks (as determined by the results of Example 6) until development of NAFLD is observed and clearly distinguishable from LFD-fed mice of the same age (between 4-8 weeks). At the time or after NAFLD is observed, once daily ip injections of COB-204, COB-214, COB-152, COB-187, DMSO, or sham are administered. Five mice are then euthanized weekly thereafter to characterize the effects of the COB-204, COB-214, COB-152, COB-187, DMSO, and/or sham on treatment of NAFLD for the period of up to 16 weeks post-initiation of the COB-204, COB-214, COB-152, COB-187, DMSO, and sham administration. The period of time for which treatment is administered will be extended to 24 weeks if no effect of the COB-204, COB-214, COB-152, or COB-187 administration on treatment of NAFLD is observed. The following Table further illustrates the experimental design:

TABLE 5

16-Week Treatment of NAFLD Experimental Protocol

| Group | (n) | Diet | Treatment | | |
|---|---|---|---|---|---|
| 1 | 85 | HFD | Sham (i/p injection only) | Stress Control | |
| 2 | 85 | HFD | DMSO (1%) | Vehicle Control | |
| 3 | 85 | HFD | COB-204 | Low | 1 mg/kg/day |
|   | 85 | HFD | COB-214 | Low | 1 mg/kg/day |
|   | 85 | HFD | COB-152 | Low | 1 mg/kg/day |
|   | 85 | HFD | COB-187 | Low | 1 mg/kg/day |
| 4 | 85 | HFD | COB-204 | Medium | 3 mg/kg/day |
|   | 85 | HFD | COB-214 | Medium | 3 mg/kg/day |
|   | 85 | HFD | COB-152 | Medium | 3 mg/kg/day |
|   | 85 | HFD | COB-187 | Medium | 3 mg/kg/day |
| 5 | 85 | HFD | COB-204 | High | 10 mg/kg/day |
|   | 85 | HFD | COB-214 | High | 10 mg/kg/day |
|   | 85 | HFD | COB-152 | High | 10 mg/kg/day |
|   | 85 | HFD | COB-187 | High | 10 mg/kg/day |

If no effect of the COB-204, COB-214, COB-152, or COB-187 administration on treatment of NAFLD is observed by 16 weeks post-initiation of the COB-204, COB-214, COB-152, COB-187, DMSO, and sham administration, a subsequent study is performed wherein the period of time is extended to 24 weeks of the COB-204, COB-214, COB-152, and COB-187 administration, with 5 mice euthanized weekly from weeks 17-24 as previously described. The following Table further illustrates the experimental design:

TABLE 6

17-24-Week Treatment of NAFLD Experimental Protocol

| Group | (n) | Diet | Treatment | | |
|---|---|---|---|---|---|
| 1 | 40 | HFD | Sham (i/p injection only) | Stress Control | |
| 2 | 40 | HFD | DMSO (1%) | Vehicle Control | |
| 3 | 40 | HFD | COB-204 | Low | 1 mg/kg/day |
|   | 40 | HFD | COB-214 | Low | 1 mg/kg/day |
|   | 40 | HFD | COB-152 | Low | 1 mg/kg/day |
|   | 40 | HFD | COB-187 | Low | 1 mg/kg/day |
| 4 | 40 | HFD | COB-204 | Medium | 3 mg/kg/day |
|   | 40 | HFD | COB-214 | Medium | 3 mg/kg/day |
|   | 40 | HFD | COB-152 | Medium | 3 mg/kg/day |
|   | 40 | HFD | COB-187 | Medium | 3 mg/kg/day |
| 5 | 40 | HFD | COB-204 | High | 10 mg/kg/day |
|   | 40 | HFD | COB-214 | High | 10 mg/kg/day |
|   | 40 | HFD | COB-152 | High | 10 mg/kg/day |
|   | 40 | HFD | COB-187 | High | 10 mg/kg/day |

NAFLD is evaluated in the liver of the HFD mice macroscopically, microscopically, and molecularly. More specifically, following euthanasia, the liver of each mouse is removed, weighed, and photographs taken thereof for macroscopic and/or gross observation of NAFLD. Then, the liver of each mouse is split in half, wherein one half is used for microscopic analysis of NAFLD and the remaining half is used for molecular analysis of NAFLD (i.e., quantification of triglycerides). Quantification of triglycerides is performed in accordance with the general protocol described in Example 6.

Contemplated Experimental Results. It is contemplated that the fat content in the liver tissue of the mice is reduced relative to a baseline level, such that the COB-204, COB-214, COB-152, and COB-187 is effective to treat NAFLD. It is specifically contemplated that the conclusions made herein based upon the described observations in mice are also applicable to other mammals, including humans.

Example 10: Therapeutic Use of COB-204, COB-214, COB-152, and COB-187 to Prevent Development of NAFLD Contemplated Experimental Protocol. Patients at risk for developing NAFLD are prescribed COB-204, COB-214, COB-152, or COB-187 to prevent excess accumulation of fat. Each patient takes a once daily oral dose of 1 mg/kg of body weight of the COB-204, COB-214, COB-152, or COB-187, chronically, during which fat content in the liver is determined via liver function testing, liver ultrasound, and liver biopsy.

Contemplated Experimental Results. It is contemplated that no excess accumulation of fat has occurred in the patients, such that the COB-204, COB-214, COB-152, and COB-187 are effective to prevent NAFLD.

Example 11: Therapeutic Use of COB-204, COB-214, COB-152, and COB-187 to Treat NAFLD Contemplated Experimental Protocol. Patients having NAFLD are prescribed COB-204, COB-214, COB-152, or COB-187 to reduce the fat content in their liver. After determination of a baseline level of fat content in each of the patients' livers, each patient takes a once daily oral dose of 3 mg/kg of body weight of the COB-204, COB-214, COB-152, or COB-187, during which fat content in each patient's liver tissue is determined via liver function testing, liver ultrasound, and liver biopsy.

Contemplated Experimental Results. It is contemplated that the fat content in the patient's liver is reduced relative to the baseline level, such that the COB-204, COB-214, COB-152, and COB-187 are effective to treat NAFLD.

Example 12: Pharmaceutical Compositions for Prevention and/or Treatment of NAFLD Useful pharmaceutical formulations for administration of imidazole and/or thiazole compounds may be as described below and may be made using conventional techniques:

Capsules

| | |
|---|---|
| Active Agent/Ingredient | 0.01 to 10 mg |
| Lactose | 20-100 mg |
| Corn Starch U.S.P. | 20-100 mg |
| Aerosolized silica gel | 2-4 mg |
| Magnesium stearate | 1-2 mg |

Tablets

| Active Agent/Ingredient | 0.01 to 10 mg |
|---|---|
| Microcrystalline cellulose | 50 mg |
| Corn Starch U.S.P. | 80 mg |
| Lactose U.S.P. | 50 mg |
| Magnesium stearate U.S.P. | 1-2 mg |

This tablet can be sugar coated according to conventional art practices. Colors may be added to the coating.

Chewable Tablets

| Active Agent/Ingredient | 0.01 to 10 mg |
|---|---|
| Mannitol, N.F. | 100 mg |
| Flavor | 1 mg |
| Magnesium stearate U.S.P. | 2 mg |

Injectable

| Active Agent/Ingredient | 0.05 to 60 mg |
|---|---|
| Polyethylene glycol 600 | 1.0 cc |
| Sodium bisulfite, U.S.P. | 0.4 mg |
| Water for injection, U.S.P. (q.s.) | 2.0 cc |

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present disclosure have been illustrated and described, it would be obvious to one skilled in the art that various other changes and modifications can be made without departing from the spirit and scope of the disclosure. It is therefore intended to cover in the appended claims all such changes and modifications that are within the scope of this disclosure.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Throughout the specification and claims, a given chemical formula or name shall encompass all tautomers and optical and stereoisomers, as well as racemic mixtures where such isomers and mixtures exist.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise. For example, reference to "a liver cell" may include both reference to a single liver cell and reference to a plurality of liver cells.

The invention claimed is:

1. A method for treating or reducing the risk of developing non-alcoholic fatty liver disease (NAFLD) in a subject in need thereof, the method comprising:
    administering to the subject a therapeutically effective amount of at least one compound of General Formula (I) or (II):

or a pharmaceutically-acceptable salt or solvate thereof, in which:
    $R^1$ is chosen from methyl, ethyl, propyl, 2-propenyl, hexyl, $Q^1$,

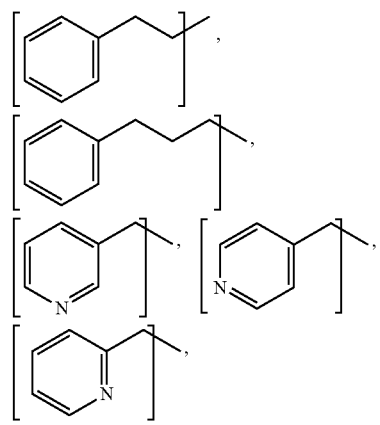

-continued

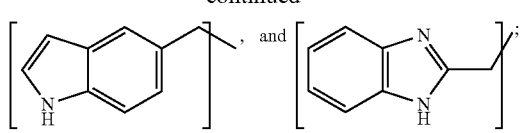

R² is chosen from Q², phenyl,

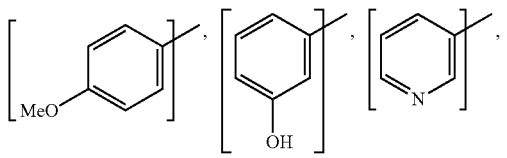

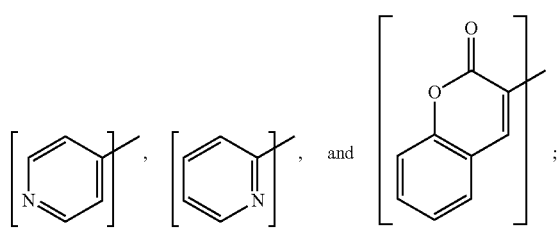

R³ is chosen from H, -methyl, ethyl, n-propyl, iso-propyl, butyl, 3-butenyl, phenyl, or 2-phenylethyl;
Q¹ is

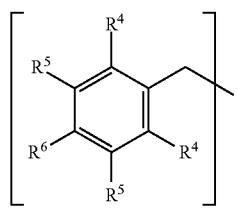

in which groups R⁴, R⁵, and R⁶ are independently chosen from H, halo, —NO₂, —CN, or —OCH₃; and
Q² is

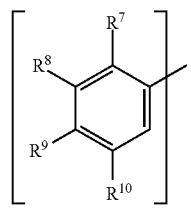

in which exactly two or exactly three of groups R⁷, R⁸, R⁹, and R¹⁰ are hydrogen and remaining groups R⁷, R⁸, R⁹, and R¹⁰ that are not hydrogen are independently chosen from methoxy, ethoxy, hydroxy, trifluoromethoxy, methyl, trifluoromethyl, N-methylamino, (N,N)-dimethylamino, cyano, halo, or nitro;
  with the proviso that when R² is phenyl and R³ is —H, R¹ is selected from the group consisting of hexyl, Q¹,

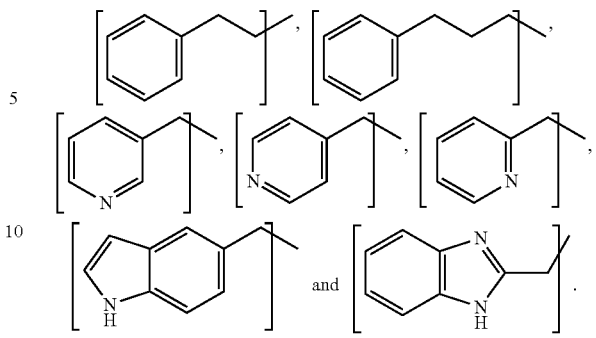

2. The method of claim 1, wherein administration of the at least one compound of General Formula (I) or (II) is effective to treat NAFLD.

3. The method of claim 1, wherein administration of the at least one compound of General Formula (I) or (II) is effective to treat NAFLD by reducing fat content in liver tissue of the subject relative to a baseline level.

4. The method of claim 1, wherein the subject is a mammal, and wherein the at least one compound of General Formula (I) or (II) is administered systemically.

5. The method of claim 1, wherein the at least one compound of General Formula (I) or (II) is administered in a daily dose of about 1 mg/kg to about 10 mg/kg.

6. The method of claim 1, wherein:
R³ is —H
in the at least one compound of General Formula (I) or (II).

7. The method of claim 1, wherein:
R¹ is selected from the group consisting of methyl, propyl, hexyl, 2-propenyl,

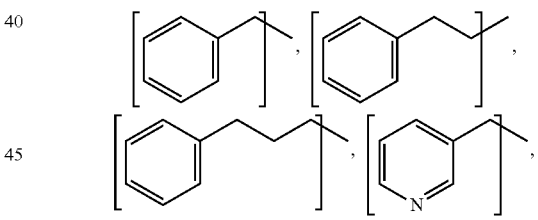

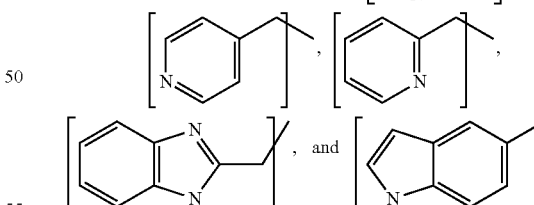

in the at least one compound of General Formula (I) or (II).

8. The method of claim 1, wherein:
R² is Q²; and
exactly two or exactly three groups of groups R⁷, R⁸, R⁹, and R¹⁰ are hydrogen, and remaining groups R⁷, R⁸, R⁹, and R¹⁰ that are not hydrogen are methoxy;
in the at least one compound of General Formula (I) or (II).

9. The method of claim 1, wherein:
R¹ is selected from the group consisting of

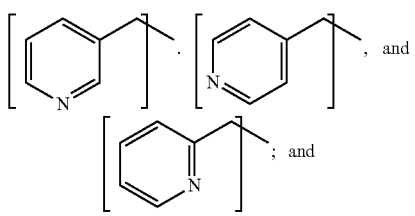

R³ is —H
in the at least one compound of General Formula (I) or (II).

10. The method of claim 1, wherein:
R² is selected from the group consisting of phenyl,

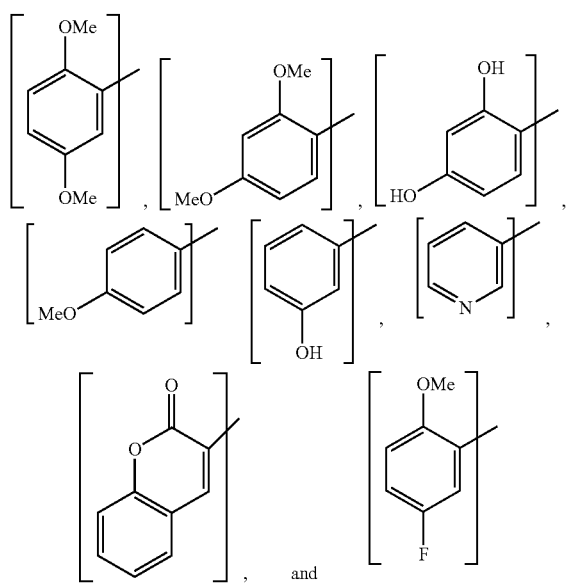

in the at least one compound of General Formula (I) or (II).

11. The method of claim 1, wherein:
R¹ is chosen from

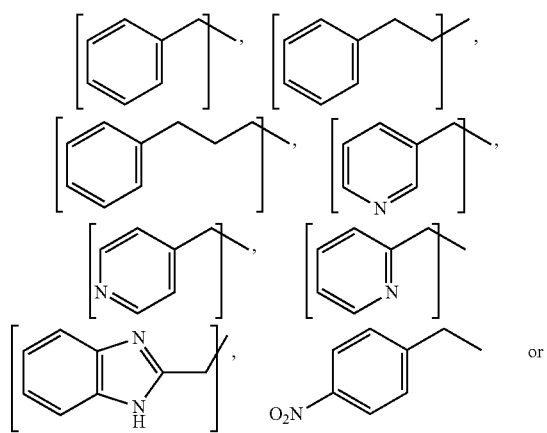

-continued

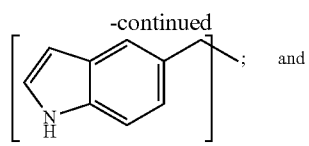

R² is chosen from phenyl,

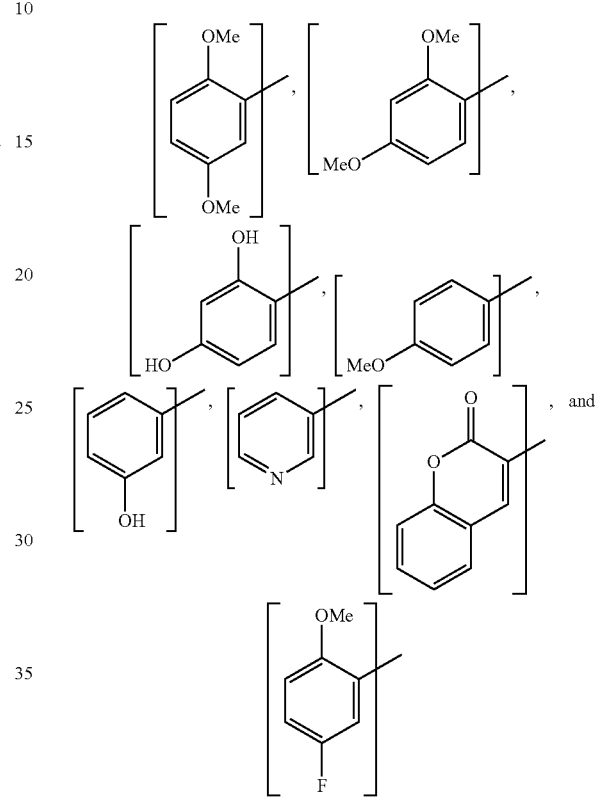

in the at least one compound of formula (I) or (II).

12. The method of claim 1, wherein:
R¹ is chosen from methyl or and

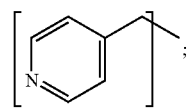

R² is chosen from phenyl,

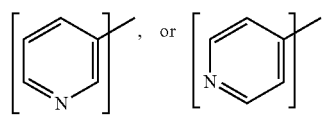

in the at least one compound of formula (I) or (II).

13. The method of claim 1, wherein the at least one compound of General Formula (I) or (II) is chosen from COB-152, COB-187, COB-204, COB-214, or combination thereof, and pharmaceutically acceptable salts and solvates thereof:

(COB-152) 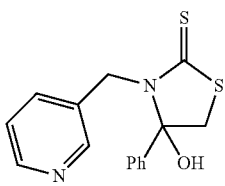

(COB-187) 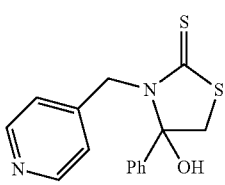

(COB-204) 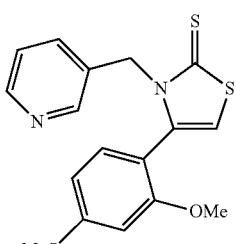

(COB-214) 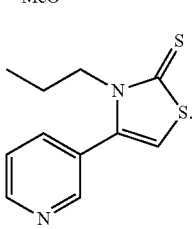

14. A method for inhibiting excessive accumulation of fat in liver tissue, the method comprising:

contacting the liver tissue with a therapeutically effective amount of at least one compound of General Formula (I) or (II):

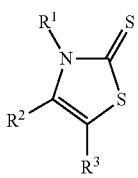
(I)

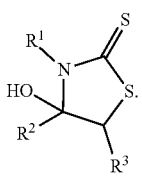
(II)

or a pharmaceutically-acceptable salt or solvate thereof, in which:

$R^1$ is chosen from methyl, ethyl, propyl, 2-propenyl, hexyl, $Q^i$,

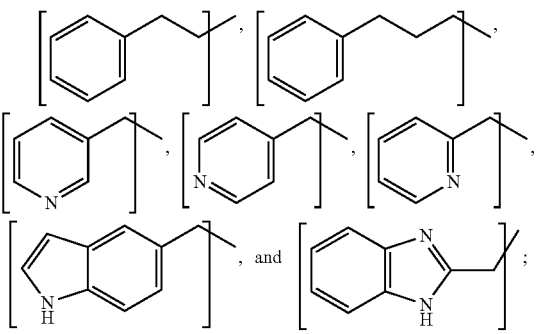

$R^2$ is chosen from $Q^2$, phenyl,

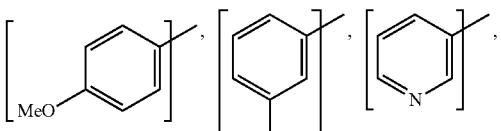

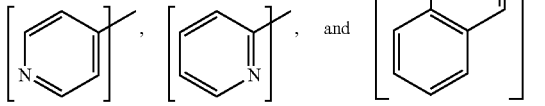

$R^3$ is chosen from —H, -methyl, ethyl, n-propyl, isopropyl, butyl, 3-butenyl, phenyl, or 2-phenyl-ethyl;

$Q^1$ is

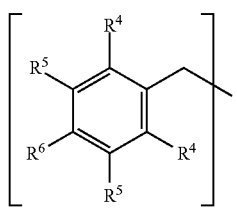

in which groups $R^4$, $R^5$, and $R^6$ are independently chosen from —H, halo, —NO$_2$, —CN, or —OCH$_3$; and $Q^2$ is

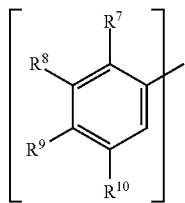

in which exactly two or exactly three of groups $R^7$, $R^8$, $R^9$, and $R^{10}$ are hydrogen and remaining groups $R^7$, $R^8$, $R^9$, and $R^{10}$ that are not hydrogen are independently chosen from methoxy, ethoxy, hydroxy, trifluoromethoxy, methyl, trifluoromethyl, N-methylamino, (N,N)-dimethylamino, cyano, halo, or nitro;

with the proviso that when $R^2$ is phenyl and $R^3$ is —H, $R^1$ is selected from the group consisting of hexyl, $Q^1$,

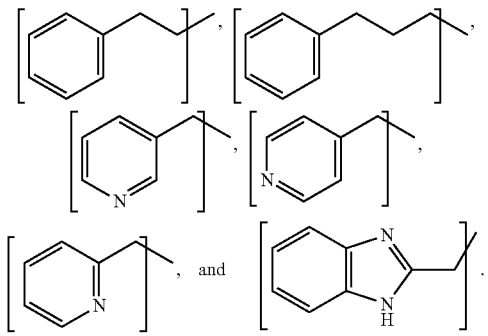

15. The method of claim 1, wherein:
$R^1$ is $Q^1$, in which groups $R^4$, and $R^5$ are hydrogen, and $R^6$ is chosen from —Cl, —NO$_2$, —CN, or —OCH$_3$ in the at least one compound of General Formula (I) or (II).

16. The method of claim 1, wherein:
$R^1$ is propyl; and
$R^2$ is selected from the group consisting of

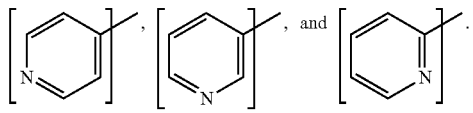

17. The method of claim 1, further comprising co-administering with the at least one compound of General Formula (I) or (II) a therapeutically effective amount of at least one of metformin, thiazolidinediones, or 3-hydroxy-3-methyl-glutaryl-CoA reductase inhibitors.

* * * * *

UNITED STATES PATENT AND TRADEMARK OFFICE
CERTIFICATE OF CORRECTION

PATENT NO. : 10,392,381 B2
APPLICATION NO. : 15/326771
DATED : August 27, 2019
INVENTOR(S) : Kelly D. McCall et al.

Page 1 of 1

It is certified that error appears in the above-identified patent and that said Letters Patent is hereby corrected as shown below:

In the Specification

In Column 58, Line 4, before "tissue" delete "liiver" and insert --liver--, therefor.

Signed and Sealed this
Twenty-fourth Day of March, 2020

Andrei Iancu
*Director of the United States Patent and Trademark Office*